United States Patent
Freedman et al.

(10) Patent No.: US 11,963,850 B2
(45) Date of Patent: Apr. 23, 2024

(54) MECHANICAL WOUND THERAPY FOR SUB-ATMOSPHERIC WOUND CARE SYSTEM

(71) Applicant: J&M Shuler Medical, Inc., Athens, GA (US)

(72) Inventors: Brett A. Freedman, Ramstein-Meisenbach (DE); Michael Simms Shuler, Athens, GA (US)

(73) Assignee: J&M Shuler Medical Inc., Athens, GA (US)

( * ) Notice: Subject to any disclaimer, the term of this patent is extended or adjusted under 35 U.S.C. 154(b) by 1055 days.

(21) Appl. No.: 16/694,897

(22) Filed: Nov. 25, 2019

(65) Prior Publication Data

US 2020/0101208 A1 Apr. 2, 2020

Related U.S. Application Data

(60) Continuation of application No. 15/187,335, filed on Jun. 20, 2016, now Pat. No. 10,485,906, which is a
(Continued)

(51) Int. Cl.
*A61F 13/00* (2006.01)
*A61F 13/02* (2006.01)
(Continued)

(52) U.S. Cl.
CPC .... *A61F 13/00063* (2013.01); *A61F 13/0216* (2013.01); *A61F 13/0279* (2013.01);
(Continued)

(58) Field of Classification Search
CPC .......... A61F 13/00063; A61F 13/00068; A61F 13/0216; A61F 2013/00536;
(Continued)

(56) References Cited

U.S. PATENT DOCUMENTS

| | | | |
|---|---|---|---|
| 4,460,354 | A | 7/1984 | Weilbacher et al. |
| 4,559,035 | A | 12/1985 | Benjamin et al. |

(Continued)

FOREIGN PATENT DOCUMENTS

| | | |
|---|---|---|
| CA | 2619925 | 3/2007 |
| EP | 1304966 | 5/2003 |

(Continued)

OTHER PUBLICATIONS

U.S. Appl. No. 13/843,507, filed Mar. 15, 2013, Freedman.
(Continued)

*Primary Examiner* — Andrew J Mensh
(74) *Attorney, Agent, or Firm* — Fish & Richardson P.C.

(57) ABSTRACT

A mechanical wound therapy (MWT) system includes a connection for a vacuum source, which is routed through an airtight covering to a porous material positioned over the wound. The porous material may be a tubing network interspaced by a netting material constructed of biologically inert or bioabsorbable material. Alternatively, the porous material may be a layered unified dressing in which layers of mesh, netting or thin perforated film are separated and fixedly attached to functional elements of the dressing (e.g., irrigation tubing) or spacers. The vacuum and irrigation systems may be completely separated. An airtight sealing layer or foldable adhesive sealing layer may seal the dressing and facilitate sealing the dressing to the wound margins. Additional modular devices such as a wound approximating system, positive pressure bladders and adjuvant therapy modules as well as enhanced monitoring technology can be added to synergistically increase the capabilities of each dressing.

20 Claims, 30 Drawing Sheets

Related U.S. Application Data division of application No. 13/652,445, filed on Oct. 15, 2012, now Pat. No. 9,393,354.

(60) Provisional application No. 61/643,840, filed on May 7, 2012, provisional application No. 61/554,080, filed on Nov. 1, 2011.

(51) Int. Cl.

| | | |
|---|---|---|
| *A61M 1/00* | (2006.01) | |
| *A61M 3/02* | (2006.01) | |
| *A61M 37/00* | (2006.01) | |
| *A61N 5/06* | (2006.01) | |
| *A61N 7/00* | (2006.01) | |
| A61B 46/00 | (2016.01) | |

(52) U.S. Cl.
CPC ............... *A61M 1/77* (2021.05); *A61M 1/85* (2021.05); *A61M 1/915* (2021.05); *A61M 1/92* (2021.05); *A61M 1/966* (2021.05); *A61M 3/0279* (2013.01); *A61M 3/0283* (2013.01); *A61M 37/00* (2013.01); *A61N 5/0624* (2013.01); *A61N 7/00* (2013.01); *A61B 46/00* (2016.02); *A61F 13/00* (2013.01); *A61F 13/00021* (2013.01); *A61F 13/00068* (2013.01); *A61F 13/00085* (2013.01); *A61F 2013/00357* (2013.01); *A61F 2013/00536* (2013.01); *A61F 13/023* (2013.01); *A61M 1/916* (2021.05); *A61M 2205/15* (2013.01); *A61M 2205/18* (2013.01); *A61M 2205/3344* (2013.01); *A61M 2205/3553* (2013.01); *A61M 2205/3584* (2013.01); *A61M 2205/3592* (2013.01); *Y10T 29/49826* (2015.01)

(58) Field of Classification Search
CPC .. A61M 3/0279; A61M 3/0283; A61M 37/00; Y10T 29/49826
USPC ......................................................... 604/305
See application file for complete search history.

(56) References Cited

U.S. PATENT DOCUMENTS

| | | | |
|---|---|---|---|
| 4,886,502 A | 12/1989 | Poirier et al. | |
| 4,969,880 A | 11/1990 | Zamierowski | |
| 5,071,409 A | 12/1991 | Rosenberg | |
| 5,100,396 A | 3/1992 | Zamierowski | |
| 5,176,663 A | 1/1993 | Svedman et al. | |
| 5,261,893 A | 11/1993 | Zamierowski | |
| 5,358,494 A | 10/1994 | Svedman | |
| 5,527,293 A | 6/1996 | Zamierowski | |
| 5,549,584 A | 8/1996 | Gross | |
| 5,636,643 A | 6/1997 | Argenta et al. | |
| 5,645,081 A | 7/1997 | Argenta et al. | |
| 5,678,564 A | 10/1997 | Lawrence et al. | |
| 5,755,706 A | 5/1998 | Kronenthal et al. | |
| 5,911,222 A | 6/1999 | Lawrence et al. | |
| 6,045,541 A | 4/2000 | Matsumoto et al. | |
| 6,048,337 A | 4/2000 | Svedman | |
| 6,071,267 A | 6/2000 | Zamierowski | |
| 6,142,982 A | 11/2000 | Hunt et al. | |
| 6,176,868 B1 | 1/2001 | Detour | |
| 6,345,623 B1 | 2/2002 | Heaton et al. | |
| 6,458,109 B1 | 10/2002 | Henley et al. | |
| 6,468,237 B1 | 10/2002 | Lina | |
| 6,685,681 B2 | 2/2004 | Anker et al. | |
| 6,695,823 B1 | 2/2004 | Lina et al. | |
| 6,752,794 B2 | 6/2004 | Lockwood et al. | |
| 6,764,462 B2 | 7/2004 | Risk, Jr. et al. | |
| 6,767,334 B1 | 7/2004 | Randolph | |
| 7,004,915 B2 | 2/2006 | Boynton et al. | |
| 7,022,113 B2 | 4/2006 | Lockwood et al. | |
| 7,108,683 B2 | 9/2006 | Zamierowski | |
| 7,117,869 B2 | 10/2006 | Heaton et al. | |
| 7,276,051 B1 | 10/2007 | Henley et al. | |
| 7,338,482 B2 | 3/2008 | Lockwood et al. | |
| 7,361,184 B2 | 4/2008 | Joshi | |
| 7,413,571 B2 | 8/2008 | Zamierowski | |
| 7,438,705 B2 | 10/2008 | Karpowicz et al. | |
| 7,520,872 B2 | 4/2009 | Biggie et al. | |
| 7,524,286 B2 | 4/2009 | Johnson | |
| 7,524,315 B2 | 4/2009 | Blott et al. | |
| 7,532,953 B2 * | 5/2009 | Vogel ..................... | A61M 1/96 700/282 |
| 7,534,927 B2 | 5/2009 | Lockwood et al. | |
| 7,608,066 B2 | 10/2009 | Vogel | |
| 7,651,484 B2 | 1/2010 | Heaton et al. | |
| 7,723,560 B2 | 5/2010 | Lockwood et al. | |
| 7,790,945 B1 | 9/2010 | Watson | |
| 7,837,673 B2 | 11/2010 | Vogel | |
| 7,867,206 B2 | 1/2011 | Lockwood et al. | |
| 7,883,494 B2 | 2/2011 | Martin | |
| 7,922,703 B2 | 4/2011 | Riesinger | |
| 7,927,318 B2 | 4/2011 | Risk, Jr. et al. | |
| 7,951,100 B2 | 5/2011 | Hunt et al. | |
| 7,967,810 B2 | 6/2011 | Freedman | |
| 7,988,680 B2 | 8/2011 | Lockwood et al. | |
| 8,057,446 B2 | 11/2011 | Kane et al. | |
| 8,066,243 B2 | 11/2011 | Svedman et al. | |
| 8,142,405 B2 | 3/2012 | Vogel | |
| 8,162,909 B2 | 4/2012 | Blott et al. | |
| 8,187,210 B2 | 5/2012 | Hunt et al. | |
| 8,350,116 B2 | 1/2013 | Lockwood et al. | |
| 8,372,049 B2 | 2/2013 | Jaeb et al. | |
| 8,376,972 B2 | 2/2013 | Fleischmann | |
| 8,425,478 B2 | 4/2013 | Olson | |
| 8,444,613 B2 | 5/2013 | Svedman et al. | |
| 8,447,375 B2 | 5/2013 | Freedman et al. | |
| 8,460,258 B2 | 6/2013 | Jones et al. | |
| 8,460,273 B2 | 6/2013 | Freedman et al. | |
| 2001/0031943 A1* | 10/2001 | Urie ..................... | A61M 1/915 604/47 |
| 2002/0115967 A1* | 8/2002 | Svedman ........... | A61B 5/14532 604/315 |
| 2002/0143286 A1 | 10/2002 | Tumey | |
| 2002/0150720 A1 | 10/2002 | Howard et al. | |
| 2002/0183702 A1 | 12/2002 | Henley | |
| 2003/0050594 A1 | 3/2003 | Zamierowski | |
| 2003/0139255 A1 | 7/2003 | Lina | |
| 2003/0163160 A1 | 8/2003 | O'Malley et al. | |
| 2003/0208149 A1 | 11/2003 | Coffey | |
| 2004/0006319 A1 | 1/2004 | Lina et al. | |
| 2004/0054338 A1 | 3/2004 | Bybordi et al. | |
| 2004/0064111 A1 | 4/2004 | Lockwood et al. | |
| 2004/0064132 A1 | 4/2004 | Boehringer et al. | |
| 2004/0265040 A1 | 12/2004 | Rosenberg | |
| 2005/0070858 A1 | 3/2005 | Lockwood et al. | |
| 2005/0085795 A1 | 4/2005 | Lockwood | |
| 2006/0041238 A1 | 2/2006 | Bowen | |
| 2006/0065494 A1 | 3/2006 | Kim | |
| 2006/0129137 A1 | 6/2006 | Lockwood et al. | |
| 2006/0155260 A1 | 7/2006 | Blott et al. | |
| 2006/0282028 A1 | 12/2006 | Howard et al. | |
| 2007/0038247 A1 | 2/2007 | Lebner et al. | |
| 2007/0167926 A1 | 7/2007 | Blott et al. | |
| 2007/0225634 A1 | 9/2007 | Ferren et al. | |
| 2007/0225663 A1 | 9/2007 | Watt et al. | |
| 2008/0167593 A1 | 7/2008 | Fleischmann | |
| 2008/0208011 A1 | 8/2008 | Shuler | |
| 2008/0255498 A1* | 10/2008 | Houle ................. | A61C 17/0208 604/20 |
| 2009/0177051 A1 | 7/2009 | Arons et al. | |
| 2009/0221977 A1* | 9/2009 | Blott ..................... | A61M 35/30 604/290 |
| 2009/0299340 A1* | 12/2009 | Kazala, Jr. .............. | A61M 1/71 128/849 |
| 2010/0049150 A1* | 2/2010 | Braga ................... | A61M 1/784 604/313 |
| 2010/0049151 A1 | 2/2010 | Aicher | |

(56) References Cited

U.S. PATENT DOCUMENTS

| | | |
|---|---|---|
| 2010/0191196 A1* | 7/2010 | Heagle .................. B29C 66/232 604/313 |
| 2010/0191198 A1 | 7/2010 | Heagle |
| 2010/0262091 A1 | 10/2010 | Larsson |
| 2010/0280428 A1 | 11/2010 | Widgerow et al. |
| 2010/0292549 A1 | 11/2010 | Shuler |
| 2011/0034888 A1 | 2/2011 | Aali |
| 2011/0054283 A1 | 3/2011 | Shuler |
| 2011/0106026 A1 | 5/2011 | Wu et al. |
| 2011/0125110 A1 | 5/2011 | Cotton |
| 2011/0172617 A1 | 7/2011 | Riesinger |
| 2011/0213319 A1 | 9/2011 | Blott et al. |
| 2012/0041403 A1 | 2/2012 | Bennett et al. |
| 2012/0316518 A1 | 12/2012 | Croizt et al. |
| 2013/0096520 A1 | 4/2013 | Lockwood et al. |
| 2013/0138060 A1 | 5/2013 | Haggstrom et al. |
| 2013/0144230 A1 | 6/2013 | Wu et al. |
| 2013/0165821 A1 | 6/2013 | Freedman et al. |
| 2013/0165878 A1 | 6/2013 | Heagle |
| 2013/0172834 A1 | 7/2013 | Heagle |
| 2013/0274695 A1 | 10/2013 | Freedman et al. |
| 2019/0111192 A1 | 4/2019 | Shuler |
| 2019/0240383 A1 | 8/2019 | Freedman et al. |

FOREIGN PATENT DOCUMENTS

| | | |
|---|---|---|
| WO | WO 1997/005838 | 2/1997 |
| WO | WO 2007/041642 | 4/2007 |
| WO | WO 2008/100440 | 8/2008 |
| WO | WO 2009/062327 | 5/2009 |
| WO | WO 2009/093116 | 7/2009 |
| WO | WO 2011/091045 | 7/2011 |

OTHER PUBLICATIONS

U.S. Appl. No. 13/867,100, filed Apr. 21, 2013, Shuler et al..
U.S. Appl. No. 60/853,000, filed Oct. 20, 2006, Freedman.
U.S. Appl. No. 61/233,797, filed Aug. 13, 2009, Shuler.
U.S. Appl. No. 61/234,857, filed Aug. 18, 2009, Shuler.
U.S. Appl. No. 61/245,789, filed Sep. 25, 2009, Shuler.
U.S. Appl. No. 61/554,080, filed Nov. 1, 2011, Freedman.
U.S. Appl. No. 61/643,840, filed May 7, 2012, Freedman.
International Preliminary Report on Patentability in International Application No. PCT/US2012/061770, dated May 6, 2014, 12 pages.
International Search Report in International Application No. PCT/US2012/061770, dated Mar. 2, 2012, 3 pages.
Australian Office Action in Australian Application No. 2012332941, dated Jul. 13, 2016, 2 pages.
Canadian Office Action in Application No. 2,769,671, dated May 16, 2017, 4 pages.
Argenta et al., "Vacuum-Assisted Closure: A New Method For Wound Control And Treatment: Basic Foundation," Annals Of Plastic Surgery, 1997, 38(6): 553-562.
Argenta et al., "Vacuum-Assisted Closure: A New Method For Wound Control And Treatment: Clinical Experience," Annals of Plastic Surgery, 1997, 38(6): 563-577.
Brock et al., "Temporary Closure of Open Abdominal Wounds: The Vacuum Pack," Am Surg., 1995, 61(1): 30-35.
Buckman, "Vacuum Assisted Wound Closure System," Drexel University white paper, Jul. 15, 2006.
Davydov et al., "Concepts for Clinical Biological Management of the Wound Process in the Treatment of Purulent Wounds Using Vacuum Therapy," The Kremlin Papers; Perspectives in Wound Care from the Russian Medical Journal, 1991, 132-135.
Davydov et al., "The Bacteriological and Cytological Assessment of Vacuum Therapy of Purulent Wounds," The Kremlin papers, Perspectives in Wound Care from the Russian Medical Journal, 1988, 48-52.
Davydov et al., "Vacuum Therapy in the Treatment of Purulent lactation Mastitis," The Kremlin papers, perspectives in Wound Care from the Russian Medical Journal, 1986, 66-70.
Kostiuchenok et al., "The Vacuum Effect in the Surgical Treatment of Purulent Wounds," The Kremlin Papers, Perspectives in Wound Care from the Russian Medical Journal, 1986, 18-21.
Scherer et al., "The vacuum assisted closure device: A method for securing skin grafts and improving graft survival," Arch Surg., 2002, 137(8): 930-933.
Singh et al., "Dynamic Wound Closure for Decompressive Leg Fasciotomy Wounds," Am Surg, 2008, 74(3): 217-220.
Usupov et al., "Active Wound Drainage," The Kremlin Papers, Perspectives in Wound Care from the Russian Medical Journal, 1987, 42-45.
Valenta, "Using the Vacuum Dressing Alternative for Difficult Wounds," American J. of Nursing, 1994, 44-45.
Van der Velde and Hudson, "VADER (vacuum-assisted dermal recruitment: a new method of wound closure," Annals of Plastic Surgery, 2005, 55(6): 660-664.
Wackenfors, et al., "Effects of vacuum-assisted closure therapy on inguinal wound edge microvascular blood flow," Wound Repaire and Regeneration, 2004, 12(6): 600-606.
Webb, "New Techniques in Wound Management: Vacuum-assisted Wound Closure," J. Am Acad Orthop Surg, 2002, 10(5): 303-311.
Zannis et al, "Comparison of Fasciotomy Wound Closures Using Traditional Dressing Changes and the Vacuum-assisted Closure Device," Annals of Plastic Surgery, 2009, 62(4): 407-409.
Zorilla, et al, "Shoelace technique for gradual closure of fasciotomy wounds," The Journal of Trama, 2005, 59(6): 1515-1517.

* cited by examiner

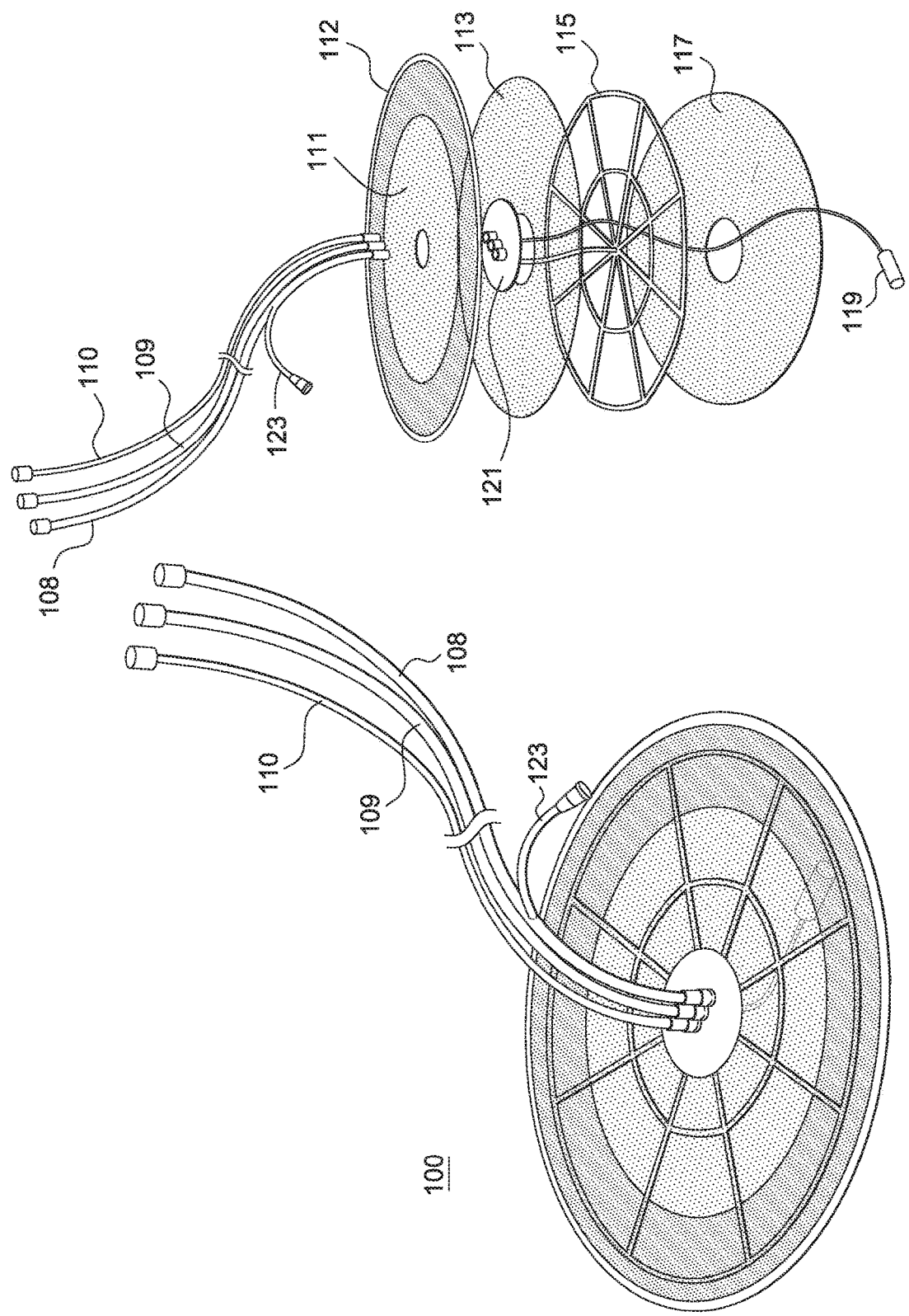

MECHANICAL WOUND THERAPY FOR SUB-ATMOSPHERIC WOUND CARE SYSTEM

CROSS-REFERENCE TO RELATED APPLICATIONS

The present application is a continuation of U.S. patent application Ser. No. 15/187,335 filed Jun. 20, 2016, now issued as U.S. Pat. No. 10,485,906, which is a divisional application and claims priority to U.S. patent application Ser. No. 13/652,445 filed Oct. 15, 2012, now issued as U.S. Pat. No. 9,393,354, which claims priority to both U.S. provisional patent application 61/554,080 filed Nov. 1, 2011, and also U.S. provisional patent application 61/643,840 filed May 7, 2012, all of these earlier applications being incorporated by reference in their entirety.

BACKGROUND

Technical Field

Various embodiments of the present invention relate to patient wound care, and more specifically, to systems and methods of wound coverings and dressings.

Description of Related Art

Since the mid-20th century various types of rudimentary vacuum-assisted devices have been used to facilitate coverage and closure of open wounds. Conventional vacuum-assisted wound care devices use a non-unified, piecemeal wound filling material sealed with an adhesive film, and a vacuum pump that maintains negative pressure on the wound while draining the effluent from the wound into a fluid collection canister.

There is sometimes a need to modify the wound dressing to provide a shape conforming to the wound. In a common conventional system this is done with wound filler material, often made of an open-cell reticulated polyurethane sponge material or cotton gauze. The sponge wound filler material—often black in color, or otherwise opaque—must be cut to the shape and contour of the wound. This material is not particularly easy to cut to shape, generally resulting in multiple odd shaped pieces of sponge that need to be held in a piecemeal fashion within the wound until an adhesive film can be placed to seal the dressing. The present inventors recognized drawbacks in using this piecemeal approach. These drawbacks exist for the known conventional wound fillers used in negative pressure wound therapy devices.

Different ways of filling the wound cavity have been attempted for the application of negative pressure wound therapy. U.S. Pat. No. 6,752,794 to Lockwood (Lockwood '794) describes irrigation and vacuum passageways created as channels in a solid noncompressible non-porous member. (See Lockwood '794, FIGS. 12 and 35). Lockwood '794 uses separate ports for vacuum and irrigation. However, one of the several limitations of this design is that the vacuum passageway between the wound bed and the dorsally located vacuum port can only occur through the limited number of perforations placed within the solid noncompressible member and that which traverses around the periphery of the member. Additionally, the communication between irrigation source tubing and the dressing member is explicitly demonstrated with a peripheral/horizontal plane attachment site, which is believed to be inherent to the design described in the Lockwood '794 patent. This limits the ability to custom cut any portion of the periphery of the member to the dimensions of each wound. Likewise, the irrigation passageways specifically stop short of the peripheral extent of the irrigation member.

There are also drawbacks relating to the vacuum regulation system of conventional devices. Conventional negative pressure wound treatment (NPWT) devices often make broad reference to not placing the dressing in proximity to vascular structures. However, the conventional systems do not specify what would be a safe distance from these structures. Since all portions of the body are "in proximity" to vessels, these conventional systems provide no means for mitigating the risk of exsanguination. There have been catastrophic complications, even leading to patient deaths, related to exsanguination events reported to the Federal Drug Administration (FDA) and Centers for Medicare and Medicaid Services (CMS) for certain conventional NPWT systems.

While use of NPWT has become increasingly widespread in the last two decades, the technologies available in this field remain narrowly focused, and are subject to the aforementioned drawbacks and a number of other shortcomings. Moreover, the present inventors feel NPWT is not a stand-alone concept, but that it is a piece in the overall wound care process. The management of open wounds from trauma or disease, with the assistance of NPWT, could benefit from the application of multiple other features which are not provided by any conventional NPWT system. One significant limitation of current art is the lack of a method for integrating most or all of the commonly used methods of wound care into a single mechanical system.

BRIEF SUMMARY

Various embodiments are disclosed that do not require pieces of sponge or freely placed piecemeal fillers. In some embodiments there is no need for a rigid collection canister. Rather, a malleable bag is used for collection of the fluids.

Various embodiments disclosed herein are drawn to an integrated mechanical wound therapy (MWT) system. The various embodiments combine different aspects of wound care, which currently operate in a segregated fashion. Operating in such a segregated manner is often disadvantageous in terms of consistency, efficiency and efficacy of wound care. Further, some elements of modern wound care cannot readily be performed without integration of the component parts into the MWT system. For example, various embodiments of the integrated wound care systems disclosed herein benefit from some or all of the following features: Negative pressure wound therapy; Wound monitoring; Irrigation; Debridement; Delivery of adjuvant therapies (e.g., chemical, biological, mechanical, energy systems); Wound contraction (e.g., controlled wound approximation/dermatotraction); and/or Edema control (e.g., intermittent positive-pressure).

The current inventors are the first to describe a unified dressing capable of providing NPWT. In regards to the novel dressing embodiments described herein, the term unified is intended to indicate that the dressing elements, which constitute the portions of the overall MWT system that cover and seal the wound, along with a portion of the tubing, when tubing is a part of the dressing embodiment as well as any incorporated functional or adjuvant elements described herein, are present as a single composite unit through fabrication and packaging. This description is used to clearly delineate this novel concept of a wound dressing capable of providing NPWT from conventional NPWT dressings, which all require some sort of assembly of the dressing at the time of application. The "one-piece" design described herein affords a clear clinical advantage over conventional "piecemeal" dressings. The current inventors are also the first describe a novel form of pulsed irrigation, which can be applied either via positive pressure pumping action (mechanical or manual) or by reverse lavage, which is a novel method for irrigating and cleansing a wound under a closed dressing system. Previous art and devices describe or contain elements of an irrigation system, which are not discrete, but rather joined proximal to the wound dressing and/or wound surface. This design flaw prohibits lavage irrigation, in which bursts of vacuum and irrigation run simultaneously or near-simultaneously under the control of the programmable electronic vacuum regulator. Conventional art that shares tubing or other forms of flow-path between vacuum (out-flow) and irrigation (in-flow) cannot provide this mode of wound cleansing. Conventional systems typically deliver irrigant to the dorsal surface of the dressing and not directly to the wound surface. This design drawback further makes lavage irrigation impossible for conventional devices, which "instill" irrigant to the surface of the dressing not facing the wound, and allow or hope for irrigant to soak through the dressing material to reach the underlying wound. This method only ensures wetting of the wound filler, which does not replicate the elements of irrigation used currently in open surgical procedures. Then at some determined time interval later, the instilled irrigant can be suctioned from the sealed dressing/wound. Thus conventional art describes a method of instilling irrigation fluid to a wound bed, which is suboptimal.

In contrast to conventional designs, various embodiments disclosed herein are unique in the delivery of the irrigant and the pathway the irrigant must travel to reach the completely separate vacuum circuit. Irrigant is typically delivered directly to the periphery of the wound. By doing this, the irrigant is forced to travel across the wound surface to reach the vacuum portion of the system which is located in the central aspect of the dressing. Without direct delivery of the irrigant to the periphery, the irrigant will follow the path of least resistance, which is generally a direct route back to the vacuum source. Additionally, under the reverse pulse lavage mechanism, the driving force behind the irrigation is not a positive injecting force, which can allow for pooling and compromise of the airtight seal, instead irrigate is pulled in a controlled fashion by bursts of negative pressure from the vacuum circuit. By allowing suction to drive the delivery of the irrigant with short pulses of negative pressure, the irrigant is unlikely to pool and compromise the seal at the periphery of the dressing. The current inventors describe a novel irrigation delivery method for ensuring the entire wound is irrigated while also limiting the potential detrimental effects of allowing irrigant to pool and compromise the seal.

The current inventors describe a distinctly different composite dressing, that is formed from several elements, which represents a nonobvious, useful improvement over the conventional art, in terms of manufacturing cost and simplicity of application and use. Further, there is a clinical benefit over conventional art that describes a channeled solid member dressing construction, which limits communication between the wound surface and the dorsal vacuum port, leaving intervening portions of the wound surface to be directly apposed/effaced by the solid portion of the dressing member, as opposed to the current inventors design, in which the porous dressing maintains dead space between functional elements of the dressing by affixing the functional elements to mesh or similar material, typically in a layered construction that provides a plethora of flow-paths between the wound surface and vacuum interface, regardless of whether an irrigation element is present or absent. These open (dead) spaces are also clinically advantageous, as the dead space within the volume of the dressing, is a space into which the dressing can collapse upon itself as the wound is progressively approximated by additional modules of this MWT system or under the normal contractile nature of some wounds. Solid members that are noncompressible are generally avoided in MWT-wound approximation. Further, the noncompressible nature of a solid member, may serve to focus excessive and even harmful pressure at a specific point of the wound bed, leading to pressure-related tissue injury.

In undulating wound beds the constrained geometric properties of a solid three-dimensional dressing member serve to limit the ability of the material to conform to the random, irregular geometry of the wound bed. The current inventors describe a layered dressing, single layer dressing or unidirectional wound filler based dressing, which overcomes this design constraint, allowing it to be sufficiently thin and pliable to match the undulations in wounds. The thinness of the layering/netting material described herein is limited solely by the material properties needed to maintain the basic MWT design (measurable in tenths of millimeters), while the thinness of a solid member design is limited by the minimally acceptable channel depth needed to ensure unblocked communication of wound effluent and the vacuum port and/or irrigation port and wound bed (measured in several millimeters). That less ideal design imposes a functionally significant Third dimension which substantially changes the mechanical properties of the dressing in a fashion that is disadvantageous to the application of NPWT and inconsistent with the tenets of MWT.

The irrigation tubing system described herein also overcomes limitations in the conventional art by using a mesh or similar material to layer the dressing. This layering allows for the functional elements (vacuum interface, irrigation tubing, accessory tubes, monitors, adjuvant therapy delivery mechanisms) to be placed and maintained in specific spatial relation to one and another. The elements are affixed to the layers of the dressing though a process of annealing, weaving or other mechanism of fixation. This controlled geometry ensures the elements are in the intended location to provide therapy. Further, the mesh-layering or tube-netting technique provides this crucial feature, while still preserving free space between the functional elements, so as to not block flow paths that are blocked by a solid member construction or coagulable fluid laden sponge-like wound filling material. Further, the irrigation tubing system described herein delivers the irrigant at gravity in-flow pressure or greater directly to the wound surface, typically at the periphery.

The unique configuration of this dressing provides the greatest assurance that all segments of the wound receive directed irrigation and that the flow path of the irrigant and wound debris it frees is directed from peripheral to the central. This later path of cleansing best replicates the current best practice for performing open surgical debridement/cleansing of wounds, in which the periphery is approached first and the cleansing process progresses centrally from there. In addition, the tubing described herein, as opposed to channels or other incomplete passageways or conduits, provide an enclosed space that allows for specified interaction between the dressing and wound. In the typical embodiment, perforations in the irrigation tubing system are only placed in the peripheral most extent of the tubing, so that the flow path of irrigant is from the centrally located irrigation central connection point, through the nonperforated central portions of the irrigation tubing to the perforated peripheral portions. In addition, the central location of the irrigation central connection point, is crucial to the customizability of this dressing, as the peripheral portions of the dressing can be cut to size from any margin of the dressing, to match the contours of the wound without impacting the irrigation or vacuum delivery systems.

It is the unique tubular and unified design described herein that directs irrigation to the entire wound bed, a feature not found in conventional systems. Under the lavage mode of irrigation, vacuum can be applied simultaneously. If the irrigant were not released peripherally, then the areas of the wound peripheral to the irrigation delivery point would likely not receive irrigant, especially in a lavage mode, as the flow path would be central, not centripetal. The specialized dedicated irrigation tubing system described herein, not only effectively delivers irrigation fluid to the wound surface, the "smart dressing" system also allows the end-user to customize the mode and timing of delivery of vacuum and irrigation (gravity flow, positive pressure, lavage, reverse lavage) to provide an ideal synchronization of vacuum and irrigation modalities to treat the wound.

The basic MWT dressing is a "smart dressing" in that it actively monitors the wound and can tailor care via pre-specified or end-user custom algorithms to most effectively treat specific wounds. The basic MWT dressing incorporates elements of wound care in addition to negative pressure, in a choreographed fashion. MWT and "smart dressing" are two linked novel concepts among the various innovative embodiments disclosed herein.

Further, the spatial relationship and flow-paths maintained and created by the layered dressing construct, allows this irrigation to synergize with the other cleansing elements of the wound dressing, like the abrasive wound facing surface, micro-motion from the positive pressure bladder and adjuvants (such as ultrasonic agitation) all working to loosen/free undesired surface material from the wound that is then washed away from the wound surface and removed via the vacuum system, which is located dorsal and centrally to the wound and irrigation system to set a specific flow path for debrided material away from the wound surface. The fixation of mesh-layers to functional elements in a "sandwich" fashion with a dorsal most impervious layer, leads to a single composite dressing that contains all elements of the novel mechanical wound therapy method in a single dressing, that is ready to be cut to the size of the wound and sealed to the wound margins to affect a closed system straight from the packaging.

While the MWT concept includes aspects of care that are contained in NPWT system in a segregated manner, these parts are part of an overall integrated system in the MWT. This integrated treatment of MWT provides benefits not available using simple NPWT. For example, without MWT's approach of integrating these additions into a single system, the dressing typically cannot remain in place on the wound for prolonged periods, for example, for periods as long as 48 to 72 hours, or longer. Further, by using MWT the dressing acts to cleanse the wound, thereby reducing the need for additional surgical debridement and/or reducing risk of infectious complication. Moreover, the dressing in conventional NPWT systems on its own only minimally, if at all, contributes towards directly reducing the dimensions of the wound, and these conventional dressing cannot provide wound monitoring. These elements are not attainable in any other fashion than through the integration of the various embodiments disclosed herein.

BRIEF DESCRIPTION OF THE DRAWINGS

The accompanying drawings, which are incorporated in and constitute part of the specification, illustrate various embodiments of the invention. Together with the general description, the drawings aid in explaining principles of the invention.

FIGS. 1A-C depict an exemplary embodiment of the layered dressing;

DETAILED DESCRIPTION

The present inventors recognized that the management of open wounds from trauma or disease, with the assistance of NPWT, benefits from the application of multiple features of the embodiments disclosed herein. From the time the wound is created it is beneficial if several interim activities occur prior to the final step in wound care, definitive soft tissue management. These interim activities include irrigation and debridement, minimization of microbial load, monitoring of the wound and sequential approximation of the wound—that is, closing of the wound—to the extent possible.

Typically, it is recognized that a wound care system cannot act completely independent of provider directed wound care. Surgical irrigation, gross wound decontamination, and debridement will remain the hallmarks of initial wound care in the foreseeable future. However, the present inventors recognized a number of improvements that aid in the development of a robust MWT integrated systems. Various embodiments disclosed herein serve to improve patient care from the time an adequate irrigation and debridement of the wound is completed until the wound is ready for delayed primary closure, skin graft, or other means of definitive reconstruction.

Figure 1A:
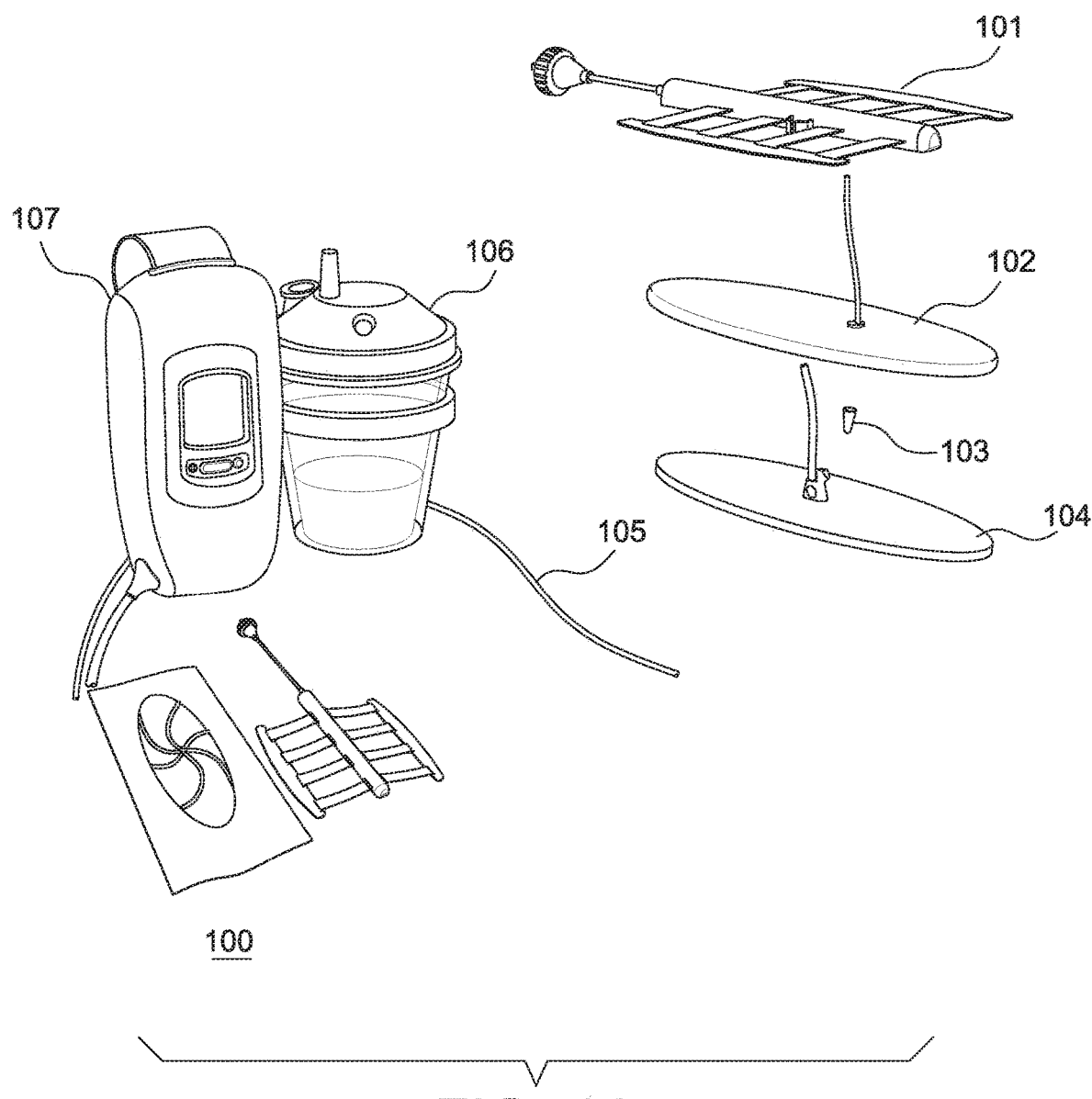

FIG. 1A depicts a composite "smart dressing" embodiment of the unified MWT system. This embodiment demonstrates a layered "smart dressing" with overlying modular components, including a wound approximating device 101, a positive pressure bladder 102, an irrigation accessory port 103, a SAWS MWT dressing 104, a vacuum line 105, a collection canister 106, and a programmable electronic vacuum regulator (EVR) 107. These components are described in further detail, in passages throughout this specification.

The composite smart dressing serves as a fully integrated wound care system that incorporates the benefits of NPWT along with other basic tenets of wound care. As such, the composite smart dressing is advantageous over conventional vacuum assisted wound care related devices which fail to make the leap forward from providing part of wound care to complete wound care. The present inventors developed the mechanical wound therapy (MWT) system to aid in all aspects of complete wound care. Additionally, the present inventors describe unique and novel improvements in each element of the MWT system. This next generation concept in wound care incorporates a number of beneficial elements into an integrated system, in which the whole tends to be greater than the sum of the individual parts. The use of the MWT concept for treatment of each unique wound begins with a basic MWT dressing, described below. The MWT dressing is configured to have a series of integrated modular components fitted upon it. The modularity of the system allows the healthcare provider to fine-tune the MWT to each unique wound and specific patient situation.

The inventors recognized a number of drawbacks in the conventional approach of cutting pieces of wound filler material to the shape and contour of the wound. For example, at the microscopic level, cutting a conventional open cell foam wound filler can lead to the formation of dangling free ends. Such free ends sometimes adhere to the wound surface and remain in the wound. If left in the wound these particles can act as nidi for infection and/or inflammatory response. In addition, the piecemeal approach of conventional wound dressings allows for the potential of retaining entire pieces of the wound filler in deep areas of the wound since the wound filler pieces are placed in the wound in a manner free and separate from each other.

Some conventional dressings employ an open-cell foam wound filler having pores in the foam which facilitate tissue in-growth. This can lead to gross retention of sponge particles, pain, bleeding and damage to the wound bed tissue at serial dressing changes, which tend to be more frequent with conventional systems (<72 hrs) than for wounds treated by the MWT concept disclosed herein. Likewise, conventional wound screens or fillers that are unnecessarily thick can become congested with coagulable fluids (e.g., blood, exudate) which act to clog the wound filler layer in specific regions, or even globally. This can effectively block the transmission of fluids across the coagulated areas. A regional dressing failure such as this may cause infections and/or poor wound healing in areas of the wound underlying these clogged areas of the dressing. The above mentioned limitations of conventional piecemeal wound dressings and non-ideal wound filling material apply to various known implementations of conventional NPWT devices, not solely to those using open-cell foam.

A shared limitation of conventional NPWT art is that wounds are "filled" with nonporous (e.g., silicon members) or porous materials (which can become less porous or nonporous through compaction and coagulation) that occupy space between the wound bed and functional elements of the dressing, like the vacuum source, irrigation and/or other modalities. This space occupying effect, is unnecessary to the clinical application of NPWT and instead limits the efficacy of the conventional art, by requiring space-occupying material to be placed between the wound surface and vacuum source or other functional elements. This material can become clotted with coagulable wound effluent, blocked by some other means, or in some instances, may be an impediment to flow by design (e.g., silicone members with channeled passageways). In this fashion, conventional wound fillers may represent a limitation to the optimal application of NPWT and MWT.

The embodiments disclosed herein provide a novel solution that overcomes this limitation. Elimination of space occupying wound filler, also enables another important innovation described herein. Specifically, the wound approximating feature of MWT is facilitated by a basic MWT dressing that can compress/fold on itself as the wound margins are progressively approximated. The wound filling material disclosed in conventional art, can act to resist this contractive force. The layered composite technique disclosed herein overcomes this limitation. Additionally, the layered structure will allow for structural integrity of the dressing which may be attached to the skin edges to prevent movement of the dressing or even used to prevent skin retraction itself.

Returning to FIG. 1A, this figure depicts an embodiment of a unified layered dressing for application of MWT. Various unified dressing structure embodiments disclosed herein overcome drawbacks of conventional piecemeal cut-to-fit wound fillers through improvements in the structure and design of the wound screen/filler, elements of the irrigation/vacuum delivery and the basic design of the vacuum/irrigation functions. The dressing structure of the various embodiments is "unified" inasmuch as its components are fixedly attached together. The unified dressing structure is configured to be placed over a wound as a single composite unit with all the components remaining fixedly attached together, rather than being placed on the wound in a piecemeal manner as is done with conventional systems. One of the advantages of this unified design, is that it improves upon a significant drawback of conventional systems that use piecemeal cut-to-fit wound fillers, by preventing or reducing the potential for remnants of the dressing to remain in the wound when the dressing is removed. By "fixedly attached" it is meant that the components are attached together or otherwise connected in a manner sufficient to allow the fixedly attached components to be handled and positioned as a unit. In some embodiments the fixedly attached components are permanently fixedly attached and may not be disassembled without breaking or deforming them. In other embodiments the fixedly attached components may be disassembled by unscrewing, unsnapping, or otherwise unfastening the mechanical means used to hold them together.

Additional embodiments of the basic MWT dressing will have higher functionality incorporating monitoring and other technology. The unified design allows for a simplified, integrated housing for wires (when wireless technology is not used) that connect wound surface level technology with the programmable electronic vacuum regulator. This feature is exclusive to a unified design, and not reproducible in by current art which call for piecemeal construction of the dressing. The specific placement of components at fabrication of the MWT dressing allows for the computation (in the EVR) of spatial information, like regional leak detection or wound health. Conventional art does not describe a similar means for establishing and maintaining specific position of functional elements within the dressing.

FIGS. 1B-1C depict embodiments of a basic MWT dressing, demonstrating layered dressings and the elements within this example of a unified layered dressing. FIG. 1B depicts an exemplary embodiment of the layered dressing. FIG. 1C depicts an expanded view of FIG. 1B, showing various components of the embodiment. The unified layered dressing embodiment of FIG. 1C includes an irrigation connection tubing 108, which conducts irrigant in an antegrade fashion from the irrigation source (e.g., 1 liter IV bag or fluid pump) to the dressing and wound surface. The irrigation connection tubing 108 connects the irrigation source to the dorsal surface of the dressing at the tubing connection point. A vacuum connection tubing 109 conducts wound effluent retrograde from the wound to a collection canister (e.g., the collection canister 106 of FIG. 1A). The vacuum connection tubing 109 connects the dressing (at the dorsal surface, via the tubing connection point) and the collection canister. A wound pressure sensor cable 110 may be implemented as an insulated, medical grade wire that connects the wound pressure sensor 119 which is located at or near the surface of the wound to the electronic vacuum regulator, where the information is interpreted, integrated and displayable on a display screen. The wound pressure sensor 119 provides direct measurement of the therapeutic negative pressure reaching the wound surface, as opposed to indirect pressure measurements obtained more distal (e.g. farther retrograde along the vacuum tubing system from the wound surface) from the wound surface in conventional systems.

With regards to size, the tubing described herein for the dressing embodiments may be approximately 1-3 mm in inner diameter and 3-5 mm in outer diameter. The mesh layers typically allow for openings from 1-5 mm in width. The tubing is fabricated from a soft, pliable biologically inert material. The depth or thickness of each layer of the layering material in the various dressing embodiments is typically 0.5 to 1.5 mm in thickness. Therefore, a layered dressing with a tubing system (e.g. irrigation tubing system described herein) incorporated is roughly 3-10 mm in depth or thickness.

The size (or area) and shape (e.g. circular, elliptical . . . ) of the dressing can vary based on the function or location of use. In general the dressing will be larger in size than the wound it is intended to treat, allowing it to be trimmed to size to match the unique contours of the wound. The dressing can be packaged in different sizes such as large (e.g. 12 inches in long axis or diameter), medium (e.g. 6 inches) and small (e.g. 3 inches). Dressing size and shape options are numerous, as special dressings can be designed for specific uses, such as a fasciotomy performed for acute compartment syndrome in which the dressing is more elliptical (e.g. 12 inches×6 inches).

The embodiments depicted in FIGS. 1 A-C may feature one or more layers of pliable layering material such as the layer 113, a dorsal most sealing layer 111 (sometimes called a cover component or covering layer), which may have an apron-like extension 112 beyond the dimensions of the layered dressing, a ventral layer 117, a vacuum connection tubing 109, irrigation connection tubing 108, an accessory port 123 may be present in the irrigation tubing 108 or vacuum connection tubing 109. The accessory port 123 can be directly accessed, for example, via a Luer lock syringe. The accessory port 123 can be used to directly input smaller volumes of irrigant under manual control. A typical use is for the delivery of medicinal or antiseptic irrigation fluids.

FIGS. 1 B-C depict the accessory port 123 (sometimes called a provider access port) configured within irrigation connection tubing 108. In a similar fashion, in some embodiments an accessory vacuum port 108 may be may be configured within the vacuum connection tubing 109 to allow sampling of the wound effluent and/or a means for clearing a blockage from the vacuum connection tubing 109 or its tubing connection point. The accessory port 123 along the irrigation system may be present in some embodiments of the device which allows the provider to directly infuse irrigant onto the wound, with the vacuum source on or off at the time of infusion. Similarly a vacuum access port can be constructed in the vacuum connection tubing, to allow sampling of the wound effluent. Moreover, the irrigation therapy of various MWT embodiments can be implemented in the patient's hospital bed, in an out-patient setting, or other environments conducive to patient care.

An airtight sealing layer 111 (sometimes called a cover component or covering layer) is typically affixed to or constitutes the dorsal most layer of a layered dressing. This layer is composed of airtight material, such as plastic film. It may be a layer of material, or an airtight material that is sprayed or otherwise applied onto the remaining dressing. The application of this layer typically occurs at manufacturing. In some embodiments an additional thin flexible adhesive layer may be affixed to the outside of the airtight sealing layer, conforming to its shape. Since such an additional layer is added to the sealing layer 111 and conforms to its shape, the airtight sealing layer 111 is still considered the dorsal most layer of the dressing assembly. The sealing layer 111 can be fixedly attached across the entire dorsal surface of the dressing, attached only in certain points, or it may be free from attachments to the dorsal surface of the remaining layered dressing aside from a central connection to the tubing connection point. The "dorsal" surface is the surface furthest away from the wound. In embodiments in which the sealing layer 111 is not fixedly attached to the remaining layered dressing through fabrication, an adhesive can be placed with peel-away paper backing on the ventral surface of the sealing layer 111. The "ventral" surface is the surface facing the wound. This allows for the sealing layer 111 to be sealed to the remaining dressing at the time of placement into the wound or immediately after or prior. Sealing layers in this embodiment can be completely free of the dressing or connected centrally to the tubing connection point. For those implementations that are completely free of the dressing, the sealing layer 111 takes on properties and functions similar to an adhesive sealing sheet. In some embodiments, a dorsal sealing layer is permanently affixed (e.g. a spray on coating similar to Flex Seal™) to the dorsal most surface of the layered dressing, typically at fabrication, upon which an additional sealing layer with or without central connection to the tubing connection point can be present. The advantage of this embodiment is that an immediate airtight, fluid tight sealing layer is present on the unified layered dressing at application to the wound, to reduce or eliminate wetting of the dorsal surface of the dressing and thereby facilitate good removable fixation of the non-affixed sealing layer (e.g. the more dorsal airtight sealing layer in this embodiment) to the dressing and possibly adjacent skin margins (e.g. the apron embodiment described below).

An apron 112 can be provided around the outside edge of sealing layer 111. In some embodiments the apron 112 is a lateral extension of the sealing layer 112, while in other embodiments the apron 112 overlaps the sealing layer 112. Other embodiments are apronless. As depicted in FIGS. 1 B-C the apron 112 is an extension of the sealing (dorsal most) layer 111 beyond the dimensions of the remaining layers of the layered dressing. The apron 112 is typically composed of the same material as the sealing layer. In typical embodiments the sealing layer is a thin plastic film, and the apron is an extension of this film beyond the borders of the remaining layered dressing. The apron 112 can have an adhesive with peel-away paper backing on the ventral surface or it may be adhesive free. In embodiments where there is an adhesive on the apron 112, the apron 112 removably affixes itself, and thereby the dressing to which it is integrally connected, to the skin at the margins of the wound. The durability of the attachment—that is, the strength of the bond with which it is affixed—may be enhanced with placement of additional adhesive sealing sheets or agents. In embodiments without adhesive on the ventral surface of the apron 112, a tacky, weak adhesive substance, similar to Post-It Note™ adhesive can be present on the dorsal surface, with or without peel-away paper backing in place. A "weak adhesive", sometimes called a "semi-adhesive," is tacky enough to supplement adhesion of adhesive sealing sheets between the dressing and the patient's skin. This serves as a means for enhancing adhesion between the adhesive sealing sheets and the dressing and the patient's skin. The result of this effect is to create an airtight sealed wound, as well as to support NPWT and the other functions conducted under MWT.

Various embodiments feature a vacuum interface chamber 121 (Alternatively, in embodiments in which the vacuum interface has no ventral floor, this component may be termed the Vacuum Interface Flange). The vacuum interface chamber 121 is the point that connects the vacuum connection tubing from the regulated vacuum source to the sealed dressing. In this way, the wound fluid communicates from the sealed portion of the wound through the vacuum interface chamber and ultimately to the collection canister via the vacuum connection tubing. The vacuum interface chamber 121 is typically made from a soft medical grade plastic (e.g. Silastic) that encloses a specified volume of space within a predetermined height and circumference of the plastic walls, e.g., 2 cc to 50 cc. The end result is a closed cell with one or more access ports and perforations. In at least one embodiment there is one main port on the dorsal surface (the single perforation in the dorsal surface of the chamber), which is the tubing connection point for the vacuum circuit. There are typically a number of perforations in the vacuum interface chamber 121 on the ventral (wound facing) surface and sometimes on the side surfaces, as well.

The tubing connection point may be configured as part of a vacuum interface chamber 121 where it can have a one-way valve that prevents back-flow of wound effluent. Thus, in this embodiment wound effluent can only progress retrograde from the wound once it cross the one-way valve in the tubing connection point and enters the vacuum connection tubing. The internal space of the vacuum interface chamber 121 is kept patent—that is, open to afford free passage—even under active application of negative pressure to the chamber 121 by its construction. This may be achieved by providing a wall thickness and material properties that prevent collapse of the chamber 121 under the therapeutic range of negative pressure (e.g., 0 to −250 mmHg) or by the placement of internal risers that prevent collapse. The overall appearance of the vacuum interface chamber 121 may be analogous to that of a shower head, with one main dorsal input and a multitude of flowpaths on the contralateral surface. This serves to better distribute the negative pressure to the entire wound. The multitude of perforations means that blockage of one or several of the perforations does not completely block fluidic connection between the wound and the vacuum connection tubing/vacuum source. This is a significant advantage over conventional systems that have a single primary flow path by which the vacuum circuit communicates with the sealed wound, which when block by saturated coagulated wound filler or other wound-related material, renders the conventional system non-functional. The vacuum connection tubing 109 is typically in fluidic communication with a collection canister (e.g., collection canister 106 of FIG. 1A). As such, the vacuum connection tubing 109 is configured so that fluids, either liquid or gas, can flow to the collection canister 106. The connection point for the vacuum connection tubing 109 is generally implemented on the vacuum interface chamber 121, or flange.

Layer 113 of FIG. 1C is an example of the layering material used in various embodiments. The ventral layer 117 may be constructed from the same material as layer 113, or from a different material, depending upon the requirements of the embodiment. Biologically inert materials such as plastic or a synthetic polymer can be used. Alternatively, the layer may have a central core material that is coated with a plastic or polymer film to provide specific properties, which may include non-stick, abrasive and cohesive properties. The cohesive property serves to link the central core fibers, to prevent or reduce fraying when the layer is cut to size. The thickness of the layers typically is in the range of 0.5 mm to 3 mm. The layer 113 may be composed of mesh, netting and/or thin perforated film. In many embodiments—for example, unified layered dressing embodiment—the layering material of the layer 113 is fixedly attached to the other components of the dressing structure. For example, the layer 113 may be fixedly attached centrally through manufacture to the vacuum interface chamber 121 (or flange). The mesh or netting layer 113, or other layers in the assembly, may be configured to maintain the spatial relationship of the other dressing components. In some embodiments the mesh layer (e.g., layer 113) may be permanently affixed to the other functional elements of the dressing assembly. Depending upon the implementation, the layer 113 may either be fixedly attached, or not fixedly attached, to the overlying sealing layer 112. The overlying sealing layer 112 is typically fixedly attached to the underlying dorsal surface of functional elements (e.g., irrigation tubing system) and/or spacers, either by direct attachment or by attachment via another element such as the vacuum interface chamber 121 and/or a dorsal layer of the layering material. The layer 113 is one of the basic elements of the layered dressing assembly.

The mesh, netting and/or thin perforated film layer of the various layer 113 are generally constructed from a pliable material that may be covered with a sealing or bonding material. The construction of this layer material is specified to aid in eliminating the potential for fraying or dangling free ends which can allow dressing material to incidentally be left in the wound bed at dressing changes—a drawback of conventional systems that could propagate infection or inflammation and lead to less favorable wound healing.

Typically, the layers of the layered dressing assembly are affixed together so they can be applied over a wound as a single unit. In various embodiments, a layer—e.g., the layer 113—need not be directly attached to the next most ventral layer, but rather may be affixed indirectly through shared fixed connections to the functional elements and/or spacers between that layer and the next. In these embodiments one or more passageways may be formed by layering flat sheets of mesh, netting or thin perforated film, all of which are pliable material with multiple open spaces or perforations of homogenous or heterogeneous area, that are interspaced with functional elements of the MWT system or spacers.

In FIGS. 1 B-C irrigation tubing layer 115 is an example of a geometric arrangement of the irrigation tubing system. The configuration of irrigation tubing layer 115 depicted in FIGS. 1 B-C has a spiderweb-like appearance, containing both radial arms and horizontal traversing connectors. In other embodiments, there are only radial arms. In many embodiments the irrigation tubing system has a central connection point to all irrigation tubes that communicates to the wound surface and ultimately connects to the irrigation source. This occurs through a wound-side irrigation connection tubing. This tube connects from the central connection point of the irrigation tubing system to the tubing connection point for the irrigation circuit at the dorsal surface of the unified dressing, where it connects to the irrigation connection tubing, as described for irrigation connection tubing 108 above. The irrigation tubing layer 115 typically is devoid of perforations for the majority of its initial flow-path length from the central connection point outward. At a specific, more peripheral length (e.g., 3 cm from the central connection point)—which may vary from prefabricated dressing size to dressing size (e.g. small size dressing versus large size dressing)—perforations in the ventral and lateral surfaces of the tubes, but not the dorsal surface, typically of a diameter equivalent to the inner diameter of the irrigation tubing system tubes occur. In at least one embodiment there are no perforations along the length of the tubes. Instead, the distal ends of the tubes are open, to allow irrigant to flow directly to the periphery of the wound. The tubing system may be composed of a soft, pliable medical grade plastic and has material properties that most closely resemble those of closed suction drainage tubes used currently (e.g., Jackson Pratt 7-French round drain). Due to the central connection point and radial orientation of the tubing system, the periphery of the irrigation tubing layer 115 can be cut at any point, without disturbing flow across the entire irrigation tubing system. This allows the system and the dressing in which it is fixedly contained to be custom cut to fit the shape of the wound being treated.

Ventral layer 117 is the layer that is most ventral, that is, closest to the wound. Ventral layer 117 is typically another layer composed of mesh, netting and/or thin perforated film layering material. This specific layer typically has special qualities as it is the ventral-most layer, and therefore the layer directly apposed to the wound. In some embodiments the ventral side of the ventral layer 117 is configured to have an abrasive finish or surface. The abrasive surface works in conjunction with other elements of the MWT system to produce micro-abrasion and micro-debridement at the wound surface. In other specialized embodiments, the ventral surface of ventral layer 117 may be configured to have a very slick (low coefficient of friction, nonstick) surface which can be made devoid of pores or other points of attachment for microbes, especially those most likely to form bio-films. This embodiment tends to reduce adhesion of the dressing to the underlying tissues, ideal for when the dressing is placed over skin grafts or other tenuous tissues, but it can generally be used in any type of wound. Like the next more dorsal layering material, the ventral-most layer is fixedly attached to the functional elements and/or spacers between them, at the ventral surface of these elements. It is typically not directly attached to the next more dorsal layering material.

The wound pressure sensor 119 is a negative pressure sensor positioned to sit at or near the wound surface. The wound pressure sensor 119 is typically affixed to the ventral, central surface of ventral layer 117. In some embodiments, the wound pressure sensor may be excluded. In other embodiments, described below, there are multiple wound pressure sensors.

Figure 1D:
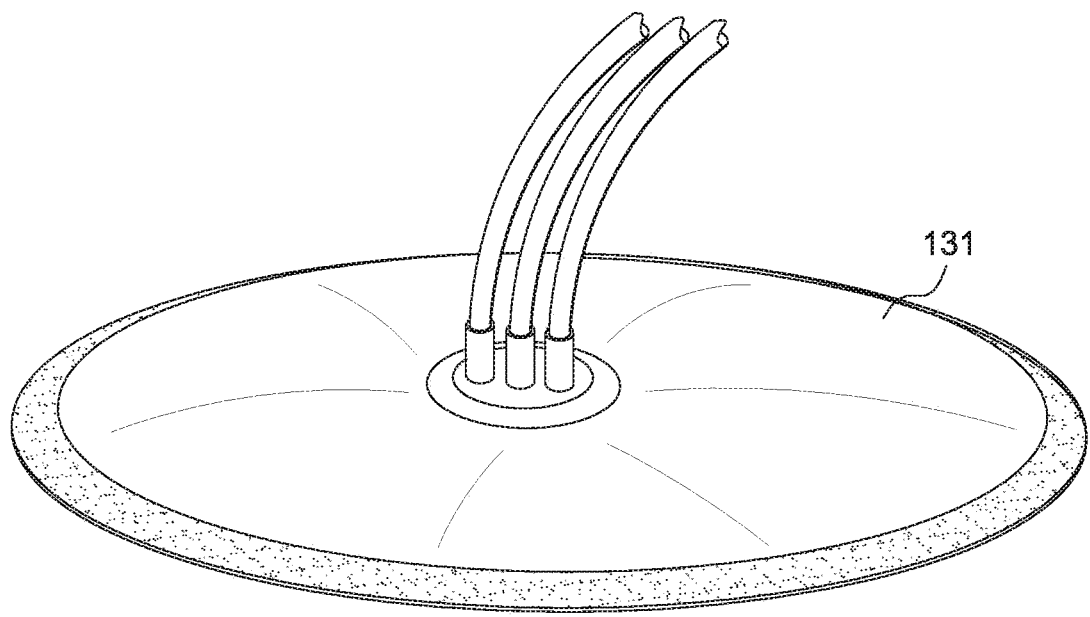
FIG. 1D depicts the dorsal surface of an exemplary layered basic MWT dressing which has been sealed to the wound.

FIG. 1D depicts the dorsal surface of an exemplary layered basic MWT dressing which has been sealed to the wound. The tubing connection point is seen centrally with the vacuum and irrigation connection tubing and the wound pressure sensor cable seen entering this connection point and the underlying sealed dressing.

Figure 1E:
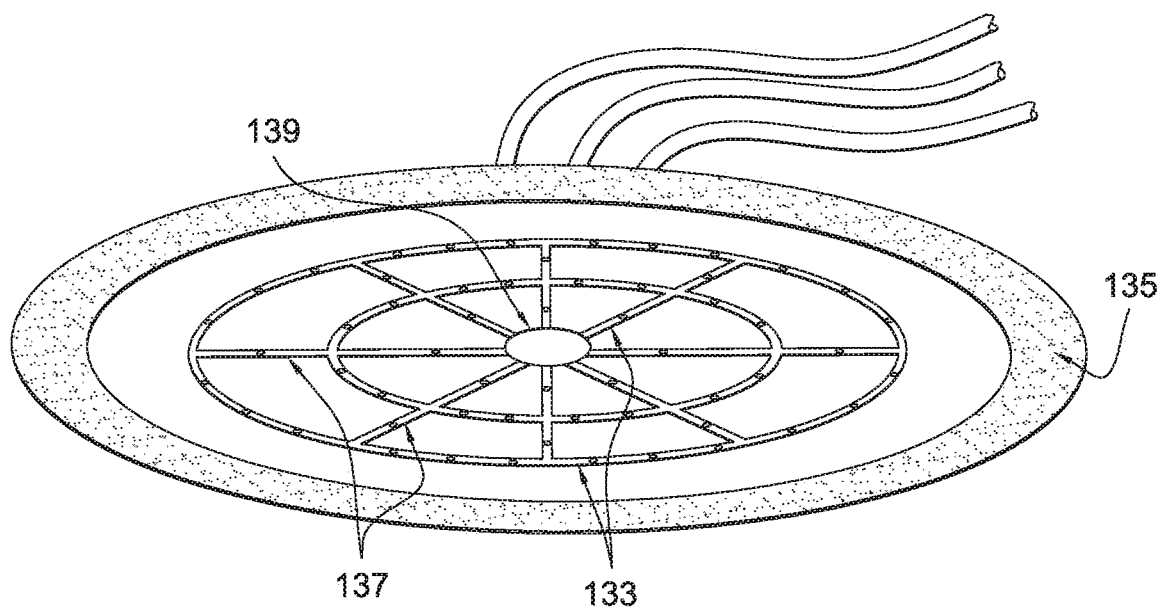
FIG. 1E depicts the ventral surface of an exemplary layered basic MWT dressing taken from the perspective of the wound.

FIG. 1E depicts the ventral surface of an exemplary unified layered dressing embodiment, which can also be referred to as a basic MWT dressing. The view of FIG. I E is taken from the perspective of the wound looking outward, from underneath the dressing. The ventral facing perforations in the irrigation tubing system are seen in the spiderweb embodiment of the irrigation tubing system. This tubing system 133 and 137 sits affixed to the ventral most layering material. The central connection point 139 is the central point at which the radial tubes 137 of the irrigation tubing system come together. It typically does not have perforations. In embodiments with a wound pressure sensor, it is typically positioned directly ventral to or inherent to the ventral surface of the central connection point of the irrigation tubing system. The hatched area 135 at the periphery, represents the ventral surface of the apron, which may or may not have adhesive.

The embodiments of FIGS. 1A-E have no wound filler per se, as that term is used today in regards to conventional systems with bits of sponge, gauze or nonporous dressing elements serving as wound filling material that are cut to fit the shape of the wound. Instead, the present embodiments feature layers of netting, mesh or thin perforated film configured, either with or without tubing systems. The term "mesh" in this context is intended to mean a screen-like material made of interwoven strands, e.g., metal strands, fiber strands, plastic strands, strands of other synthetic materials, or the like. "Netting" is a material with holes, or spaces, that allow fluids and gasses to pass through the netting. The term "netting" is a broader term than the term mesh. Netting in the present context encompasses the term mesh—that is, all types of mesh materials are netting, but certain types of netting materials are not considered meshes.

The term perforated film describes a material, typically having a constant thickness, which is very thin, typically 1-3 mm or less. At production of the thin perforated film, through casting, extrusion, stamping or other mode of fabrication, multiple perforations are made in the film that can be of the same or varying diameter and density, for example, as discussed above in conjunction with FIG. 1K. Inert materials such as plastic or a synthetic polymer can be used. In some embodiments, a textured surface can be fabricated into the ventral surface of the thin perforated film intended to be used as a ventral layer for a layered dressing embodiment or as the film used in a single layered dressing embodiment. This can be an abrasive texture for some indications and in other embodiments it can be very smooth or non-stick. Functional elements of the unified dressing pass above or below the perforated film, but typically not within the film. By contrast, in certain embodiments of the dressing using a mesh or netting layering material, the functional elements (e.g., irrigation tubing system 115) can be woven or otherwise incorporated into the mesh/netting material at fabrication.

To create depth, the layering of the unified layered dressing embodiment can be repeated multiple times as needed. While the ventral and dorsal layers most commonly have unique properties, the layering material used to construct central layers of a multi-layered dressing is typically uniform. In these multi-layered embodiments functional elements, such as the irrigation tubing system, are nonremovably affixed through fabrication to the layering material ventral and dorsal to the functional element. In multi-layered dressings, with a limited number of functional elements (e.g. only one tubing system) the intervening layers can be separated by plastic spacers. This pattern of layering material separated by functional elements or spacers can be repeated as many times as needed to create an intended final thickness and/or functionality of the dressing. In some embodiments supporting the adjuvant medical therapy or advanced monitoring modules described herein, vertical or multi-layer perforations or other means of alteration to the layered dressing construction can exist that for instance house elements of the adjuvant medical therapy module (e.g. ultrasound transducer) or permit passage of a device from the dorsal surface into a deeper (more ventral) layer of the dressing or all the way to the wound bed, while still maintaining an airtight seal over the wound.

Figure 1F:
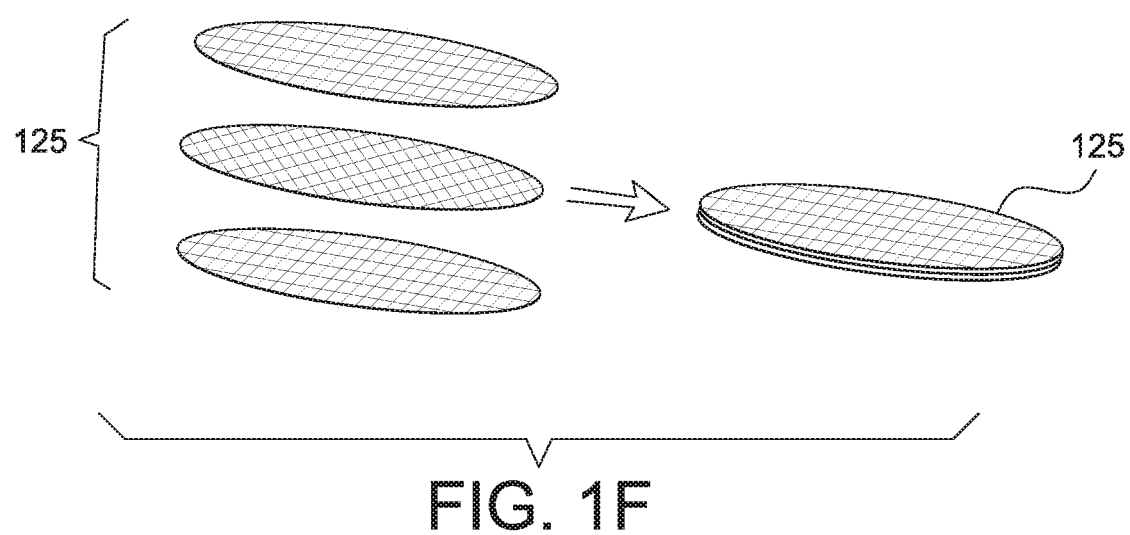
FIG. 1F depicts a multi-layered dressing with multiple layers of netting or mesh aligned in varying degrees of orientation.
Figure 1G:
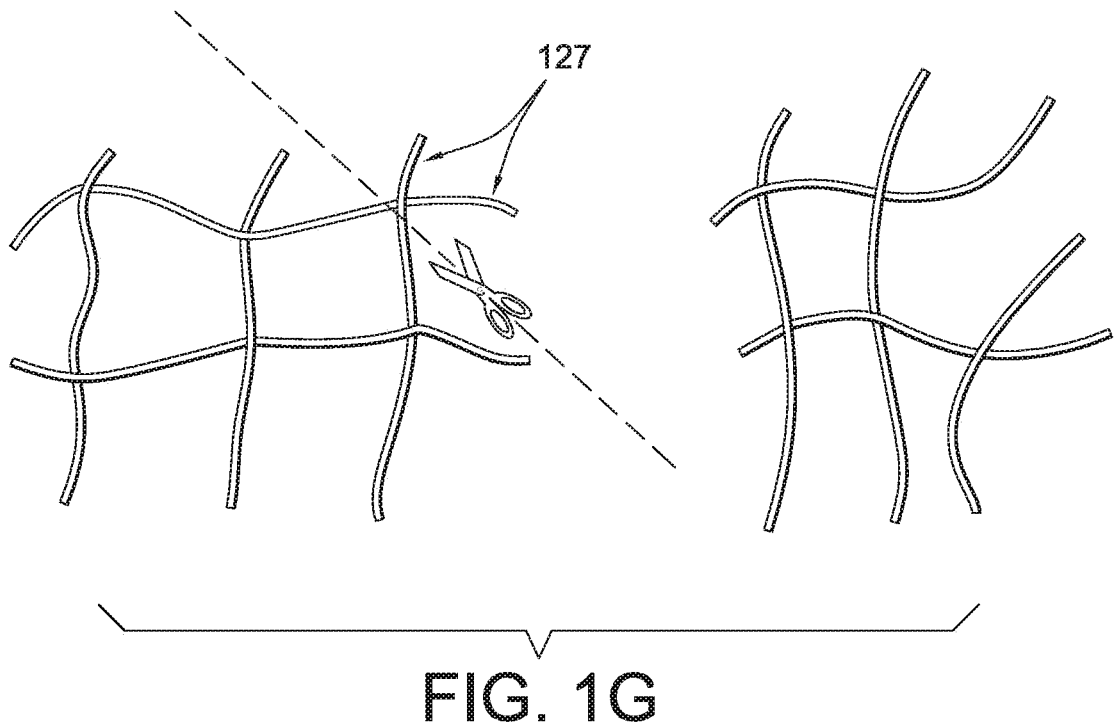
FIG. 1G depicts aspects of a woven structure.
Figure 1H:
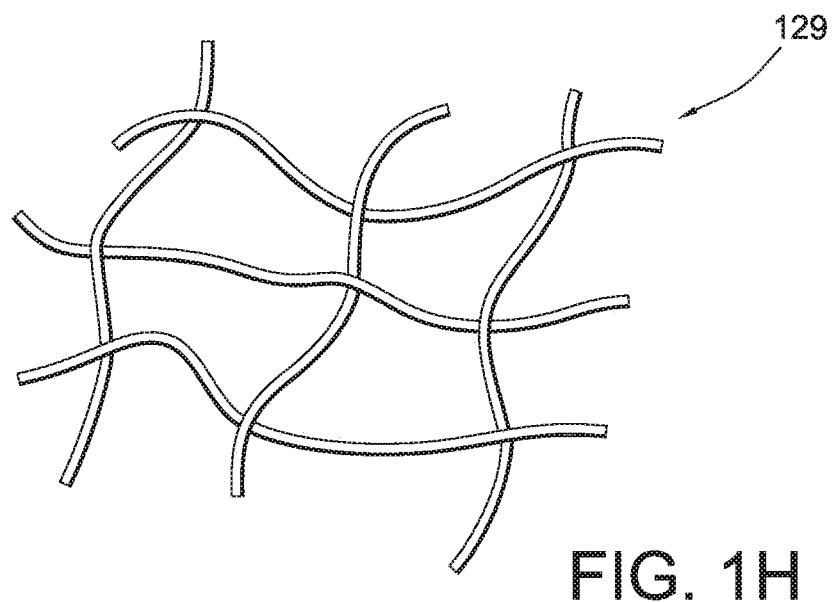
FIG. 1H depicts an uncoated woven structure.
Figure 1I:
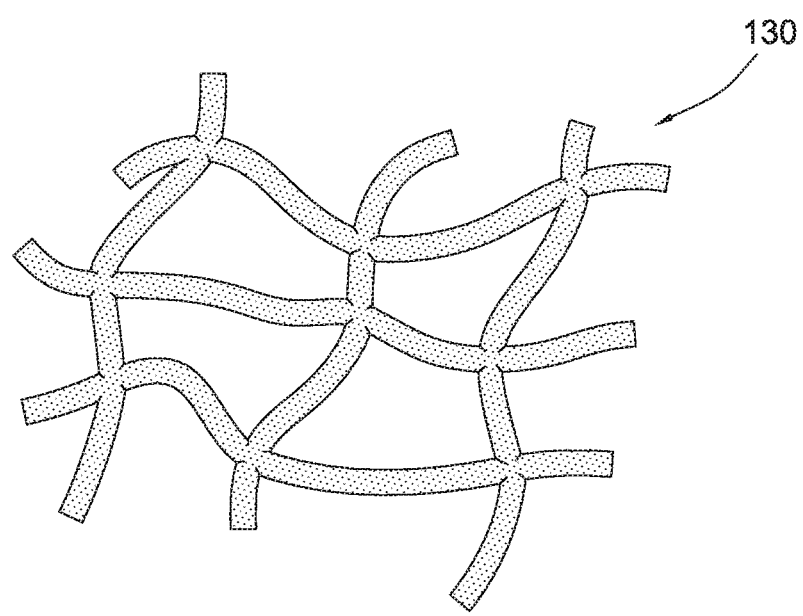
FIG. 1I depicts a coated woven structure.

FIG. 1F depicts an embodiment with multiple single layers 125 of netting, mesh or thin perforated film. These layers 125 are oriented in different manners to allow a series of channels that create a multi-layered dressing depicted on the right. By alternating the orientation of the layers 125 (e.g., rotating 45 degrees, as depicted, or by any amount more or less such as 60 degrees, 30 degrees, 15 degrees) the channels remain open to fluid and gas but are not straight channels that encourage deep tissue ingrowth. Additionally, the layers can be oriented in such a way that the holes do not line up perfectly on top of each other, thus reducing the size of the straight pathway in the vertical direction or even requiring fluid or gas to travel in a zigzag pathway to travel through the dressing in a vertical manner. The final product on the right can be either layered without permanent fixation so they can be separated easily or they can be permanently fixed so the product is a single composite structure made up of multiple layers.

By having multiple layers as well as holes in the netting, mesh or thin perforated film, fluid or gas can pass through the dressing along two axes. In this figure the fluid or gas can pass in a horizontal fashion between layers as well as the vertical axis through the holes or open spaces within the layering material. This layered structure facilitates fluid or gas passage without restriction through the structure in two different directions (horizontal and vertical).

FIG. 1 G depicts a woven structure in which the ends 127 of the mesh have been cut. In various embodiments the layering material will be woven as shown in FIG. 1G (or in some instances, non-woven) mesh that is constructed so as to eliminate or substantially prevent fraying, unraveling, or other events. This property will prevent dressing material from being retained in the wound at dressing change. Inert materials such as plastic or a synthetic polymer can be used. Alternatively, the woven layer may be a central fiber of some type that is coated with a plastic or polymer to prevent free particles when cutting to size. The thickness of the layers may be from 0.5 mm to 3 mm of depth. If the woven structure is not coated or sealed, the cut ends 127 allow for the woven structure to unravel or fray. It also allows for free ends to be created in the woven structure at corners or curves. These small fragments at a cut edge sometimes become dislodged from the woven structure in a wound dressing model and remain in the wound. Nonideal woven structure or open cell structure facilitates residual material being left in the wound by the dressing which can lead to inflammatory responses or nidi for infection.

FIG. 1 H depicts an uncoated woven structure 129. This structure is made up of multiple strands that are woven together to create a mesh type design. This design, if untreated, may produce small pieces or particles that are created when the woven material is cut, as shown on the left. Therefore, the application of a coating or bonding agent, as shown in the embodiment of FIG. 1I, is used to help prevent the creation of free pieces at the cut edge. By applying a coating to the woven material, the coating can bond all the stands into a single structure. This coating tends to prevent or reduce unraveling or fraying. The bonding or coating agent can provide a structural property that is not easily sheered to prevent the unwanted tearing of the layering material. To this end, biologically well-tolerated/inert or antimicrobial active coatings may be applied to commercially available mesh during the manufacturing process to prevent fraying, as a bonding or sealing layer. The coating may consist of, but is not limited to, pliable coating materials such as plastic, rubber, latex or medicinal preparations. Alternatively, thin pliable films may be used of specified thickness, perforation diameter and density as the layering material for the unified layered dressing. In the various embodiments of the layered dressing, the netting, mesh or thin perforated film layering material are configured to prevent unraveling by this or other means. This aids in preventing the incidental release of dressing materials that could be retained accidentally in the wound bed at dressing change.

Unintended retention of dressing material in the wound bed is a known drawback of current art. The novel layered dressing described herein overcomes this drawback by the specified construction of the layering material. The layering material is composed of matter possessing sufficient tensile strength to not break and/or release from the dressing proper under the conditions of normal use. In some cases the layering material is covered by a permanent sealing, coating or bonding film that prevents unraveling or otherwise releasing material from the dressing into the wound. Some embodiments feature a film that has anti-microbial properties through surface release of antibiotic/antiseptic agents and/or through material properties. One such material property is a surface that has ultra-high smoothness, devoid or limited in sites that support attachment of microbes. This aspect of the layering material aids in preventing or reducing the production of biofilms on the dressing. Further, the ultra-smooth surface increases the ease of release of the dressing from the wound surface at dressing changes, which reduces pain, bleeding and wound bed tissue trauma that occur with less ideal dressing materials used in conventional systems.

Various embodiments involve an all-in-one unified design, which is a single complete dressing that only needs to be cut to size and sealed to the wound margins with adhesive strips/film. Thus, in such embodiments the entire dressing is one single unit. This differs from the conventional art in which discrete layers or parts of dressing material and components are independently applied sequentially to create the final dressing. In addition to a single-unit design as opposed to a piecemeal design, some of the various embodiments disclosed herein further overcome the potential danger of retained gross fragments of the dressing material inherent to conventional systems by applying radio-opaque paint/material to key features of the dressing, like the tubing or certain areas of the netting. This radio-opaque paint/material can be applied such that incremental segmentation of known lengths (e.g., 1 cm markings) exists, that can be used to measure dimensions and to indicate whether tubing has been left in the wound. In some embodiments radio opaque markers are integrated in the various dressing components—that is, placed within the dressing components or otherwise attached to the dressing components—to allow them to be identified in case there is concern for retained dressing material in a wound. Therefore, in the undesirable situation in which dressing material is retained, use of these various embodiments generally enables retained portions of the dressing to be detected by simple fluoroscopy, radiography or possibly CT scan.

This next generation NPWT dressing concept marks an improvement over the conventional NPWT wound-filler based dressing types. The layering material—e.g., layers 113-117 of FIGS. 1 B-C—can serve multiple functions. For example, two such functions may be to serve as the substrate that provides form to the dressing and a fixation point to maintain specified spatial relationships between functional elements of the dressing.

Secondly, the mesh, netting and/or thin perforated film provide a multitude of flow-paths for suction and irrigant. By the construction of this layering material and its placement in the composite dressing, interspaced by functional elements of the dressing and/or spacers, flow-paths are created in the vertical and horizontal plane, as shown in FIG. I F, thus overcoming drawbacks of conventional dressings, in which flow paths are limited in number and random in pattern, both of which may increase the chance that segments of the wound filler develop blocked flow-paths.

Additionally, the dressing's inherent structural integrity allows the dressing to be attached to the skin edges and apply a force to the wound itself that tends to resist the wound's tendency to expand. It also allows for maintenance of position of the dressing and the contained functional elements within the dressing (e.g., irrigant tubing, pressure monitor, etc) over the wound.

A biodegradable layer may be used to in some embodiments to interface with the wound surface and prevent complications due to foreign matter being left behind. Possible materials to use are but not limited to Polyhydroxyalkanoate (PHA), Poly(lactic acid) (PLA), Polycaprolactone (Pere), Polyesteramide (PEA), Aromatic copolyesters (PBAT . . . ), Aliphatic copolyesters (PBSA . . . ), or Polyglycolide or Polyglycolic acid (PGA). The use of a biodegradable ventral layer can aid in avoiding tearing or otherwise disturbing a partially healed wound when the dressing structure is removed. When such a dressing is removed, the biodegradable layer can be snipped away at the edges or be expected to spontaneously release from the dressing proper, as hydrolysis or other biological or chemical effects occurring over the duration of wear of the dressing have weakened the integrity of the layer and/or its fixation to the remaining portions of the unified dressing. Under this embodiment, if part of the biodegradable layer (e.g., the ventral most layer) is left behind, it harmlessly absorbs into the patient's body. In some embodiments, this bioabsorbable layering material can be used as the layering material for all layers in the unified dressing.

Figure 1J:
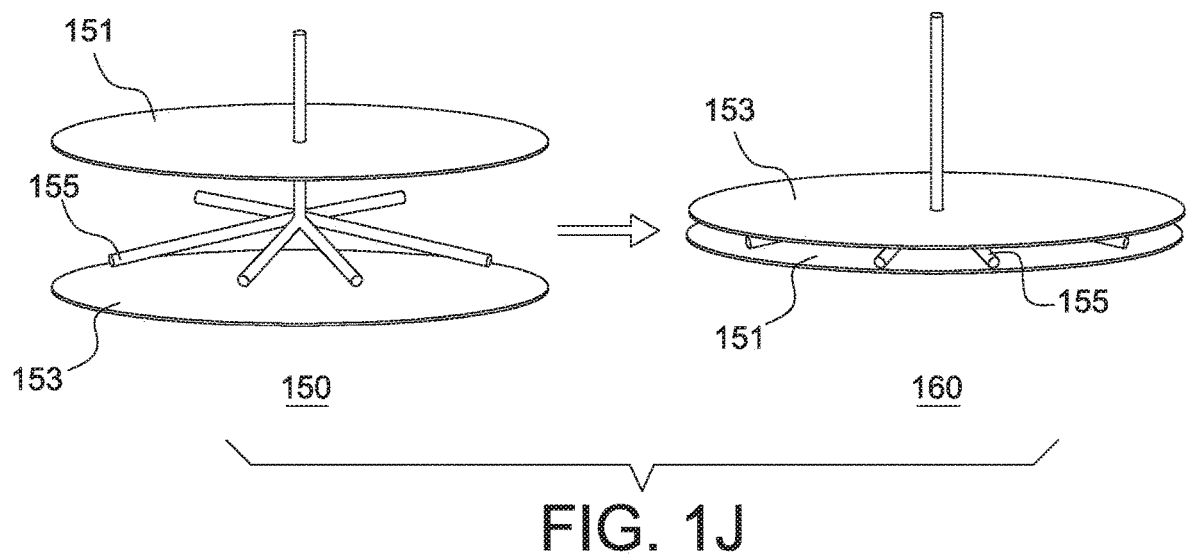
FIG. 1J depicts a system where tubing structures designed to allow passage of fluid or gas are spacially aligned in a specific manner.

FIG. 1J depicts an expanded view 150 of an embodiment with tubing structures designed to allow passage of fluid or gas are spacially aligned in a specific manner. Once the alignment of the tubing system 155 is set, the spacial alignment is maintained by the netting, mesh or thin perforated film, as shown in 160 of FIG. 1J. In this diagram, the layer 151 above and the layer 153 below the tubing system 155 maintain its position. An alternate embodiment is configured with only one layer, e.g., only one layer either above, below or between (e.g. in the same plane as) the tubing system 155. This ability of maintaining alignment can be facilitated by having structural integrity of the layers 151 and 153 and some minimal tensile strength to prevent movement of the tubing system 155.

Figure 1K:
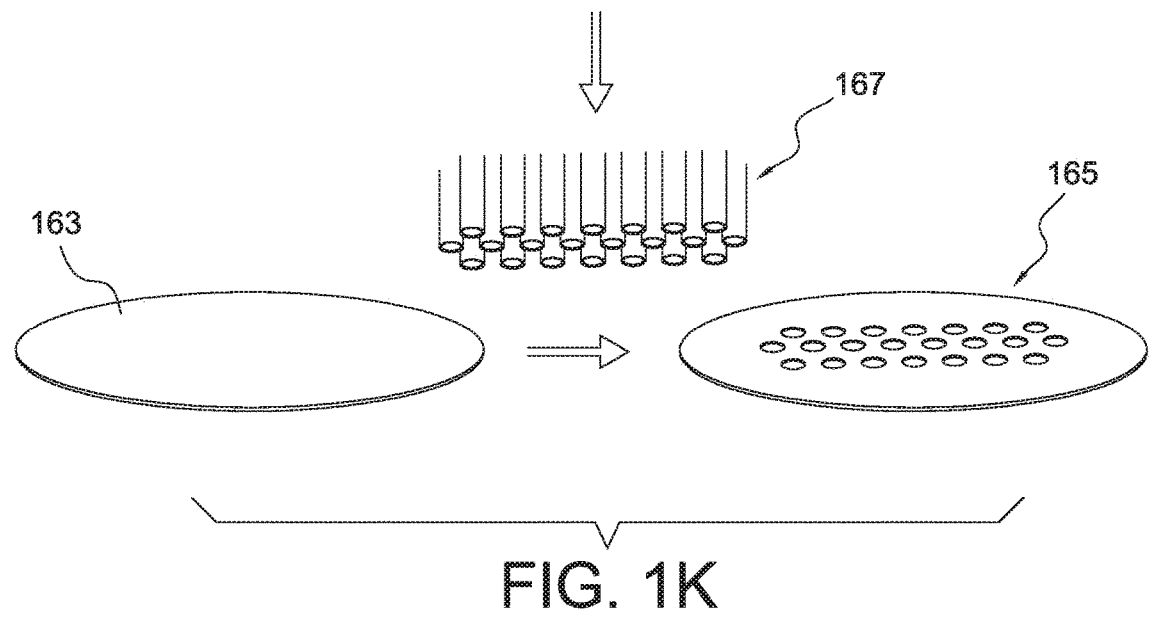
FIG. 1K depicts the result of a process in which a single closed cell layer is made into a porous layer.

FIG. 1K depicts the result of a process in which a single layer of thin film 163 is made into a porous layer. This process can be accomplished through multiple manners. In the example depicted in the figure the pores or holes are created using a cutting or punch process, for example, using a tool such as a group of cutting tubes 167. In this way pore or holes are created through a single solid thin film to create a thin perforated film layer 165. This process aids in preventing free edges or pieces from being created. This manufacturing process or structure may be used to eliminate unraveling or fraying that is typically encountered with some woven or multi-strand mesh or netting structures. The ultimate goal is to eliminate the concern for leaving small pieces of loose strands or pieces within a wound bed.

Figure 1L:
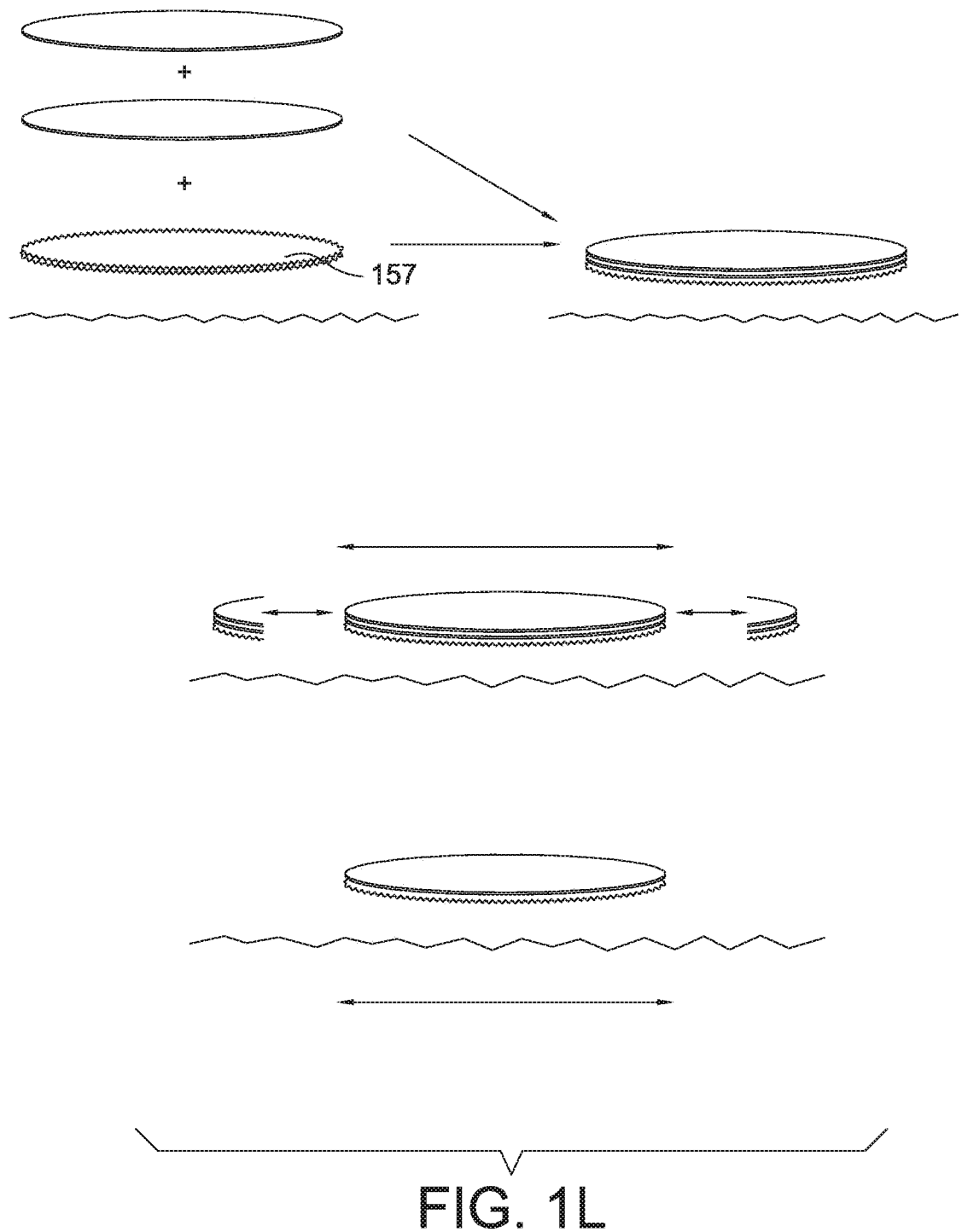
FIG. 1L depicts embodiments of a multi-layered dressing configured with an abrasive ventral layer.

FIG. 1L depicts embodiments of a multi-layered dressing configured with an abrasive ventral layer 157. This layer 157 allows for micro-debridement of the wound to assist in the removal of dead tissue from the wound surface. This abrasive surface 157 can move across the wound by any or all of the following effects: the push/pull motion induced by cyclic inflation/deflation of the positive pressure bladder, sheer motion from the dorsal surface of the unified dressing rubbing against the environment and/or from the muscle in or immediately deep to the wound bed contracting. The abrasive quality of this layer can be manufactured by several different means. For example, one such manner of implementing the abrasive includes the creation of elevations (e.g. <1 to 5 mm in height and separation. Alternatively, an abrasive coat or application can be applied to the wound facing surface of the layering material which would randomly alter the thickness of the wound facing layer. This abrasive coat 157 creates a micro-abrasive wound facing surface to facilitate wound cleansing.

Some embodiments feature layers of biologically inert polymer netting, mesh or thin perforated film, interposed between which are functional elements of the MWT dressing, or spacers. A "biologically inert material" does not decompose in a wound. This design controls spatial orientation of these functional elements to effectively apply the MWT concept, while maintaining flow-paths between the vacuum and irrigation source and the surface of the wound. The ability to specify the location of specific functional elements of the unified dressing is a novel and useful improvement inherent to this design, as specific spatial resolution is required to support advanced "smart" features of the MWT system (e.g. forms of leak site detection, wound surface monitoring, selective site delivery of irrigant . . . ). Piece-meal conventional systems cannot provide this same specified spatial resolution. Further, the layering material reduces or eliminates tissue in-growth which complicates conventional systems. Another of the several advantages the controlled spatial relationship between elements in the unified layered dressing, is that it tends to minimize, or controls in a way favorable to the clinical intent, the space-occupying effect of the dressing to facilitate wound contraction.

Figure 1M:
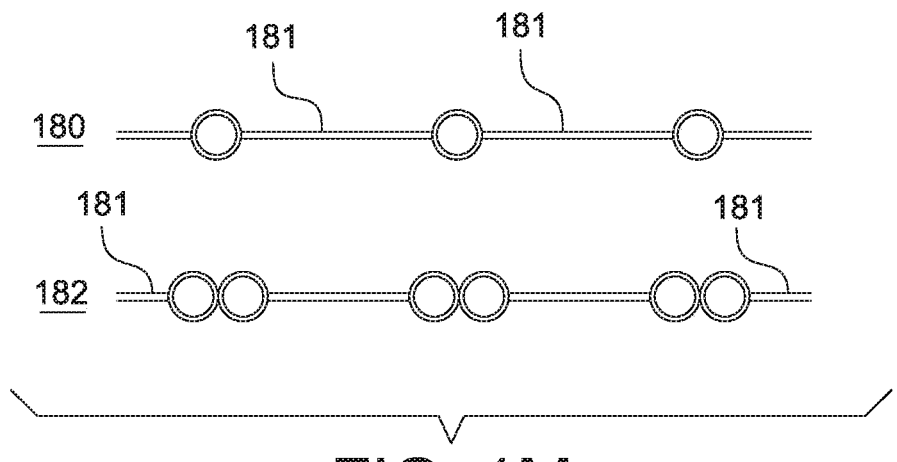
FIGS. 1M-O depict various embodiments of a unified dressing with different tubular structures configured to be placed, as a unit, directly over the wound.
Figure 1N:
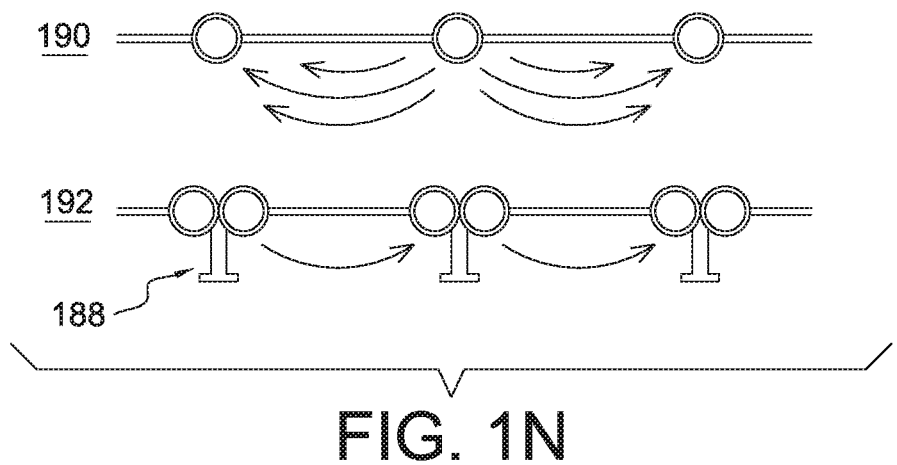
Figure 1O:
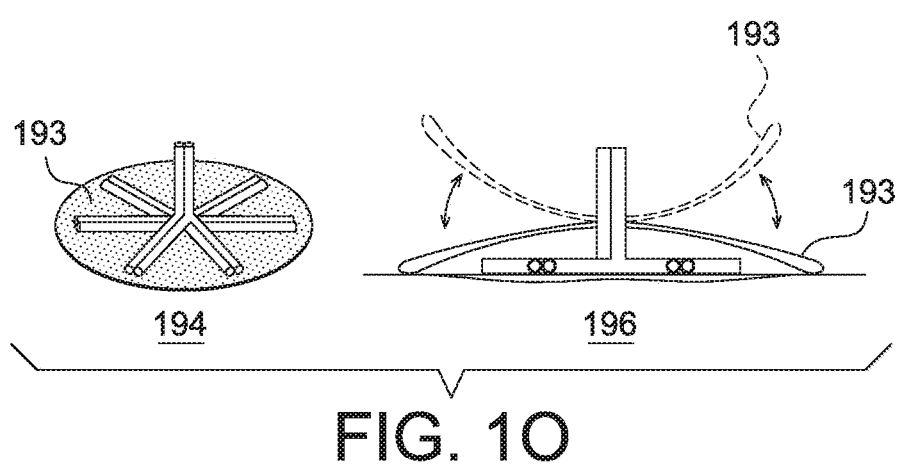

FIGS. 1M-O depicts various embodiments of a unified dressing with different tubular structures configured to be placed, as a unit, directly over the wound itself rather than using the wound filling materials of conventional systems or the layer dressing disclosed for the embodiments depicted in FIGS. 1 B-C. While this single layer dressing embodiments do not require wound filling materials, in certain clinical indications the single layer dressing can be placed over wound filling materials (e.g. sponge, gauze or other). In these cases, the wound filling material can be placed piece-meal or it can be permanently affixed to the single layer dressing through fabrication to form a unified composite dressing. In the embodiments of FIGS. 1M-O the tubing system and wound netting, mesh or thin perforated film are integrated into a single unified layer by affixing the netting, mesh or thin perforated film to the tubing or weaving or otherwise fabricating the tubing into the netting, mesh or thin perforated film. The tubular system provides the dedicated flow path(s) for vacuum, or for vacuum and irrigation. When the tubular system is used to convey vacuum and irrigation, the ventral (closest to the wound) portions of the tubing may be shared or remain separated out to the wound surface.

This design differs from previous designs (Shuler Published U.S. Patent Application Number: US2011/0054283A1) in that the tubing directs irrigant to the periphery of the dressing—enabling a flow path across the wound to the vacuum interface and then retrograde from the sealed dressing to the collection canister. An abrasive quality of the ventral surface of some embodiments of the single layer dressing aids in mechanical debridement.

FIG. 1M depicts a cross-section of a single layer dressing. The single-tube embodiment of FIG. 1M shows a cross sectional drawing of a single tubing system 180 with a thin layer of netting, mesh 181 or thin perforated or nonperforated film connecting the irrigation and vacuum tubes. By "single-tube" (or "single lumen") it is meant that the tubes are positioned singly throughout the layer, rather than in pairs (or multiples). The connecting material 181 (e.g. mesh) aids in maintaining the spatial relationship of the tubes, provides structural integrity to the dressing and can allow for passage of fluid or gas around the tubes. The dual-tube embodiment 182 of FIG. 1M is a similar design, except with a dual lumen tube or two completely separate tubing systems. In the dual lumen embodiment 182 the vacuum tubes and irrigation tubes are routed adjacent to each other, with the pairs of tubes connected by the webbing material 181 (e.g. mesh). Typically, one of the dual tubes is dedicated to vacuum, while the other is dedicated to irrigant. Yet other embodiments involve additional tubes, for example, a triple-tube embodiment. The third tube, which typically runs parallel to the other two, can be used for another purpose, e.g., dedicated to carrying a medical agent, or as a redundant spare tube in the event of a failure/clogging of the vacuum or irrigant tubing system.

FIG. 1N depicts the flow of fluid from one tubing system which is an irrigation system to another suction system. In view 190 a single lumen system allows flow from one tube to another tube spatially connected by the material between them. In this manner, the flow occurs across the wound which is positioned below the tubes. The additional dual lumen figures depict a manner in which flow can be controlled in order to drive fluid across the wound surface. The path of least resistance pictured in the embodiment of view 190 would be out of one tube and back in the tube connected to it in the dual lumen system. By placing a dividing ridge 188 that restricts flow between the two lumens as pictured in view 192 the fluid is forced to travel across the wound surface to a neighboring tubing system.

FIG. 1O depicts the sealing layer 193 over top of the single layer dressing. This thin film would be airtight and have adhesive on some or all of its ventral surface to create a seal over the wound and allow for negative pressure to be applied. In various embodiments, a thin (e.g. <1 mm) film of plastic or polymer may be used for the sealing layer 193. Commercially available products which are similar to the design envisioned are Tegaderm™ or Ioban™. The embodiment shown in view 194 and 196 of FIG. 1O features an airtight sealing layer 193 over the single layer dressing's underlying tubular network. This same sealing layer configuration can be used in conjunction with a multi-layered unified dressing as well. The sealing layer 193 is affixed to the central portion of the single layer dressing at fabrication, to create a unified airtight dorsal surface—that is, the surface of the dressing facing away from the wound, through which pass the connection tubing for vacuum and irrigation. To use the sealing layer 193, it may be unfolded from its folded state, the paper strips covering the adhesive removed (if any), and then the sealing layer 193, may be sealed in an airtight manner to the dorsal surface of the dressing and patients skin around the wound to produce a closed space under the dressing. This airtight seal is further achieved by placing adhesive sealing sheets on top of the sealing layer of the single layer dressing and the surrounding skin margins to complete the seal, making this embodiment unidirectional and unified in its effect. Alternatively, the sealing layer 193 can have an apron-like extension that has adhesive on its ventral surface, covered by peel-away paper backing. This can be used to make or initiate the seal of the dressing to the skin at the margins of the wound. The connection tubing entering the dressing, the airtight sealing layer and the single layer dressing are composite, that is they are fabricated as a single unit. The sealing layer 193 is air-tight and water-tight serving as the dorsal most layer of the dressing. The dorsal surface of the sealing layer 193 can be "tacky" or possess a sticky quality that serves to further improve the adhesion of the adhesive sealing sheets to the sealing layer. This tacky portion can be covered with a removable film or paper backing that preserves the purity of the tackiness when not in use. Separate adhesive sealing sheets are then placed at the periphery to seal the sealing layer 193 of the dressing to the wound margins.

In some embodiments, the adhesive sealing sheet may be united with the sealing layer 193 of the single layer dressing, into a unified composite sealing layer, possessing an apron-like extension with adhesive on the ventral surface of the apron. In other embodiments the sealing layer 193 may be affixed only to the tubing connection point at the dorsal central surface of the single layer dressing. The remaining portions, including an apron-like extension may have adhesive on the ventral surface of the sealing layer. Typically this adhesive portion is covered with peel-away paper backing. The adhesive on the sealing layer 193 may have adhesive over its entire extent, or only at the peripheral portion, e.g., from the peripheral edge inwards by a distance of from to 2 to 10 cm. This creates a semi-adhesive strip at the peripheral edge as narrow as 2 cm wide in some embodiments, and up to 10 cm wide in other embodiments. The sealing layer 193 may be configured so it can be folded back on itself in the midline, for example, as shown in embodiment 196 of FIG. 1O. The single layer tubular portion is cut to the size of the wound and then placed into the wound. The incorporated sealing layer 193 with adhesive—a part of the unified dressing structure—is then unfolded to cover the single layer dressing and removably affix it to the skin at the margins of the wound, affecting a sealed closed system between the dressing and the patient. The peel-away backing of this adhesive open at the midline, so the periphery can bet cut to match the dimensions of the wound as well, while still preserving the peel-away backing feature. In this context, the term "removably affixed" means that it can be fastened (e.g., stuck on with an adhesive) in a manner that allows later removal, that is, it is not permanently affixed to the patient, or affixed so strongly that it will tear or otherwise damage healthy skin upon removal.

In other embodiments, the dorsal side (surface facing away from the wound) of a dorsal most apron-like sealing layer that is centrally affixed to the tubing interface of the dressing, has at the periphery a tacky substance (similar in adhesive quality to 3-M Post-It® note paper), which is covered with peel-away paper backing. This is removed when the dressing is set to be removably affixed to the patient, and this tacky substance serves as an adhesion enhancer for the adhesive sealing sheets used to seal the apron (and underlying dressing) to the patient. These adhesive sealing sheets are placed over this tacky substance and onto the skin at the margins of the wound to affect this seal. This allows for 1 to 2 inch strips only to be applied to the dressing at its periphery instead of covering the entire dressing with a thin adhesive film, since the dressing itself is airtight by fabrication, as opposed to the piecemeal conventional dressings, which require the air tight seal to be created in situ at the level of the wound over the entire dressing surface and adjacent skin margins.

Figure 1P:
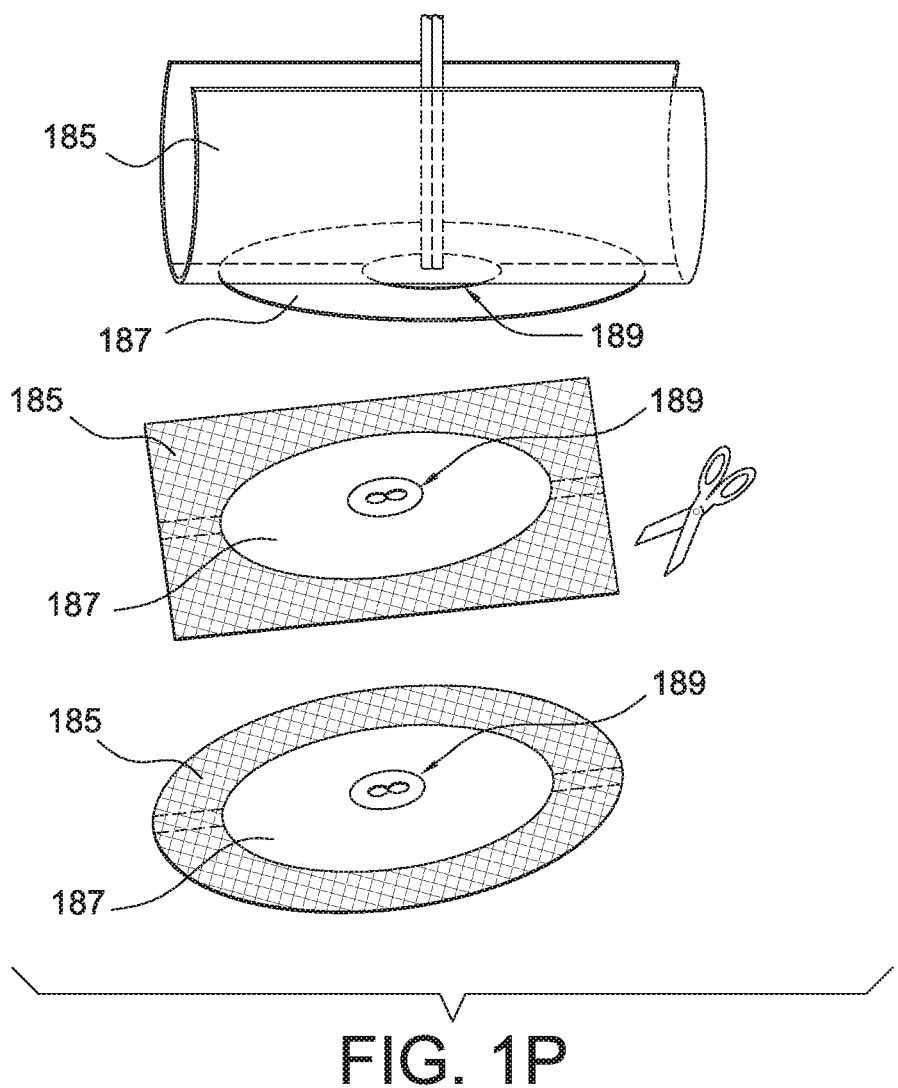
FIG. 1P depicts an embodiment with a top sealing layer sealed to the dressing in a central location.

FIG. 1P depicts an embodiment with a top sealing layer 185 sealed to the dressing 187 in a central location 189. This top sealing layer can be attached through fabrication to either a single layer or multi-layer unified dressing 187. The sealing layer 185 can be folded up into a folded state for packaging in a packaging wrapper or other removable covering. It consists of a thin (e.g. <1 mm) pliable plastic or polymer with an adhesive substance on the ventral side. Commercially available products which are similar to the design envisioned are Tegaderm™ or Ioban™. An adhesive cover can also be used to allow for placing the sealing layer 185 when ready. The sealing layer 185 can then be unfolded to an unfolded state and trimmed separately from the dressing 187, so as to fit over the dressing 187 which has itself been trimmed to fit the wound. Once each item is trimmed to size—that is, the dressing 187 to the size of the wound and the sealing layer 185 to a size larger than the wound—the sealing layer 185 is placed over the dressing 187 as it lies in the wound bed and affixed to the skin at the wounds margins to create an airtight system.

Figure 1Q:
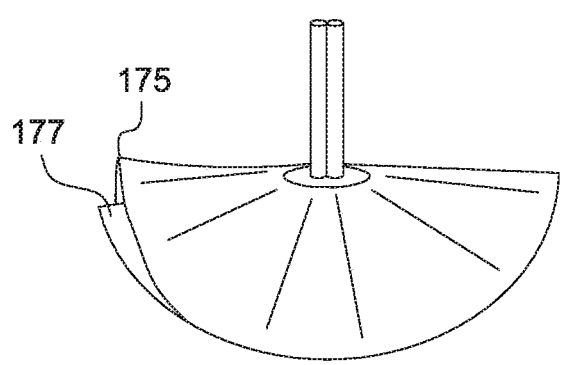
FIG. 1Q depicts an embodiment with an airtight film over top of whole dressing.

FIG. 1Q depicts an embodiment with an airtight film 175 over top of whole dressing 177, which again could be the single layer or multi-layer embodiment of the MWT layered dressing design. The material may be a thin (e.g. <1 mm) film of plastic or polymer. Commercially available products which are similar to the design envisioned are Tegaderm™ or Ioban™. The airtight film 175, is typically affixed permanently at fabrication to the dorsal surface of the entire dressing 177 and in apron containing embodiments this airtight film may extend peripheral to the single layer tubing portion of the dressing, but there may be embodiments, in which the fixation of the sealing layer is partial, for instance only being at the central tubing connection point. In some embodiments, the dorsal surface of the dressing 177 can have a sticky dorsal surface to promote the seal between the airtight film 175—sometimes called sealing layer 175—and the dressing. The inherent sealing layer 175 eliminates a common source of leakage and dressing failure for conventional systems.

Figure 1R:
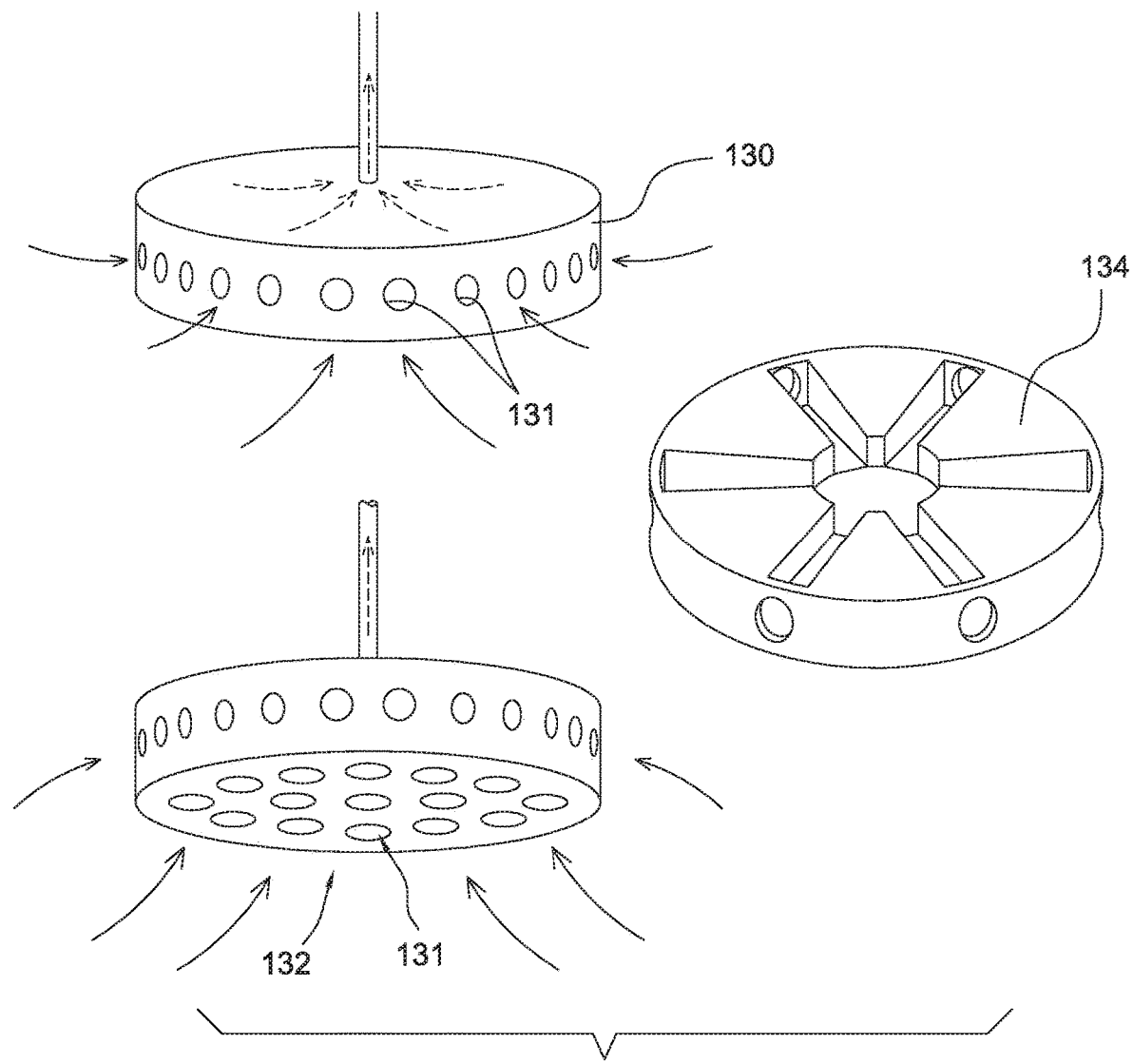
FIG. 1R depicts an embodiment of the central suction cavity.

FIG. 1R depicts an embodiment with a central suction cavity. In this implementation the chamber is in a disk or cylinder shape. The disk has a side wall 130 with pores 131 through it as well as a floor 132 with pores 131 to allow the passage of fluid or gas through it into the central collecting chamber. The figure depicts one way of reinforcing the chamber to prevent collapse. In this depiction, the inside has a series of ridges 134, walls or other structural components to prevent collapse that provides channels to a central suction tube insertion point.

Figure 1S:
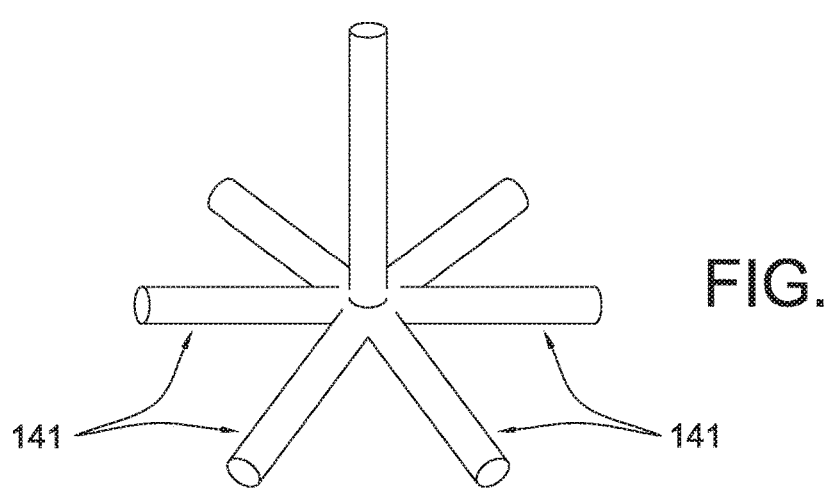
FIG. 1S depicts an embodiment of a multi-flange design from the suction delivery to the dressing.

FIG. 1S depicts an embodiment of a multi-flange design for the suction delivery to the dressing. In this embodiment there are several flanges 141 that provide equal suction. This redundancy allows for the case where one flange becomes clogged. If a single flange is clogged there are several others to continue providing suction.

Figure 2A:
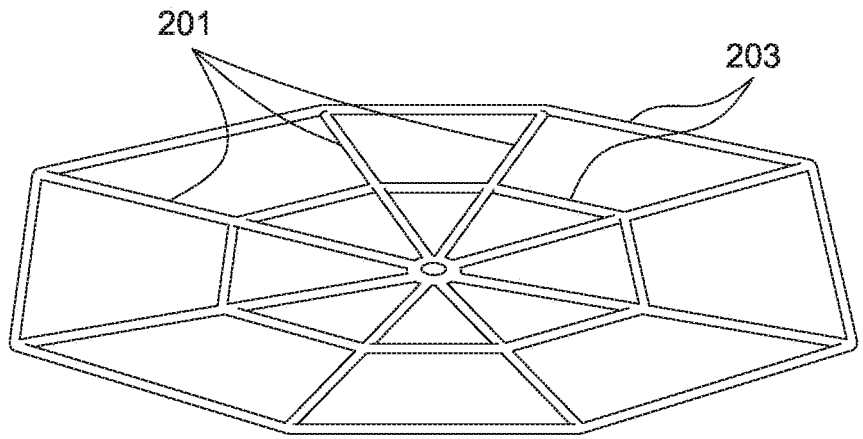
FIGS. 2A-C depict typical geometric arrangements for the irrigation tubing system and/or vacuum tubing system.
Figure 2B:
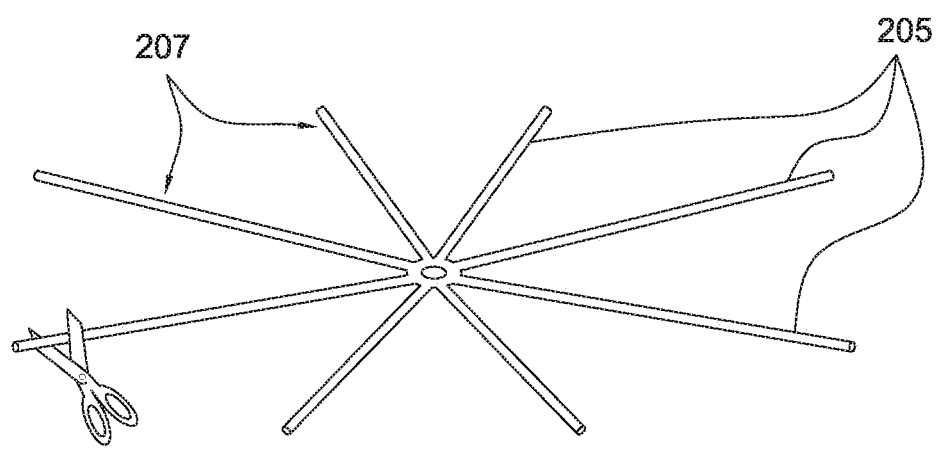
Figure 2C:
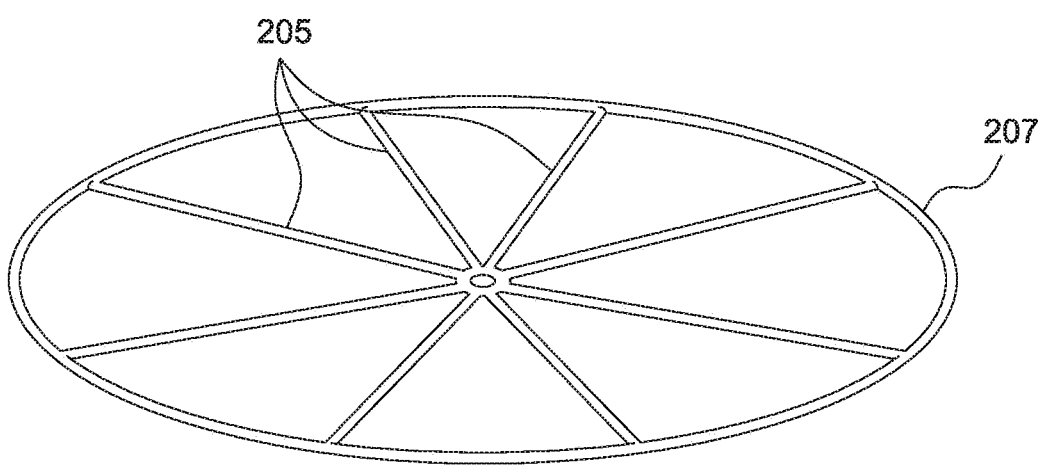

FIGS. 2A-C depict embodiments of the single layer dressing with only a tubing network without netting, mesh or thin perforated or nonperforated film. The tubing is typically constructed from plastic or polymer material that is biologically inert. This embodiment of the vacuum tubing network may be placed into a wound and then covered by the centrally affixed airtight sealing layer (also known as the cover component or covering layer). In other embodiments two tubing networks, one for vacuum and another for irrigation, rest ventral to the airtight sealing layer. In various embodiments the single layer dressing can either collapse upon themselves in a controlled or random fashion as the wound volume is reduced, or the single layer dressing can be trimmed at its edges to conform to the shrinking size of the wound. This supports the wound approximation goal of MWT, by preventing resistance to wound approximation that can occur related to the mass-effect of bulky nonideal wound fillers used in conventional dressings.

FIGS. 2A-C depict typical geometric arrangements for the irrigation tubing system and/or vacuum tubing system. This tubing system may be used within various implementations across the MWT platform. It can stand-alone, as it does in the single layer dressing. It can also be a functional element of either a layered dressing, as demonstrated in FIG. IB, or a unidirectional wound filler dressing, as demonstrated in FIG. 12C. The perforations in this irrigation tubing system can be located throughout along the length of the radial arms 205 and horizontal traversing connectors 203—typically oriented only towards the ventral or lateral surface (not dorsal) or only at the terminal ends of the radial arms 205 of the tubing system. In the single layer dressing, the space between tubes 205 may be filled with netting, mesh or thin perforated or nonperforated film, while in the layered dressing, this space is vacant or filled with spacers and the tubes are held in their spatial relationship, by being permanently affixed to the layering material ventral and dorsal to the tubing. In the unidirectional filler dressing, the space between the tubes may be filled with wound filler, as the tubing system is recessed into the ventral surface of the dressing. In various embodiments, the unidirectional dressing may have therapeutic adjuvants embedded or otherwise contained in or with the wound filler.

FIG. 2A illustrates a generic tubing layer suitable for use in a number of the embodiments disclosed herein. The radial arms 204 are each positioned to extend radially in a peripheral direction from a central connection point of the tubing network and the horizontal transversing connectors 203 connect between radial arms to produce a web pattern. In some embodiments the horizontal transversing connectors 203 are simply braces that hold the radial arms 204 in place. In other embodiments the horizontal transversing connectors 203 are themselves tubes that provide vacuum/irrigant flowpaths between the radial arms. This helps to promote an even dispersal of vacuum and/or irrigant, and also provides alternate fluid flow paths in the event a fluid passage hole on a tube becomes blocked. In other embodiments, e.g., as depicted in FIG. 2B, the tubing system only has radial arms 204, with no transverse connectors. This geometric configuration of the tubing system can be configured to support a collapsing effect, in response to progressive wound approximation, directed by modules of the MWT system, e.g., a wound approximating module.

One or more fluid passage hole perforations are provided on each of the tubes to facilitate flow of the vacuum and irrigant. The fluid passage holes may be configured on any side of the tubes, depending upon the nature of the wounds intended to be treated. Typically, there are perforations on three sides of the tube-downward (ventral), left and right— with the top (dorsal) side remaining without perforations. In some embodiments the perforations are only provided on the sides, left and right, while other embodiments the perforations are provided on the bottom (ventral) but not the sides of the tubes. In some embodiments the perforations have a uniform size. In other embodiments the perforations are smaller towards the center of the tube web where the pressure (or vacuum) is greatest, with larger perforations provided towards the outer part of the web where the pressure (or vacuum) is less strong. This is done in a manner to promote an even flow of vacuum and fluids from the centermost holes to the holes toward the periphery of the wound. The location and geometry of the holes aids in directing irrigant fluid onto the wound surface. This can be an advantage over conventional systems with holes facing away from the wound or randomly distributed by non-tubular type wound filling materials (e.g., sponge or gauze based dressings) which may allow flow of the irrigant away from the wound, preventing the irrigant from coming in contact with the wound to assist in wound cleansing.

FIG. 2B depicts an embodiment in which the individual perforated tubes 205 extend outward as spokes from the central connection point in a radial pattern. The tubes 205 are configured in a radial pattern extending outward in a lateral direction from the center which serves as the delivery point for vacuum and/or irrigant. The "lateral" direction, in the present context, is the direction side-to-side, generally over the surface of the wound, (e.g., approximately 90 degrees from the dorsal to ventral line is laterally). It should be noted that the various components (e.g., tubes 205) tend to be flexible. Although they are said to extend laterally they may flex to conform to the contours of the patient's body and actually be at somewhat different angles than 90 degrees. For example, the tubes 205 extending laterally may in fact be at 90+/−15 degrees from the dorsal to ventral line outward from the wound. In the embodiment of FIG. 2B the radial arms 205 may be trimmed to shorter lengths in order to shape the radial pattern tube network in order to alter the coverage size of the tube network to accommodate the shape of a wound. These radial spokes can also zig zag or curve within the plane of the dressing to allow for more coverage of the wound with the irrigant. The dressing itself including the radial tubing may be trimmed in order to fit specific wounds during application. Since the radial tubing design allows the dressing and tubing can be cut to size at any location and the system will still function as designed.

FIG. 2C demonstrates a radial arm embodiment, that has an additional peripheral ring 207 of tubing or spacing material. The peripheral ring 207, when configured as operable tubing, is in fluidic connection with the radial arms 205 and central connection point. That is, fluid (or vacuum) that flows through the radial arms 205 also flows through the peripheral ring 207. In one embodiment of the tubular system, there are no perforations in the radial arms 205, only in the peripheral ling 207, and any perforations created by cutting the peripheral ring 207 or radial arms 205 to fit the size of the wound. This embodiment promotes vacuum and/or irrigant to reach the periphery of the wound. In all embodiments of the tubing system, the tubes 205 and 207 can remain free of material interspaced between the tubes or netting, mesh, thin perforated film or other wound filling materials (e.g. sponge) can be placed between the tubes to connect the tubing and/or preserve the spacing between the tubing. The tubing may be plastic or polymer with an inner diameter in the range of 1-3 mm. The outer diameter may be in the range of 3-5 mm. The size of the whole construct could vary based on function and use. Again sizes could be marked as large (for instance 6 inches in diameter), medium (for instance 3 inches in diameter) and small (for instance 1-2 inches in diameter). Lastly, since many wounds that would be ideally treated by the MWT platform of dressings have a more elliptical shape, the tubing systems and layered dressings possessing these tubing systems, may be configured in an elliptical shape with a long and short axis. Whether circular, elliptical or other geometry, the basic design features that have been described herein which promote universal customization and applicability would remain present in all geometries.

The vacuum tubing system, for example, the tubing layer depicted in FIGS. 2A-C, is typically in fluidic communication with the collection canister (e.g., canister 106 of FIG. 1A). In this way, the vacuum tubing system is configured so that fluids, either liquid or gas, can flow to the collection canister 106. Typically, this is achieved via a vacuum connection tubing (e.g., vacuum connection tubing 109 of FIG. 1C) that connects the collection canister to the tubing connection point on the dorsal surface of the dressing. The connection point for the vacuum tubing may be a specialized component called the vacuum interface chamber (e.g., vacuum interface chamber 121 of FIG. 1C) or the vacuum interface flange (in embodiments where there is no ventral floor). This serves to better distribute the vacuum to all portions of the sealed wound and to prevent system failure from blockages at a single point. When vacuum is applied the tubing system of FIGS. 2A-C transmits fluids retrograde toward the collection canister 106. In the typical embodiment, the tubing connection point has a one-way valve that avoids back-flow of wound effluent, preventing effluent from flowing back into the vacuum interface chamber or flange and possibly to the wound. With a one-way valve in place the wound effluent can only progress retrograde from the wound. Once the wound effluent crosses the one-way valve in the tubing connection point and enters the vacuum connection tubing, it cannot return to the wound or interface chamber.

When irrigants are pumped through the independent irrigation tubing system the flow of irrigant fluids occurs in the opposite direction (e.g. towards the wound in an antegrade fashion). Instead of actively pumping fluid (e.g. with the use of a motorized pump) through the tubing, the fluid can be delivered passively under the influence of gravity or vacuum can be the driving force to draw fluid across the wound surface and cleanse the wound. This vacuum, under the regulation of the EVR, can be programmed to provide intermittent bursts of negative pressure to allow maximal irrigation and agitation of the irrigant, to promote mixing at the wound surface and assist in the micro-debridement aspects of the MWT system.

In some embodiments, there is one tubular network of lines that serves the dual purpose of providing both vacuum and irritation, at different times. This embodiment must be switched between vacuum and irrigation since there is only one tube system. In layered dressing embodiments the vacuum lines and irrigation lines may be provided in different layers. That is, the irrigant lines may be configured in one layer, with the vacuum lines being configured in another layer. In yet other embodiments the irrigant lines and vacuum lines may be provided within the same layer, but using independent tube networks that are controlled separately. Netting, mesh or thin film can be affixed between the tubing or not. When vacuum and irrigation delivery is separated into two distinct tubular systems, the irrigation layer is placed closest to the wound, so that the flow path is from irrigation influx to/across the wound surface and then dorsally (away from the wound) to the vacuum system.

Figure 3A:
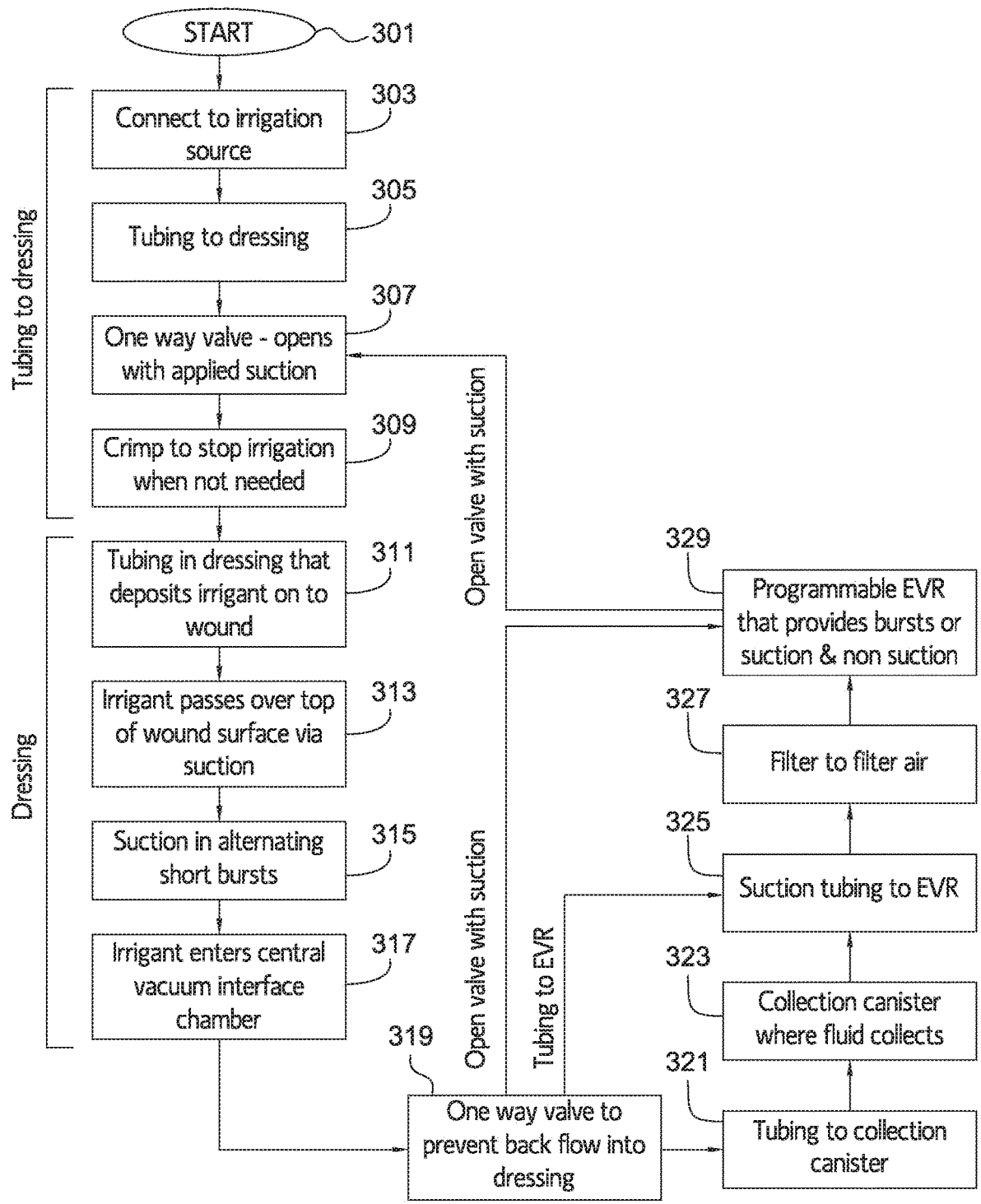
FIGS. 3A-B is a block diagram pertaining to the reverse pulse lavage system.

FIG. 3A is a block diagram describing an embodiment of the reverse pulse lavage system. Reverse pulse lavage is a novel concept for applying irrigation to a wound surface under a NPWT or MWT dressing. It consists of intermittent, controlled and programmable bursts of negative pressure via the vacuum tubing system/interface chamber/flange, which along with or without gravity, acts to draw the irrigant from its source, through its dedicated tubing system, across a one-way valve and then across the wound to be suctioned and delivered to the collection canister, e.g., as described in FIG. 3A. This system, removes the need for a positive pressure pump or gravity fed in-flow as the propulsion force for delivering irrigant to the wound surface. The pulsed nature of reverse pulse lavage, acts to agitate the fluid as it crosses the wound surface, to facilitate mixing of irrigant with wound surface biological collections (e.g., bio-films). Further this method of lavage, unlike positive-pressure pulse lavage (especially in the setting of high-pressure lavage often used in surgical irrigation), avoids the potential negative effects of driving wound surface biological debris or foreign material debris deeper into the wound and/or disturbing the normal wound healing process. The fluidic agitation produced by reverse pulse lavage provides a secondary mechanical effect which will improve the cleansing of the wound surface, bacterial burden reduction and maintenance of a healthy, moist wound bed surface. Lastly, this method tends to reduce the chance of irrigant pooling, which can erode the integrity of the dressing seal. Prevention of pooling can be assisted by a one way valve in the tubing connection point for the vacuum connection tubing at the dorsal surface of the vacuum interface chamber or flange. By preventing back flow from the vacuum connection tubing, the irrigant is forced to move away from the dressing and not back into it to allow pooling and recontamination at the wound surface.

The integrated wound dressing system of various embodiments is configured to fluidically connect a dressing component, connection tubing and collection canister all under the control of a control unit such as an electronic vacuum regulator (EVR). Conventional systems typically use the vacuum tubing network for the added purpose of irrigation when delivering a fluid irrigant to the wound. The various embodiments disclosed herein provide an improved system for delivering irrigants and/or adjunct therapies. In various embodiments described herein the vacuum tube system is separate from the irrigation system, from source to the sealed dressing and/or wound surface, to produce the intended wound surface irrigation effect. In such embodiments the vacuum tubes (or vacuum interface chamber) are fluidically separate from the irrigation system. In this way, the mixing point for irrigant delivered to the wound via the irrigation system and the negative pressure suctioning the irrigant and wound fluid from the wound is the wound surface itself. Separation of vacuum and irrigation flow paths allows for simultaneous irrigation and suction, similar to a pulse lavage device. This simultaneous application of irrigation and suction helps to prevent the pooling of irrigant fluid and reinforces the intended flow path of irrigation across the wound surface. This is an improvement over a common flaw of conventional systems that have dressings which have all or a portion of the irrigation flow-path shared with the vacuum flow-path. Lavage irrigation is not possible in conventional devices in which the in-flow and out-flow systems are not separated at the wound surface. This design flaw in conventional NPWT devices which possess irrigation systems potentially returns devitalized tissue and microbial burden back to the wound surface by forcing in-flowing irrigation fluid through shared out-flow tubing or by pushing irrigation fluid across exudate saturated wound filler, thereby re-contaminating the wound surface.

Moreover, the present inventors recognized another common flaw in the manner the conventional devices handled irrigation in the setting of NPWT dressings. Since conventional devices call for some or all of the tubing or other forms of flow-paths in the system to be shared between these two mutually exclusive functions, these functions must be run sequentially rather than simultaneously. This leads to a problematic situation in conventional NPWT dressings with irrigation wherein the wound filler becomes saturated and/or fluid pools. When this happens to conventional dressings the seal may be lost and the dressing is compromised. To avoid saturating the dressing, conventional systems limit the time the irrigant is applied. However, in doing this the conventional systems reduce the amount of irrigant actually reaching the wound, if the irrigant fully traverses the wound filler and reaches the wound at all. In conventional systems, even if the irrigant reaches the wound, it generally reaches through diffusion or instillation through the wound filler since it is delivered to the dorsal side of the wound filler, away from the wound. This wound filler is saturated with exudate, devitalized tissue and microbes, which are then driven/floated towards the wound. The propagation of "dirty" material within the wound filler towards the wound surface is contra-productive to the intended wound cleansing effect.

Returning to FIG. 3A, this figure provides a block diagram for embodiments of a reverse pulse lavage system. The method begins at 301 and proceeds to 303 where the system is connected to an irrigation source such as an IV bag. In block 305 the bag is attached to a tubing system to deliver the irrigant to the dressing, and on to the wound. In accordance with block 307 there is a one way valve that allows fluid out of the irrigant source only when negative pressure is applied to the system. In other words, irrigation is released only when sucked out of the source by the EVR regulated suction. Once the irrigant passes through the valve, it continues down the tubing where it passes through a crimp valve, as per block 309. The crimp valve can be engaged to prevent irrigation regardless of suction or negative pressure if no irrigation is desired. This is a shut off valve for reverse pulse lavage and other forms of irrigation within the MWT platform. Once the irrigant fluid is passed through the crimp valve, it passes into the dressing according to block 311 through its series of tubing and the irrigant is deposited on the wound surface. In block 313 the irrigant is forced across the wound surface to help debride the wound. The suction will be performed in an alternating manner to allow short bursts of suction, as per block 315, in order to increase the amount of irritation across the wound surface and increase agitation of the irrigant as it crosses the wound surface.

Once the irrigant crosses the wound surface it is suctioned back into the dressing tubing system at the central vacuum interface chamber according to block 317. The irrigant now travels through the suction tubing system away from the wound surface. As it exits the dressing, a one way valve is present on the tubing, in accordance with block 319. This valve prevents backflow of the irrigant as it leaves the dressing. In block 321 the irrigant then travels through the suction tubing towards the collection canister. The collection canister of block 323 is connected to an EVR of block 325 via an additional tubing that may or may not have a biological filter, block 327, to clean the air as it enters the EVR. In accordance with block 329 the EVR is programmable to control the timing, duration, strength as well as other factors of the suction which drives the system. The method proceeds from block 329 back to block 307 where the EVR opens the one way valve with applied suction to start the suction segment of the cycle.

Figure 3B:
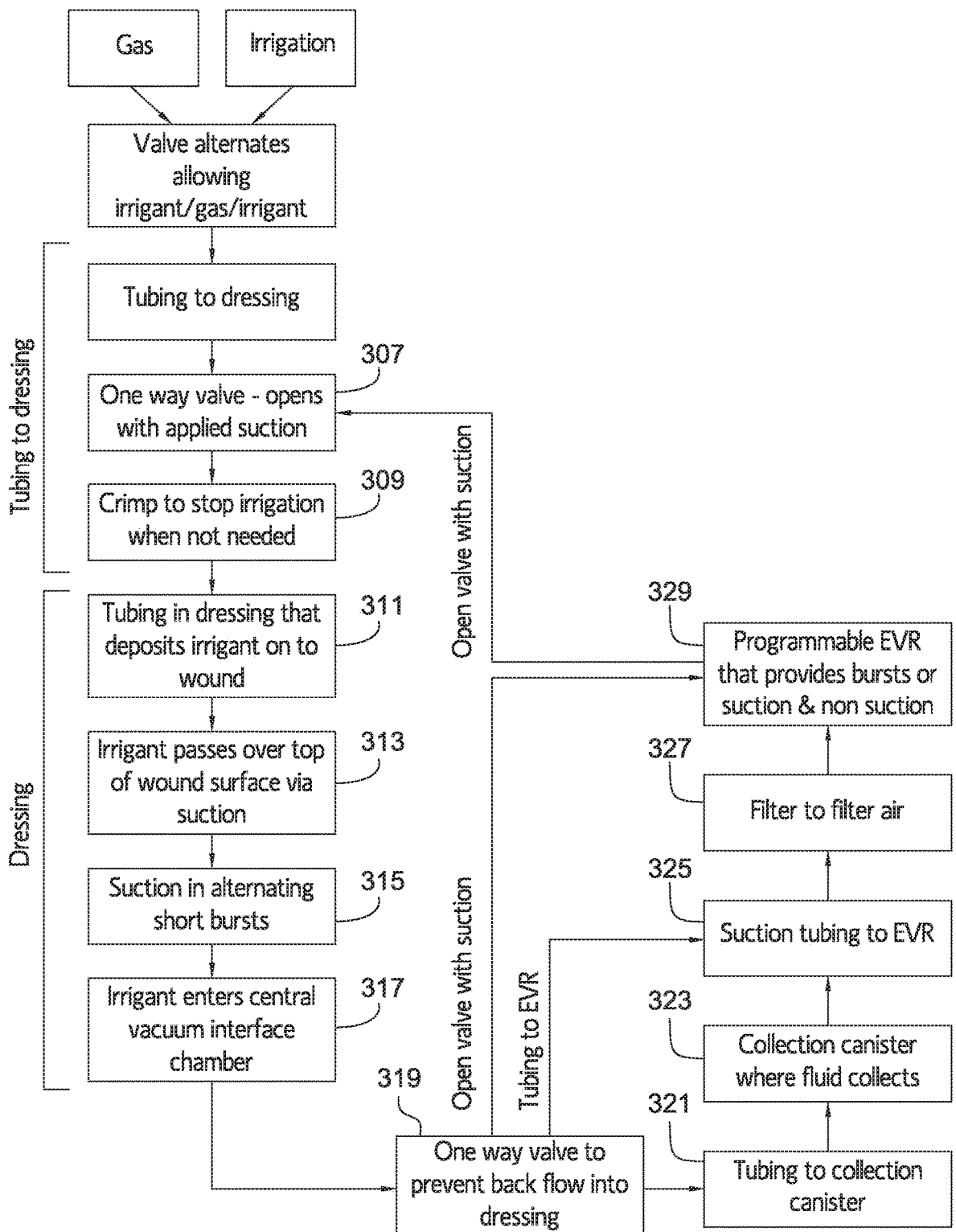

FIG. 3B is a block diagram pertaining to the reverse pulse lavage system similar to FIG. 3A, but depicting embodiments in which the irrigation source can be alternated between a fluid irrigation and gaseous irrigant. One benefit of this system is that it can be controlled by a valve that may be configured to alternate between the multiple irrigants. Using a gaseous irrigant between bursts of fluid helps to prevent pooling. The gaseous irrigant can clear the system of fluids before another burst of fluid is passed through the system. Further, gas irrigant will aerate the liquid phase irrigant, which can assist in the irrigation function and deliver these gases directly to the wound surface to promote healing.

Figure 4:
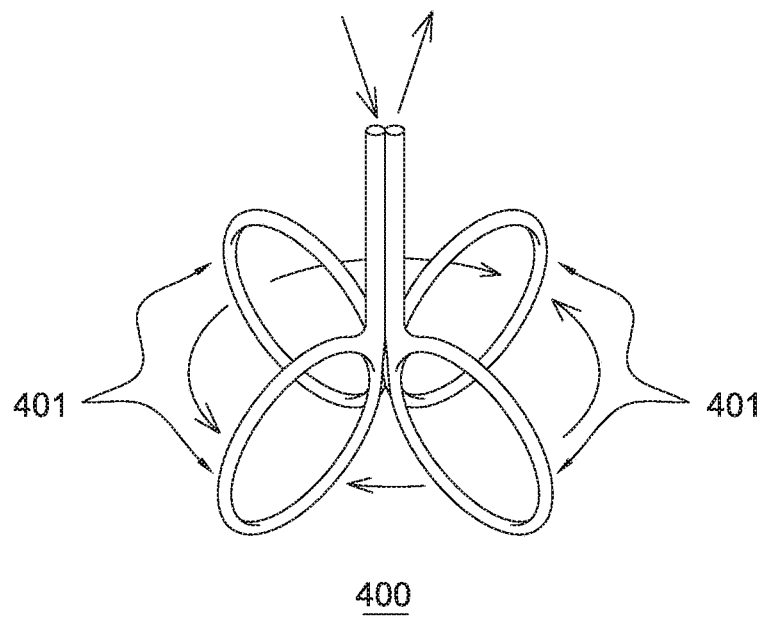
FIG. 4 depicts an embodiment of a multi-looped accessory dressing configured to be attached to the underside of the standard dressing.
Figure 4:
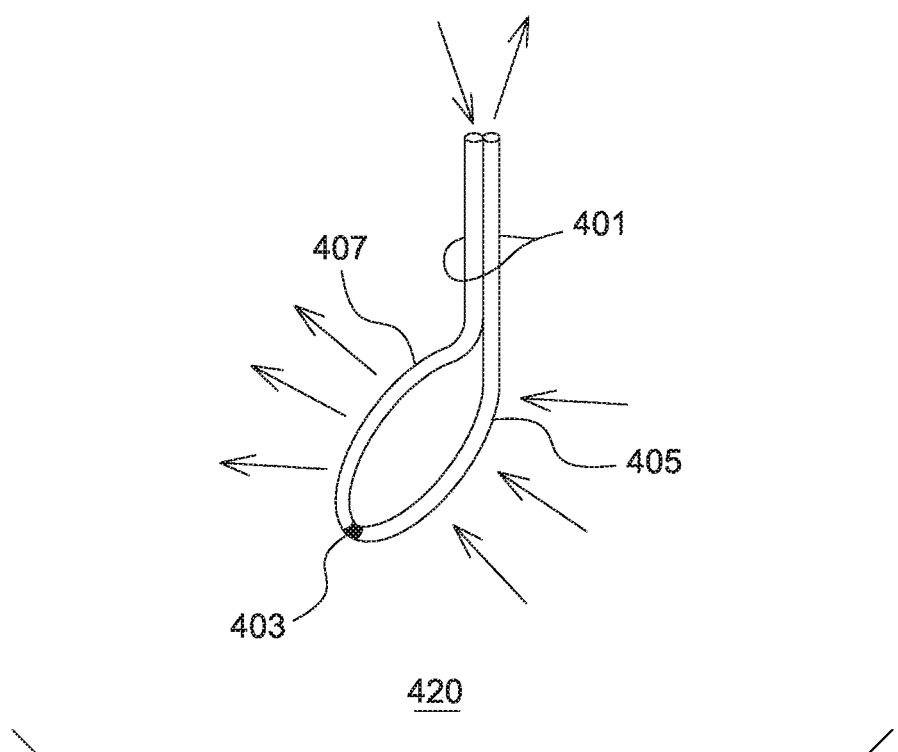

FIG. 4 depicts an embodiment of a multi-looped accessory dressing configured to be attached to the underside of the standard dressing. The multiple loops 401 in this embodiment can be arranged to fill a cavitary wound. FIGURE 400 depicts the multi-looped dressing with four different loops that may be configured to provide different functions. For example, some loops may provide irrigation while others provide suction. In one embodiment the function is alternated, so one loop provides irrigation and the adjacent loop provides suction. By separating the function, the irrigant must travel out of the tubing system into the wound before entering the suction loops. FIGURE 420 depicts an embodiment in which a loop possesses the ability to both irrigate and to provide suction. This embodiment is designed with a blockage 403 within the tubing. The tube 401 has an irrigation portion 407 and a vacuum portion 405. The blockage 403 forces the irrigant to leave the tubing from the irrigation portion 407, travel across the wound, and then enter the vacuum portion 405 of the tubing.

Figure 5A:
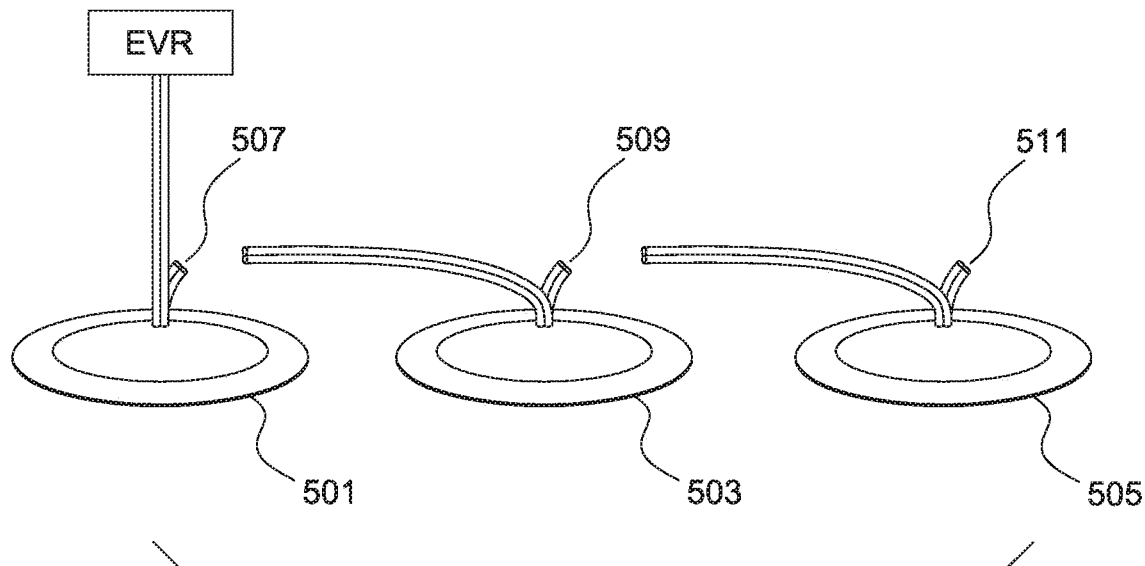
FIGS. 5A-B depicts an embodiment of wound dressings configured to be attached in series.

FIG. 5A depicts an embodiment of wound dressings 501, 503 and 505 configured to be attached in series to allow the same suction and irrigation source to provide multiple therapeutic dressing with the needed irrigation and suction. This capability is enabled by a set of ports 507, 509 and 511 at the junction of the dressing and the tubing. There is a quick connect at the port that allows irrigant to continue from the tubing to the next dressing tubing without all of the irrigant going into the initial dressing. In the embodiment depicted in FIG. 5A, if dressing 505 is the last dressing in the series, the port 511 can be closed (e.g. capped) to avoid leakages in the irrigant and vacuum lines. In another embodiment the port 511 can also be connected to the source of vacuum and irrigant, so suction and fluids are provided to the series of dressings at both ends. Valves just distal to the port allow the pressures to be adjusted for the irrigant and vacuum, and aid in preventing mixing of irrigants and cross contamination between dressings. This embodiment allows a single EVR to monitor and function as a negative pressure source and irrigator for multiple dressings. The EVR may be configured to provide separate monitoring displays and controls for each of the multiple dressings.

Figure 5B:
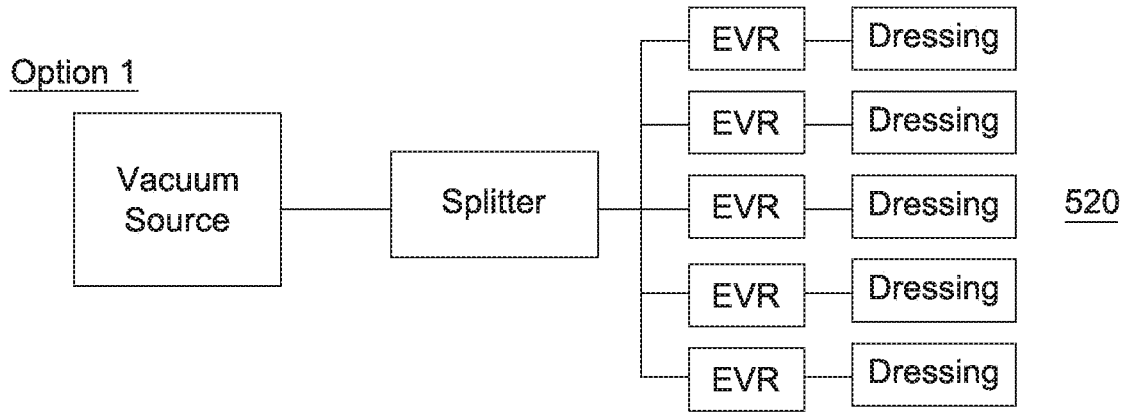
Figure 5B:
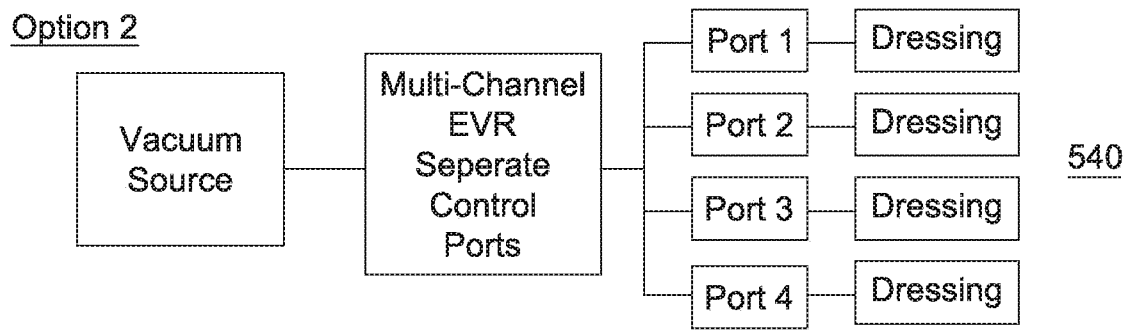

FIG. 5B depicts two embodiments 520 and 540 in which a wall suction or other suction source can be used to provide suction for multiple dressings. This suction source can be any suction device found in typical hospital or military settings. The first diagram shows a splitter that can separate the vacuum source into multiple suction outlets. In this case, multiple EVRs can be used to control the multiple suction sources created by the splitter. In other embodiments a multi-channel EVR is used to control the multiple negative pressure sources. The first diagram depicts a plastic or metal or polymer material with dimensions approximately 3 inches deep by 3 inches tall by approximately 3-12 inches wide depending on the number of splits required or desired. The second diagram depicts a single suction source with a single EVR. However, the EVR is capable of splitting the suction and providing separate EVR monitoring for multiple dressings through the same device. Again the size of this could vary based on design and function of other components as well as the number of out ports. The size may be determined by number of splits as well as additional functions built into the EVR.

Figure 6A:
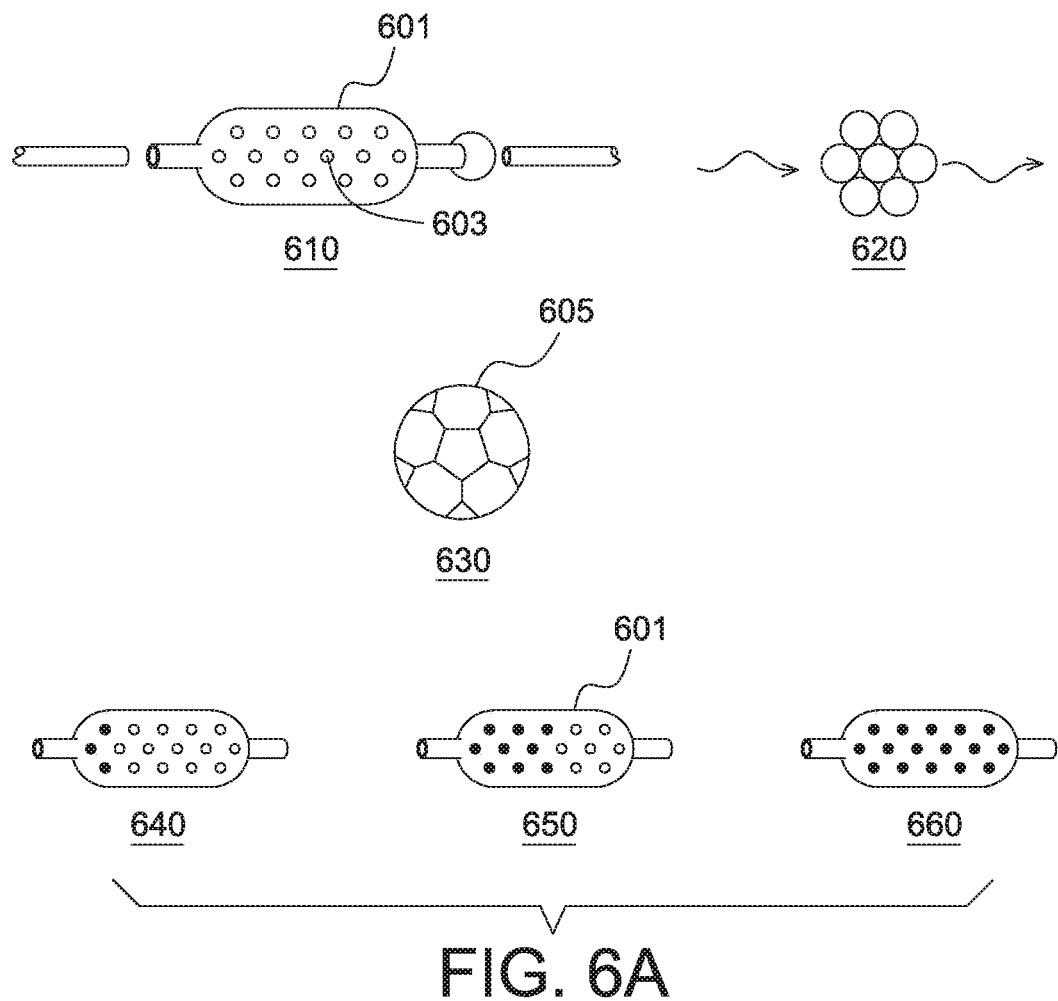
FIGS. 6A-B depicts an embodiment of a separating system for gas and fluid mixtures.

FIG. 6A depicts a number of views 610 to 660 of an embodiment of a separating system for gas and fluid mixtures. This system allows for separation without the use of gravity and a stationary canister. It uses a malleable bag 601 that is filled with hyper-absorbent spheres 603. The spheres 603 maintain their size to allow the mixture to pass through and between them. The can be made of super absorbent materials such as but not limited to sodium poly acrylate. These spheres may be uniform is size or vary in sizes between 2 mm in diameter to ≥1 cm in diameter. These spheres could be smaller or bigger as needed. As the mixture passes through the spheres 603, the air is dried. In some embodiments the hyper-absorbent material of spheres 603 are placed in a cage type structure 605 to prevent the closure of air passage ways. Additionally, multiple bags can be attached in series to allow for extra drying. The expectation is that the air may be dried sufficiently such that at the end of the collection bag there would be no fluid to be deposited on clothing or other surroundings coming in contact with the air. As additional mixture or fluid is added the spheres 603 proximate to the entrance will become saturated as shown in 640. As more fluid is added, more of the spheres 603 throughout the malleable bag 601 to the exit will fill with fluid, as shown in 650. Ultimately, all of the spheres 603 in the entire container 601 will become filled, as shown in 660. At that point an indicator signals the saturation of the container, to allow replacement of the bag 601. The alarm can be accomplished through a digital humidity monitor and alarm similar to but not limited to WHDZ (Manufacturer) AMT-123 or NSrnart/OEM (manufacturer) STH702/STH703. The connection to the tubing is a quick connect to allow easy connection and disconnection. Quick connects can be obtained such as ones provided by but not limited to Colder Products Company (St Paul, MN).

Figure 6B:
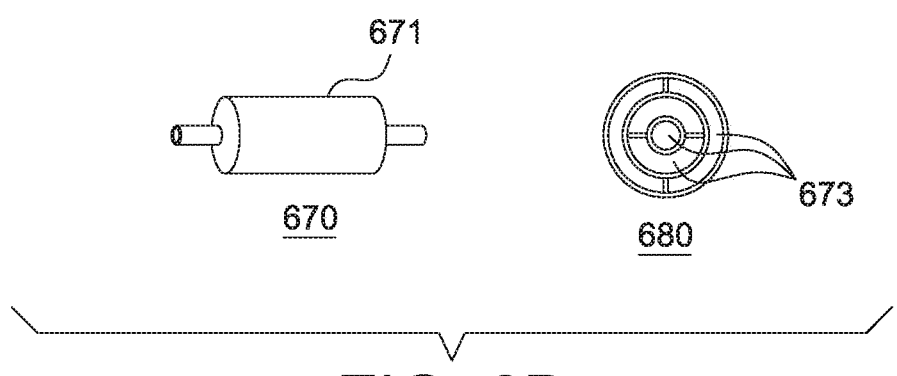

FIG. 6B depicts an embodiment of an alternate means to separate gas and fluid mixtures. Instead of spheres for separation, the present embodiment uses a cylinder type design, for example, featuring multiple cylinders 671 containing hyper-absorbent material. Cross-section view 680 depicts the hyper-absorbent material 673 within the cylinder 671. The cylinders 671 are positioned pass the mixture through the hyper-absorbent material as it is flowing toward the canister. By exposing the mixture to the multiple rings of hyper-absorbent material 673, the air is dried and passes out the opposite end without fluid. As in the embodiment of view 670, an indicator is configured to signal when the hyper-absorbent material 673 is fully saturated and it is time to change the canister 671.

Figure 7A:
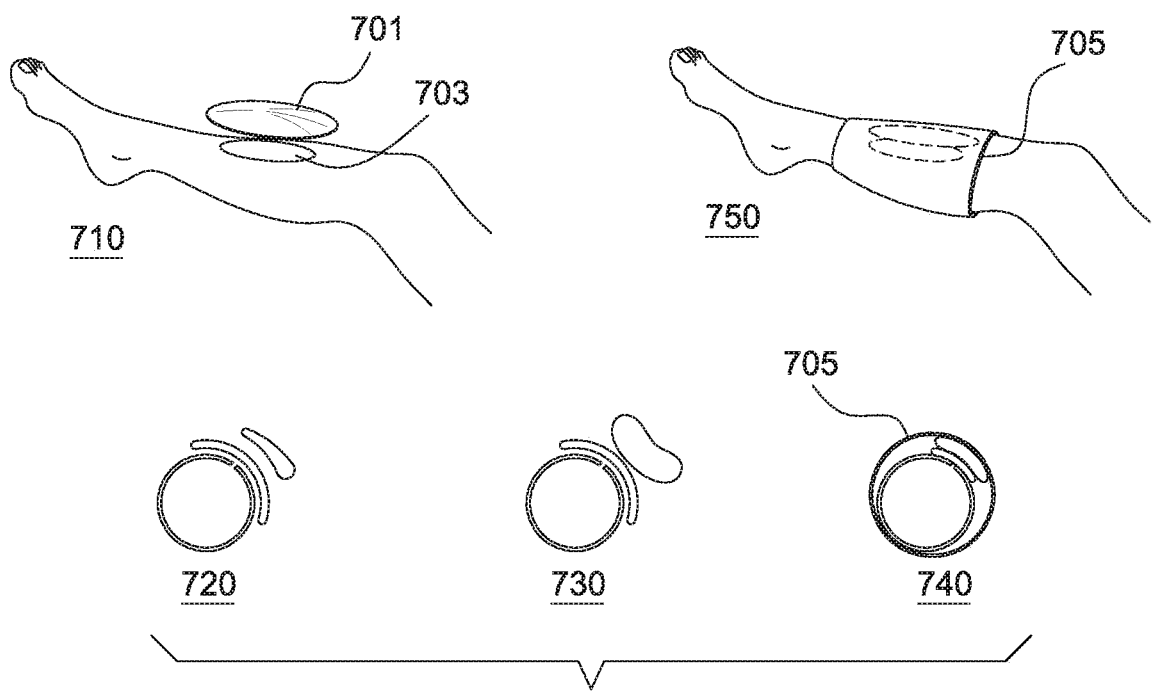
FIGS. 7A-B depict an embodiment of a bladder or positive pressure device configured for placement over a standard dressing.

FIG. 7A depicts an embodiment of a bladder 701 (sometimes called a positive pressure device) configured for placement over a standard dressing 703. View 710 shows the bladder 701 being placed over the wound on a patient's leg. Without an external sleeve to direct the pressure and force towards the leg, the bladder expands away from the extremity, as shown in views 720 and 730. When external sleeve 705 is wrapped around the extremity, as shown in views 740 and 750, the bladder 701 expands along the wound compressing the dressing 703 down on the wound similar to a sequential compression device (SDC). This arrangement allows for the edema to be compressed out of the injured tissue while also pressing the dressing down on the wound.

This bladder can be made of a less elastic material on the dorsal or outer side s as plastic, polymer, latex, vinyl or rubber. The more elastic ventral side generally allows for more expansion and be a latex, rubber, plastic or polymer material. The size may be varied based on the size of the wound. It could be designed in different sizes to match different size dressings from 2-3 inches in diameter to ≥12 inches in diameter.

The bladder design in this embodiment differs from prior art in several aspects (Shuler Published. U.S. Patent Application Number: US2011/0054283A1). Its design is unidirectional in order to allow the bladder to expand to the wound and is modular so it is not built into the dressing which allows for completely independent use. This design allows the bladder to be placed directly over the wound in order to compress the dressing onto the wound and reinforce the seal of the dressing. It also promotes micromotion of the dressing at the wound surface to aid in micro-debridement of the wound. Additionally, the bladder in combination with the wound approximating device assists in closing the wound by cyclic loading of the skin edges with intervening approximation under the continuous pulling force of the wound approximating device. The inflatable bladder may be controlled to stretch tissues before applying an approximation device. The pressure in the bladder typically allows for 2-10 newtons, or more, to be placed on the skin edges. The pressure could be monitored from the EVR to control the amount of pressure exerted on the wound or skin edges based on the amount of gas or fluid inserted into the bladder. The gas could be, but not limited to room air, oxygen, inert gas such as Nitrogen. Alternatively, a fluid such as tap water, saline or sterile water can be used to inflate the bladder. The fluids temperature can be varied to deliver either a cooling or warming effect depending on the clinical setting and desires of the treating clinician.

Figure 7B:
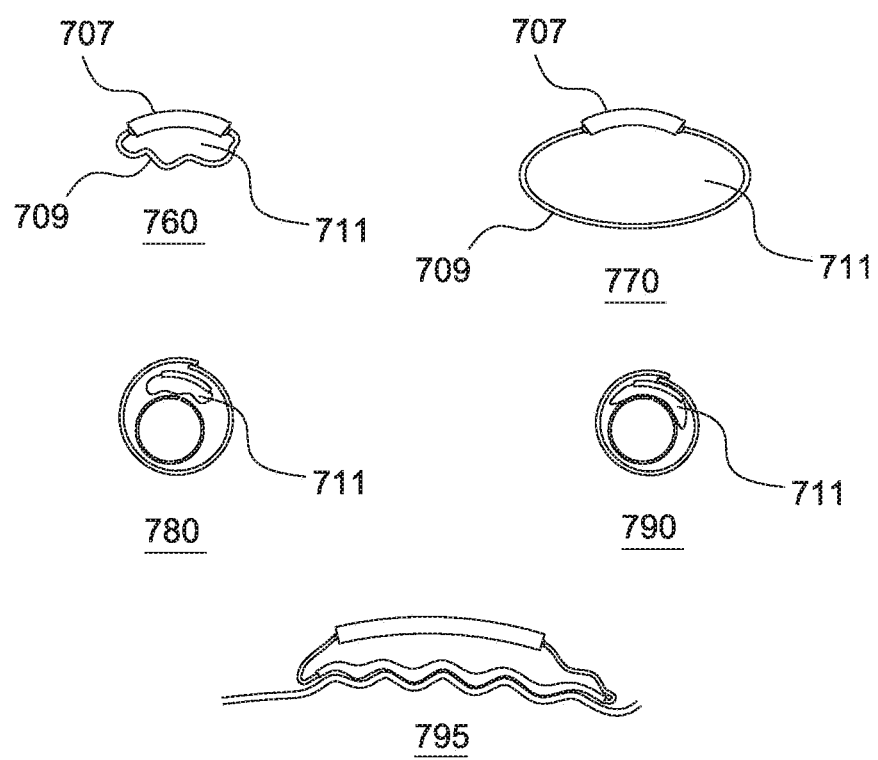

FIG. 7B depicts an embodiment of a unidirectional bladder. In this figure the bladder 711 is displayed deflated in view 760, and displayed inflated 770. A rigid top portion 707 of the bladder 711 is designed to be less flexible (more rigid) than the bottom flexible portion 709 of the bladder 711. The ventral side—the flexible portion 709—is a much more pliable material that expands down and outwardly. View 780 and 790 show a cross-section of the unidirectional bladder 711 positioned on an extremity (e.g., a leg), covered with a sleeve. View 790 illustrates the bladder in an inflated state with the flexible portion 709 of bladder 711 filling the wound bed and applying an even pressure throughout the wound. The inflatable bladder can be maintained in an inflated state for any amount of time to apply pressure to tissue beneath the inflatable bladder. A more rigid bladder would be likely to cause pressure to be applied to certain areas with little or no pressure being applied to other areas, thus creating pressure points and not filling the wound evenly. View 795 demonstrates how the pliable bladder embodiment 711 fills an uneven wound surface, providing even pressure on the wound dressing, and providing even pressure on the sealing layer above the dressing to reinforce the seal. This can only occur with a sleeve 705, backboard structure or simply using a more rigid material to form the dorsal surface of the bladder with means to prevent the bladder from lifting away from the wound and dressing, with the ultimate goal of directing the force of the bladder towards the wound surface.

This bladder can be inflated by manual control using a manual small pump similar to aircasts and boots used for lower extremity injuries (Aircasts walking boot). Alternatively, the inflation and deflation can be activated by the EVR or otherwise controlled by a pressure control unit.

Figure 8A:
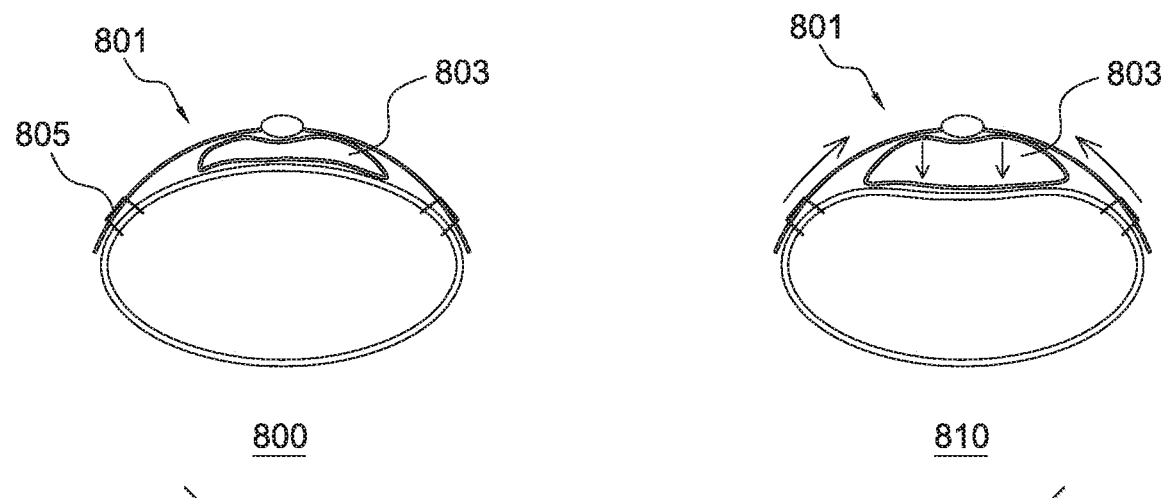
FIGS. 8A-B depict an embodiment of an approximating device.

FIG. 8A depicts an embodiment of a wound approximating device 801 (sometimes called a tensioning device) acting as a backboard, to direct the positive pressure bladder 803 towards the wound. The approximating device 801, when used in this manner, replaces the sleeve 705 of FIG. 7A. View 810 depicts two specific forces being demonstrated. The downward force of the positive pressure bladder 803 can have multiple beneficial effects. The positive pressure bladder 803 compresses the dressing to the leg helping to insure the dressing contacts the wound and covers the uneven surface of the wound. The positive pressure bladder 803 reinforces the seal by putting pressure on the sealing layer. The positive pressure bladder 803 creates micromotion between the dressing and the wound. This micromotion allows the wound to be debrided without straining the seal. In various embodiments the motion may be on the order of <1-5 mm of motion. The positive pressure bladder 803 helps in pumping edema out of the tissue similar to a sequential compression device (SCD). The positive pressure bladder 803 prevents venous congestion and promotes blood flow in the wound similar to an SCD. The positive pressure bladder 803 pumps fluid or irrigant out of the dressing and back into the suction tubing to promote wound debridement. View 810 depicts the downward force onto the wound that is applied by the approximating device as it is pushed away from the wound. When this occurs the force is transmitted to the skin edges and pulls the skin edges in closer proximity.

A unique design feature of the approximating device is the modular aspects of the design. This aspect of the device is completely separate of any dressing component. Prior devices with similar attributes, have the wound approximating elements fabricated into the dressing itself. The design described herein separates the dressing from the approximator and allows for both to be used completely independent of each other. Prior art has a tensioner embedded into the sponge dressing. (Shuler Published U.S. Patent Application Number: US2011/0054283A1). Due to its module design, the approximating device can also be completely removed from the dressing after application to allow the seal or wound to be inspected without adversely affecting the dressing.

The outer shell and central shaft of the approximating device may be built from a plastic or polymer material. The longitudinal outer shell can be made to have some flexibility to allow the device to conform to different parts of the body and different shapes. The ribbons may be made of either a plastic, nylon, rubber or other polymer.

View 810 shows how the approximating device 801 is placed on top of the bladder 803, which itself is on top of the sealing layer and the dressing. The peripheral edges of approximating device 801 are attached to the patient's skin around the edges of the wound, e.g., with staples 805. As the bladder 803 is inflated it tends to push away from the wound surface. The approximating device 801 with its spring loaded ribbons is able to exert an inward (e.g. approximating) force toward the center of the wound. The peripheral removable fixation of the wound approximating device to the patient, prevents the bladder 803 from expanding away from the wound while also increasing the approximating force on the skin edges preventing retraction and promoting approximation of the skin.

Figure 8B:
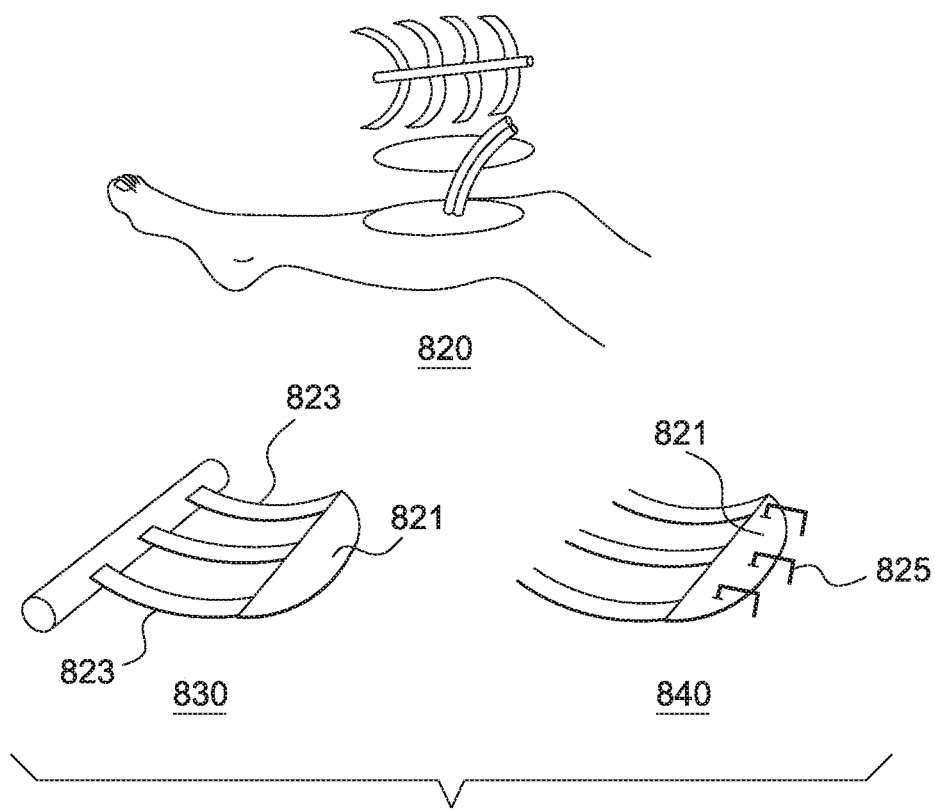

FIG. 8B depicts an embodiment of the approximating device, illustrating its ability to be attached to the skin edges. A single or multiple pull tabs 821 can be used to connect the multiple ribbons 823 that exert a force on the skin edges. In some embodiments the tab 821 is made of a soft enough material that one or more surgical staples 825 or sutures (or other fixation device) can be used to secure the tab to the skin, as shown in view 840. The tab 821 is typically positioned at the skin wound edge or further away from the edge where more healthy skin may exist. The attachment of tab 821 to the skin can be assisted through the use of adhesive on the ventral part of tab 821. Such use of adhesive can reinforce the sealing layer over the wound. A covering (e.g., peel-off papers) over the adhesive can be peeled off to allow for easy placement of the tab on the skin. The tab 821 can then be stapled into place making application quick and easy.

Figure 9A:
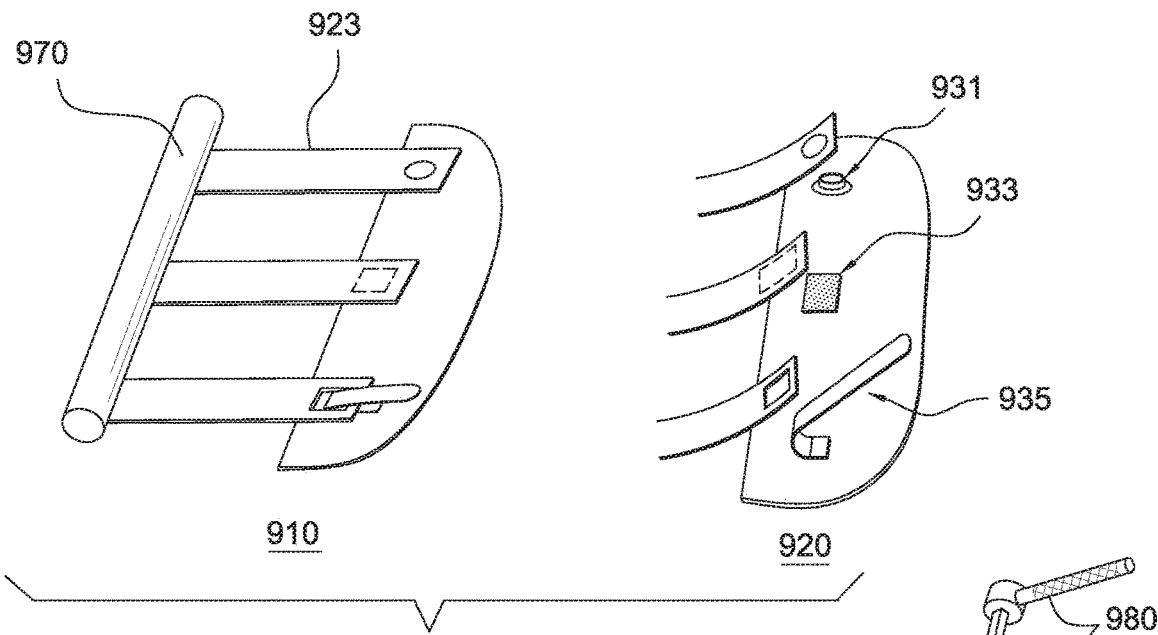
FIGS. 9A-B depict an embodiment of an approximating device.

FIG. 9A depicts multiple ways to detach the approximating ribbons 923 from the device itself. The attachment of the approximating ribbons 923 may be accomplished in a number of different ways. For example, three such means of are by use of a snap 931, hook-and-loop fasteners (e.g., Velcro™), a hook and hole fastener or a press-fit clamp that allows for the attachment point of the ribbons to be changed to any point along the ribbon. In this last embodiment of a fastening (removably affixing) technique for the ribbons, any slack in the ribbons, specifically at the ends of the wound's long axis, can be pulled through the press-fit clamp and cut to length. View 920 demonstrates three of these mechanisms used to accomplish this task. The purpose of being able to release the ribbons is twofold. The first purpose is to remove the approximating device completely. This might be needed to inspect the dressing as in a leak, the wound may be closed or there may be some concern for increased pressures within the tissue below. The second purpose may be that one area of the wound is closed and another is not. When the ribbons are all attached to the same central crankshaft, once one area is closed, that area could prevent other areas from being approximated. By being able to release specific ribbons, the closed areas can be released to allow other open areas of the wound to be approximated.

Figure 9B:
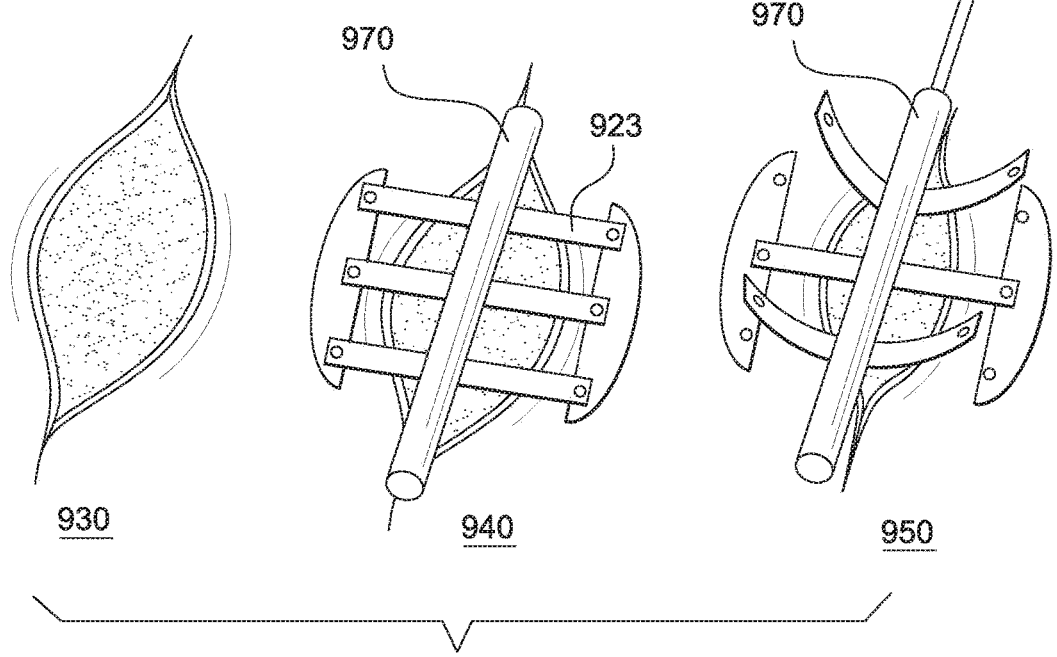

FIG. 9B depicts the support ribbons exerting forces on specific areas of the wound. In the example illustrated in view 930, the middle aspect of the wound is wider than the edges of the wound, which is a very common wound scenario. View 940 shows all ribbons 923 attached to the wound. As the wound closes down over time, the corners on the top and bottom approximate or efface. If left alone—that is, if the ribbons 923 were not detached or altered—the middle of the wound may not continue to be approximated since the ribbons 923 in the corners would prevent additional approximating forces being exerted through the central crankshaft 970 onto the ribbons removably attached to the middle of the wound. Alternatively, the corners could be pulled onto each other, over-lapping and producing a state of over-approximation. Neither of these are optimal outcomes. By releasing the top and bottom ribbons 923 as shown in view 950, the middle ribbon 923 (still attached) is now able to continue to approximate the wound edges in the middle of the wound. These ribbons are typically configured to be 0.5 to 3 cm in width, and sufficiently thin to avoid rolling up upon themselves (e.g., 0.5 to 2 mm). The ribbons may be made out of plastic, rubber, latex, polymer, nylon, vinyl, silk, or other like type of flexible elastic or nonelastic material. In another embodiment the central connection point (e.g. origin) of the ribbons to the central crankshaft 970 of the wound approximating device, can be differential, exerting more approximating force and/or resulting in greater excursion of some ribbons preferentially over others, to aim for a consistent rate of wound edge approximation and/or to avoid a pulling force on a single or few ribbons that is above a safe threshold (e.g. 10 N) for pulling on the skin margin. One means for constructing this differential approximating crankshaft 970 is by varying the diameters of the central crankshaft 970, such that the central most portion has a greater diameter and the terminal poles (e.g. the 2 ends of the shaft) have a lesser diameter, such that with each rotation of the shaft, the excursion of the central most ribbons around the shaft, and thereby the approximation of the affixed skin margins, is greater than the approximation occurring at the terminal poles. The variation in diameters of the differential crankshaft 970 is typically through construction, but could be customizable through the injection of a fluid or semi-fluid into the central crankshaft 970 at locations, in which a greater approximating force or ribbon excursion is necessary.

Figure 10:
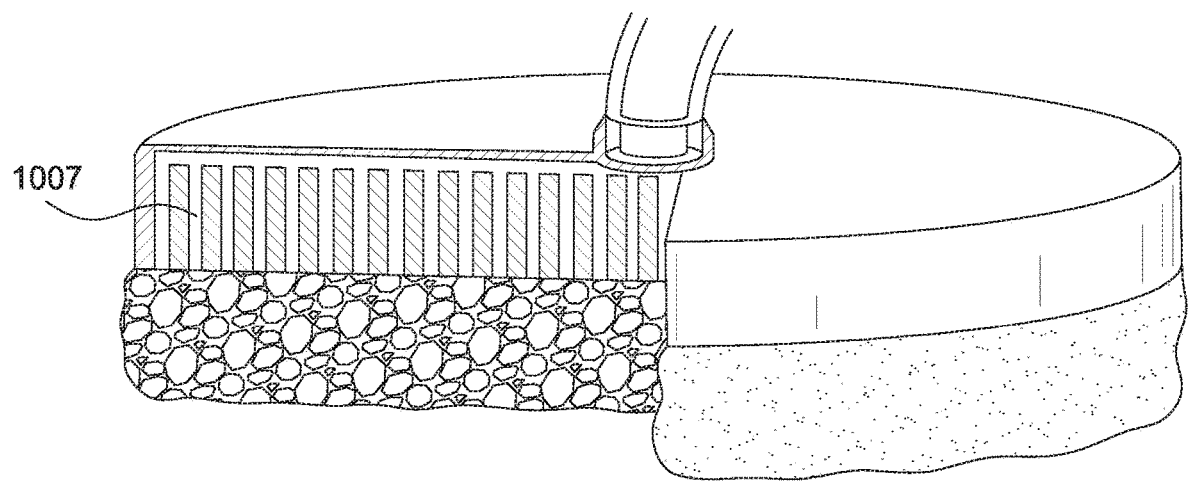
FIG. 10 depicts a cutaway view of wound interface chamber depicting multiple vacuum flow paths.

FIG. 10 depicts a cutaway view of wound interface chamber depicting multiple vacuum flow paths 1007 created by the internal risers and perforations in the peripheral (or lateral) wall and vental wall of the chamber. Some embodiments disclosed herein feature a central wound or vacuum interface chamber that serves as a communication point between the vacuum source and effluent exiting the dressing. The chamber can be a relatively thin walled, flexible closed cell, with internal risers to keep the walls of the chamber from collapsing on each other when negative pressure is applied. The material the chamber is constructed out of may be plastic, rubber, metal or polymer. The diameter of the chamber may be for <1 to 3 cm in diameter and <1 to 1 cm in height. The size may vary based on the size of the dressing. The risers may be from <1-3 mm in thickness to resist chamber compression. The ventral (facing the wound) side and peripheral (lateral) wall have multiple perforations to communicate the vacuum entering the dressing across the dimensions of the wound sealed under the dressing. This embodiment resembles a shower head, but in reverse, that is, a showerhead that projects water ante grade. This embodiment describes the retrograde flow-path for the vacuum and evacuated effluent. There is a central vacuum source connection tubing that communicates with a central cavity in the vacuum interface chamber in an airtight fashion, with a multitude of vacuum flow-paths created by the internal risers and perforations, which "showers" vacuum onto the sealed wound. Alternatively, the chamber can be composed of a solid piece of medical grade polymer with a multitude of internal pathways that come to a central point that is in communication with the vacuum source. The internal pathways are separated from each other by the medical grade polymer, which serves to add structure to the chamber and maintain a specified spatial orientation of the pathways. Lastly, the walls of the vacuum interface chamber can be thick enough and constructed of material that prevents collapse of the internal space of the vacuum interface chamber. Either of these two embodiment obviates the need for internal risers/bosses to keep the central cavity/chamber open, as depicted in FIG. 1R.

Other embodiments of the dressing have a vacuum interface flange rather than a wound interface chamber. The flange interface is devoid of a deep surface (e.g., ventral side or floor), and acts as a docking port for the vacuum source tubing to communicate with the sealed dressing. In the flange interface embodiments the area under the sealed dressing is considered a single closed space, and generally has equal pressure at all points. The single vacuum pathway in the flange is the sole source of vacuum entering the dressing and the sole path for effluent to exit the dressing. In an alternate embodiment a multi-flange system with a number of flanges arrayed in a radial pattern allows many sources of suction, as depicted in FIG. 1S. In another embodiment, the flange can be the integrated fixation point for a vacuum tubing system to the dressing. Accessory tubing can be connected to access ports constructed in either the vacuum interface chamber or flange interface, to provide additional functions, such as suction to tract-like or otherwise oddly shaped areas of the wound or island dressings that span normal stretches of skin to reach adjacent satellite wounds being regulated by a single programmable electronic vacuum regulator. The access ports can be placed either dorsal (external) to the sealing layer of the dressing, which typically is fused to the vacuum interface chamber or flange, or ventral (internal). Dorsally placed access ports, support island dressings for satellite wounds, while the ventrally placed access ports, which lie deep to the sealing layer, support the tract-like wound care. For embodiments of the MWT dressing that possess a separate irrigation tubing system or wired modules (like a wound pressure sensor) tubing and wires for these additional elements can pass through the central vacuum interface (flange or chamber) as depicted in FIG. 1C.

Figure 11A:
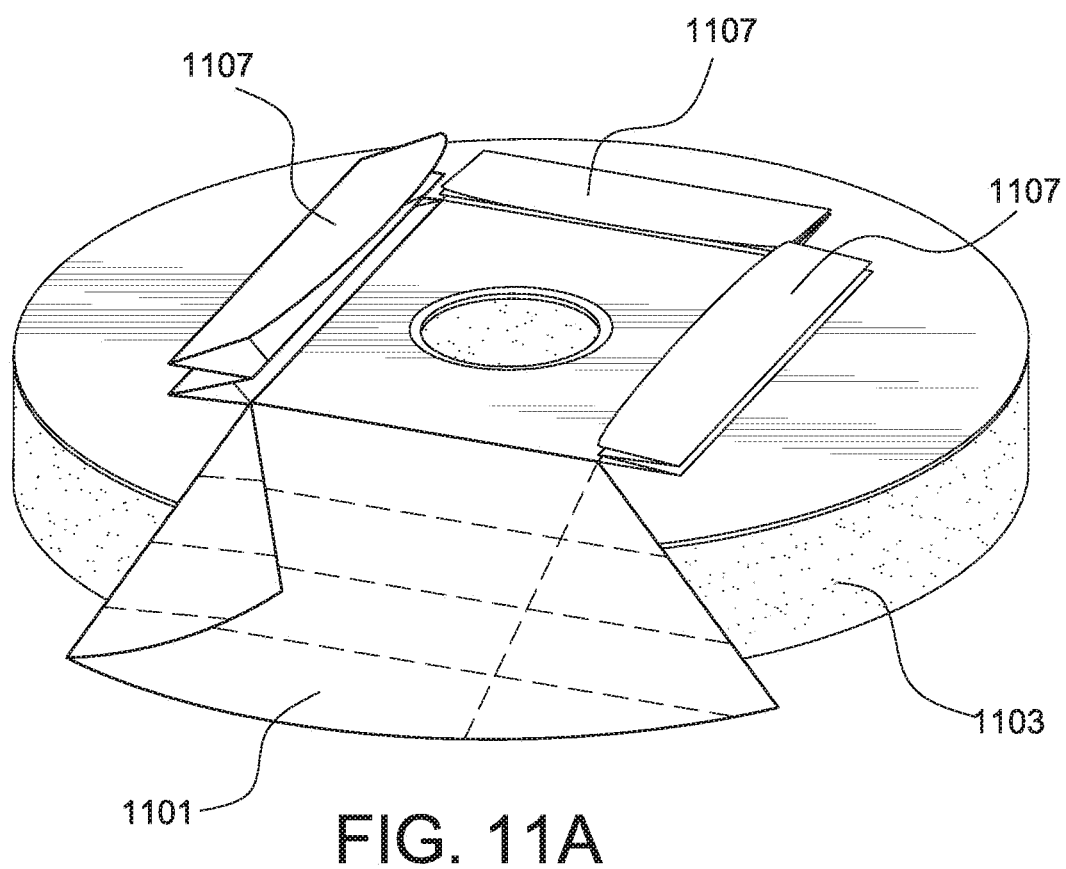
FIGS. 11A-C depict an embodiment with the adhesive covering folded and stored in a package on the dorsal surface of the unified dressing structure.
Figure 11B:
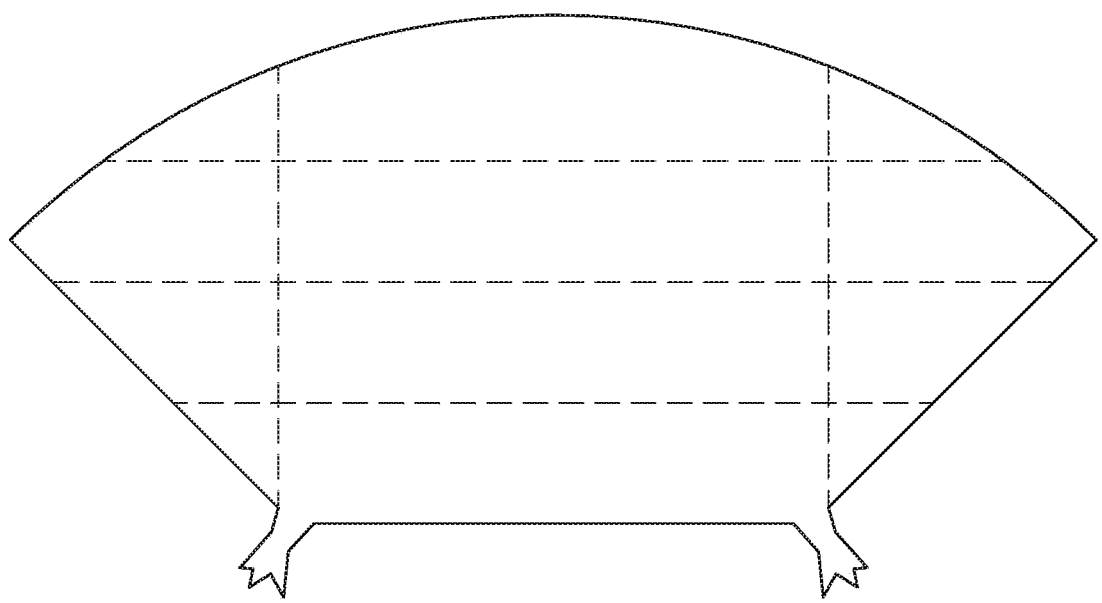
Figure 11C:
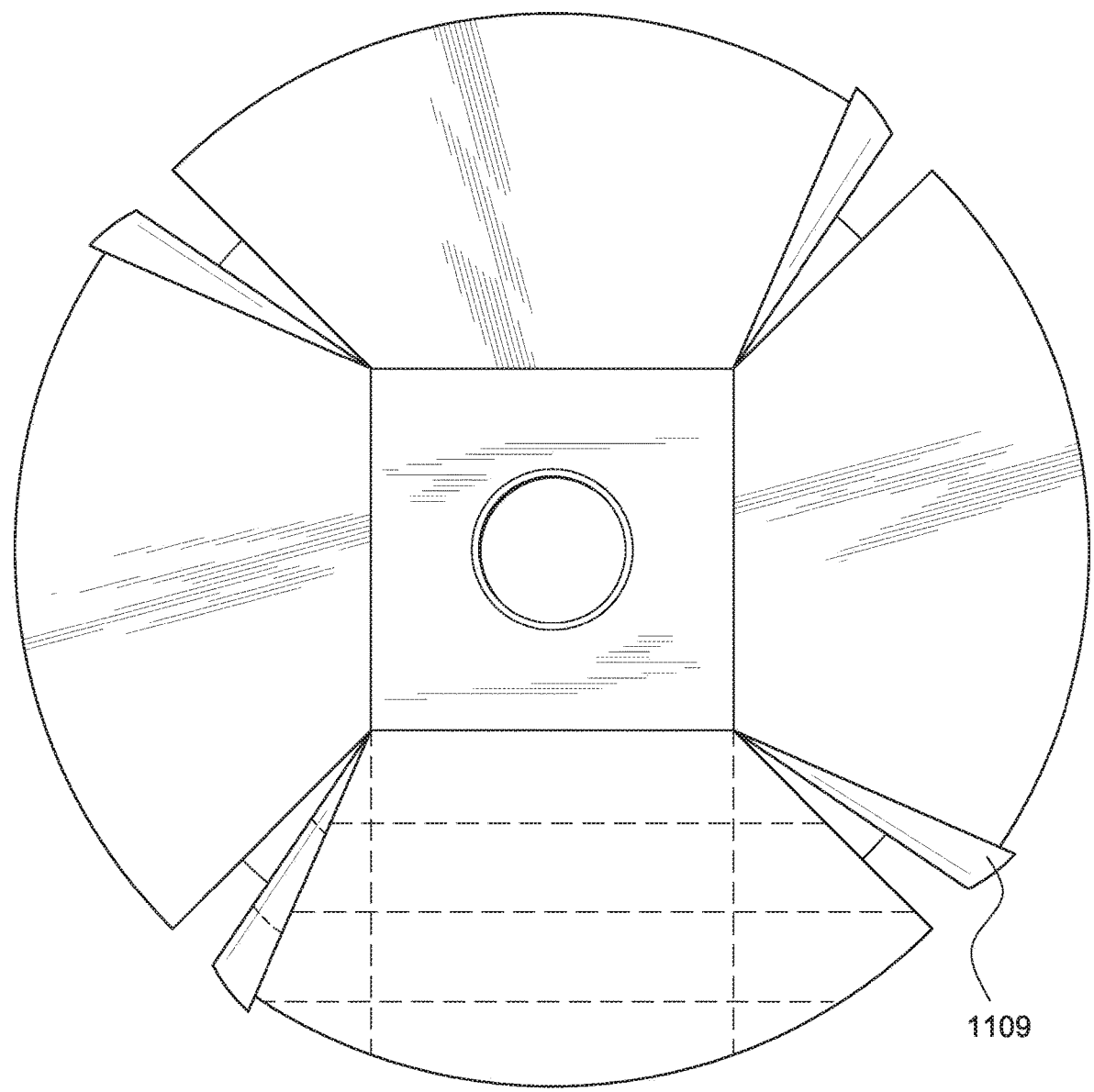

FIGS. 11A-C depicts an embodiment with the adhesive sealing sheet stored in a package on the dorsal surface of the unified dressing structure, which is centrally affixed to the dressing at fabrication. FIG. 11A illustrates a representation of the folded package embodiment of the sealing layer, which can exist over any of the MWT dressings described herein (e.g., single layer, unidirectional wound filler or multi-layered dressing). FIG. 11B illustrates one fourth of the sealing layer 1101 depicted in FIG. 11A. Element 1103 in FIG. 11A represents an MWT dressing that may be covered by the sealing layer 1101. Various implementations of the sealing layer 1101 may be configured to cover the different embodiments of MWT dressings. The dotted lines of FIGS. 11A-C represent the fold lines for folding up the sealing layer 1101. Various embodiments may be folded in different manners than that depicted in the figures, along different fold lines than illustrated, FIG. 11C depicts an embodiment with flaps 1109 configured to overlap with the next folded out portion of the sealing layer 1101. The overlapping flaps help to ensure an airtight seal over wound areas with a convex surface, or that are otherwise not on a flat portion of the patients body.

The sealing layer 1101 depicted in FIG. 11A has an "iron cross" configuration, configured to fold out in four directions. FIG. 11A depicts one of the sides in an unfolded state, while the other three sides 1107 are still in a folded state. However, in other embodiments the sealing layer may simply be configured as a single sheet folded in the midline. In folded package embodiments such as those illustrated in FIGS. 11 A-C, adhesive may be placed either on the entire ventral surface, or only the peripheral aspect of the ventral surface of the sealing layer, e.g., extending inward from the edge by anywhere within the range of 2 to 50 cm. The dressing may be cut to size, to match the dimensions of the wound. Then the sealing layer is unfolded from its central location to extend beyond the edges of the dressing, and the peel-away paper backing is removed. It is then pressed down on the dorsal surface of the dressing and then onto the skin margins. This affects an airtight seal. Adhesive sealing sheets can be placed in addition to the folded sealing layer 1101 to support and further ensure the seal is air-tight. The adhesive layer will be very thin approximately 0.1 to 1 mm thick, similar to Tegaderm™ or Ioban™. It may extend out past the edges of the dressing by several inches to allow for an appropriate seal. It can be cut down to allow specific modification to fit different types of wounds. It can have an additional reinforcing covering that can be peeled off on the dorsal surface of the dressing to prevent wrinkling during application of the adhesive sealing layer.

Figure 12A:
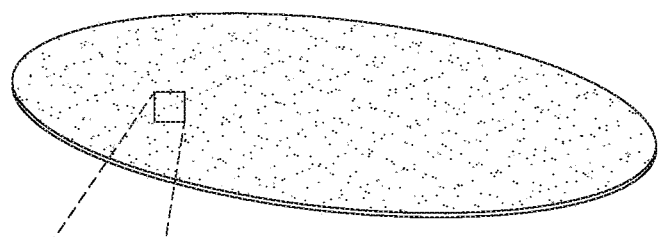
FIGS. 12A-C depict embodiments having different textures on the wound facing surface.
Figure 12B:
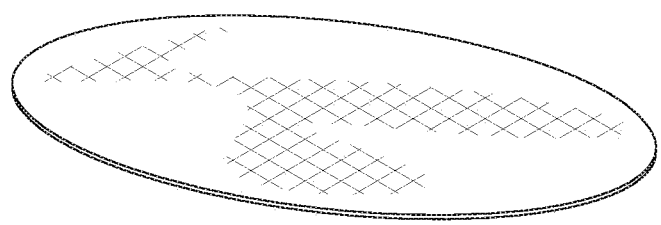

FIGS. 12A-B depict embodiments having different textures for the wound facing surface. As shown in FIG. 12A, in some embodiments the wound facing surface of the ventral most layer of the layered dressing or the netting and tubular components of the single layer dressing is configured with an abrasive surface. The abrasive surface may be made up of varying sizes from <1 to 5 mm in depth or by the mesh screen itself. The micromotion aids in the wound surface being "scrubbed" to remove dead or devitalized tissue from the surface of the wound. The ventral surface, or deep surface (e.g., facing the wound), can be constructed of an abrasive material to apply micro-abrasion to the wound surface. This micro-abrasion or micro-debridement effect is accentuated by contraction of the underlying muscle in the wound bed and by interval application of external positive pressure via a positive pressure module described herein. In other embodiments, such as that shown in FIG. 12B, the wound facing surface of the ventral most layer can be configured to have a smooth, non-stick surface. The non-stick surface is useful for placing over skin-graft sites or other reconstructed or tenuous tissue. The non-stick surface aids in reducing tissue tears/injury when the NWT dressing is removed. The non-stick surface layer can also be used in more mature, less dirty wounds, as the non-stick feature tends to cut down on pain and bleeding associated with removing NPWT dressings.

Figure 12C:
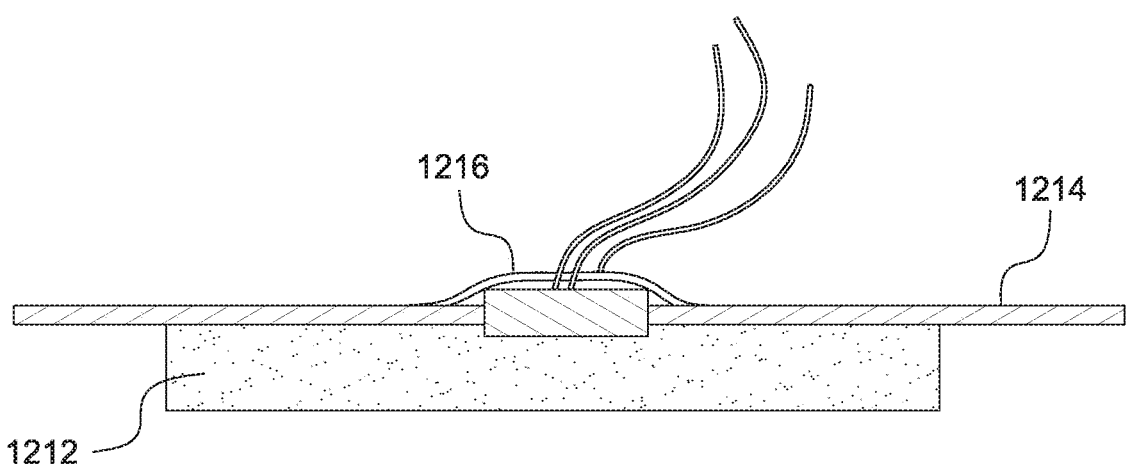

FIG. 12C depicts a unidirectional embodiment with a sponge-like ventral surface 1212 facing the wound. This may be implemented in various in MWT embodiments by using a dressing material 1212 that has a sponge-like quality. This material may be made of a sponge type material, a gauze material or fiber, a polymer or other biologically inert porous and compressible material. The depth can range from 2 mm to 2 cm based on the depth of the wound. In such embodiments the dorsal side of the sponge-like wound filler 1212—that is, the side way from the wound—typically has a fabricated air-tight coating that, on the surface facing away from the dressing, adheres well to adhesive sealing sheets 1214. This air-tight coating prevents fluids from rising to the surface in the area overlying the sponge-like filler. As such, an airtight seal between this unidirectional dressing and the skin at the margins of the wound only requires placement of impervious adhesive sealing sheets 1214 at the periphery of the dressing and onto the skin margins. The unidirectional filler 1212 can rest directly on the wound surface or above various embodiments disclosed in the layered dressing. The fabrication of an air-tight seal on a single side of the wound filler, specifically a sponge-like wound filler, produces a directionality to the dressing. Conventional wound fillers are non-directional, inasmuch as all sides have the same properties. These conventional fillers require a sealing layer, typically an adhesive film, to cover the entire dressing, not just the periphery. These non-directional fillers, rapidly become wetted while attempting to place conventional NPWT dressings. This compromises or eliminates the adhesion between the separately applied sealing layer and the wound filler, which can lead to leaks and dressing failure. The air-tight seal on the dorsal surface (away from the wound) described herein produces a unidirectional filler Such a unidirectional filler can only be applied in the correct direction on a wound.

The one-piece unidirectional embodiment facilitates application of the dressing by providing a fabricated seal to the wound filler. This seal can be applied in a multitude of manufacturing methods, like being annealed to the filler or poured over as a liquid form and allowed to dry. The depth of the seal may be from 0.5 mm to 5 mm in depth. In various embodiments the material may be a plastic, polymer, silicone, or other malleable substance to allow an airtight seal but also flexibility. By contrast, conventional systems are typically applied in two separate parts. First, the conventional wound filler (sponge pieces or gauze cut to fit the wound shape) is placed into the wound, which is generally moist. Doing this typically causes the conventional wound filler to become wetted upon application to the wound. This wetting immediately degrades the adhesive potential of the dorsal surface of conventional, non-directional wound fillers and increases the potential for system failure, through leakage or seal failure.

The one-piece unidirectional sponge-like wound filler dressings of the present embodiments incorporates either a flange or a vacuum interface chamber into the dressing. Typically, the vacuum interface chamber or flange lies within the sealed portion of the dressing or deep to the filler embodiments where the wound filler lies above a layered dressing. Additional tubing/conduits (e.g., irrigation tubing) for the specific embodiment of the MWT dressing pass through the air-tight sealing layer into the sealed portion of the wound filler. This sealed passage is typically created at fabrication, (e.g., already present when the dressing is ready for clinical use), producing a unified unidirectional dressing.

Various embodiments provide an airtight sealing layer fabricated in the manufacturing process so that the entire dorsal surface of the sponge dressing or nonsponge dressing, for example the layered dressing embodiment, does not need to be covered by adhesive film type material to be sealed—only the periphery needs to be covered by the adhesive sealing sheets to affect a seal between the dressing and the skin margins. In some embodiments, the sealing layer may not extend to the entire periphery of the dorsal surface, leaving nondirectional (e.g. able to absorb, filter, act as a flow-path for the vacuum and/or irrigant) wound filling material at the peripheral margin. This embodiment is often used in wounds with large skin flaps, in which the area of the wound is greater than that of the skin defect. The nondirectional portions of the wound filler may be cut to match the contours and depth of the wound. The dressing may then be placed into the wound such that the sealing layer lies proximate the dorsum of the wound, and adhesive sealing sheets may be used to complete the seal.

An airtight sealant or adhesive-backed airtight sealing layer is applied to the single-unit dressing, typically during the fabrication process, so that the dressing under the sealant/sealing layer is airtight. To complete the airtight seal of the unidirectional dressing (for all embodiments including those with complete or partial coverage of the dorsal surface of the dressing by the sealing layer) to the wound, adhesive sheets are added to the periphery that simply tape/seal the edges of the unified unidirectional dressing to the skin at the margins of the wound. In various implementations the system is covered on the dorsal surface by spray plastic or some airtight material to seal the dorsal surface in the manufacturing process. The airtight sealing layer made inherent to the dressing through the manufacturing process allows for ease of placement on the patient. One of the most difficult aspects of the current art is obtaining an airtight seal over the piecemeal placed wound filler around a central suction tube. Conventional system use adhesive film sheets that can fold onto themselves during application, creating folds and wrinkles which increase the risk of leaks. By fabricating the sealing layer to the dressing, the uni-directional dressing facilitates sealing to the wound margins insuring an airtight seal over the dressing itself regardless of folds or wrinkles in the adhesive sheets. Further, unlike conventional dressings which are constructed piece-meal at application, the elements needed to provide the intended clinical effect are fabricated into a single unit. This unified dressing is a substantial improvement aver the current art by overcoming the most common sources of failure for conventional systems.

In various embodiments the whole system is configured to be airtight with an apron-like peripheral extension of the dorsal most layer of the dressing (the airtight sealing layer), that extends beyond the dimensions of the dressing. In these embodiments the dressing typically lies beneath the airtight sealing layer. The airtight sealing layer is affixed to the central portion of the dressing, maintaining the single-unit, unified design. The sealing layer in the apron embodiments is significantly larger in area than the underlying dressing—(e.g. twice the area of the underlying dressing), so that the airtight sealing layer extends beyond the dressing in all directions, for example, as shown in FIG. 1P. This sealing layer could be in a similar form to Ioban™ or Tegaderm™.

In some embodiments, the sealing layer is affixed to the dressing across its entire shared area (e.g., the ventral side of airtight sealing layer overlying the dorsal side of remaining dressing elements) or only "spot-welded" at points, in other embodiments, the ventral surface (side facing the wound) of the sealing layer is covered with adhesive, which in turn is covered with peel-away paper backing, that is removed at dressing application. The wound filler/functional elements of the dressing and the airtight sealing layer can be individually cut to fit the wound, prior to removing the peel-away paper backing in the embodiments with a ventral adhesive surface on the sealing layer. This feature of separating the dressing and sealing layer except for a central fixation point allows for customization of both the dressing and the sealing layer individually but still maintain a unified dressing. In embodiments in which the airtight sealing layer is not affixed continuously or at multiple points (e.g., spot welded) through fabrication to the dorsal surface of the dressing, the dressing is separate from the airtight sealing layer at all points, except for the central fixation site. This central fixation site is typically within the 2-6 cm diameter reinforced central area (e.g. vacuum interface chamber) at the dorsal surface of the dressing through which connecting tubes enter the dressing in a sealed fashion. This airtight linkage of tubing to dressing is typically created at fabrication, in keeping with the unified dressing concept.

In some embodiments an adhesive-backed airtight sealing layer is folded away from the dressing layer in order to cut the dressing to size. Once the dressing is cut to the proper size and shape, the sealant layer can then be unfolded, the peel-away paper backing removed, and the adhesive sealing layer can be affixed over the remaining portions of the dressing, and then affixed to the skin at the wound margins, thus creating an airtight seal. Prior to this, the adhesive-backed airtight sealing layer can also be cut to fit the shape of the wound margins. In other embodiments, the adhesive portion of the sealing layer is not present centrally, but only at the periphery. In an apron-like embodiment with the apron affixed in an airtight fashion by adhesive and/or fabrication centrally and affixed to the periphery of the dressing and normal skin margins via adhesive, which is initially covered with peel-off paper backing. The apron is free of the underlying dressing at the periphery, which allows the dressing to be cut to the dimensions of the wound, without cutting the apron. The apron can also be cut to match the shape of the wound. The apron is typically longer in all dimensions than the dressing by at least 1 inch. This over-hang is the surface area that will cover and stick to the skin margins, when the peel-off paper backing is removed and the apron is sealed to the patient to affect an airtight seal. Other apron-like embodiments, do not have adhesive on the ventral side, but a tacky substance on the dorsal side. This is intended to provide a better surface for applying adhesive sealing sheets to seal the dressing to the wound margins.

Figure 13A:
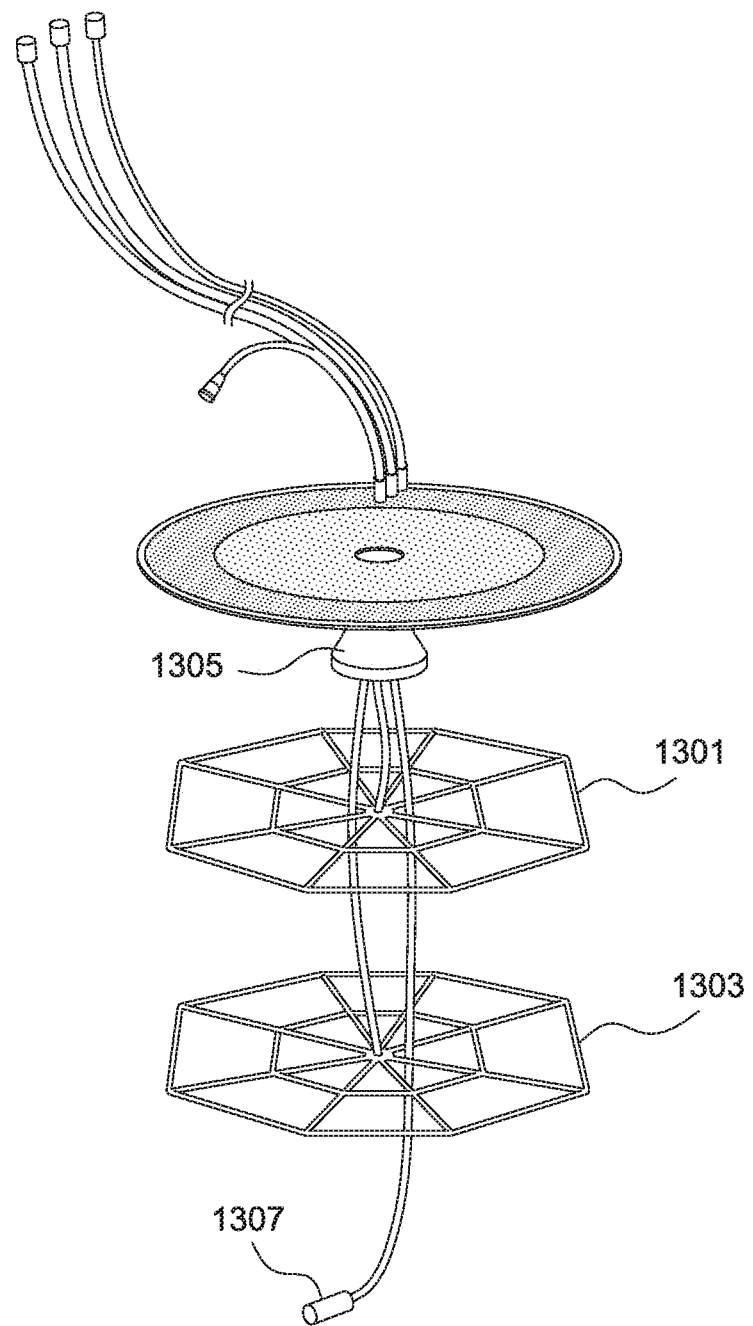
FIGS. 13A-C depict embodiments of vacuum and irrigation tubing systems for an MWT dressing.

FIG. 13A depicts an embodiment of a basic MWT dressing that uses both a vacuum tubing system 1301 and a separate, dedicated irrigation tubing system 1303. In the embodiment of FIG. 13A the individual perforated tubes of the tubing system are interconnected in a web-like pattern. There are two completely separate in-flow and out-flow circuits are depicted. The portions of the in-flow and out-flow circuits closest to the wound surface are tubing systems. The vacuum tubing system 1301 lies dorsal to the irrigation tubing system 1303. The wound pressure sensor 1307 is positioned directly at the wound surface.

The embodiment of FIG. 13A features a dual tubing system in which the vacuum tube circuity 1301 is independent of the irrigation tube circuitry 1303. In the embodiment of FIG. 13A the vacuum interface chamber and irrigation tubing system are independent and not coplanar—that is, the vacuum interface chamber 1305 lies dorsal to the irrigation tubing system 1303, which lies on the surface of the wound. In yet other embodiments, for example, the embodiment depicted in FIG. 13C, the vacuum lines 1321 and irrigation lines 1323 are co-located within the same layer. In some embodiments the vacuum and irrigation lines are strictly coplanar, within the same plane. But in other embodiments they may have non-planar connections, that is, crossing over each other to achieve an even dispersal of irrigant delivery and vacuum evacuation, as shown by the dotted line 1325 in FIG. 13C.

The design of the tubing systems ultimately requires the irrigant to travel across the wound surface to reach the vacuum outflow. The path of least resistance, which is ultimately the path in which the fluid will travel, crosses over the wound. By fixedly separating the areas for delivery and removal of fluid, the fluid is required to travel over the wound aiding in irrigation and cleansing of the wound. This dual tubing concept is novel in design and function. Other embodiments feature a single tubing network, rather than a dual tubing network.

Figure 13B:
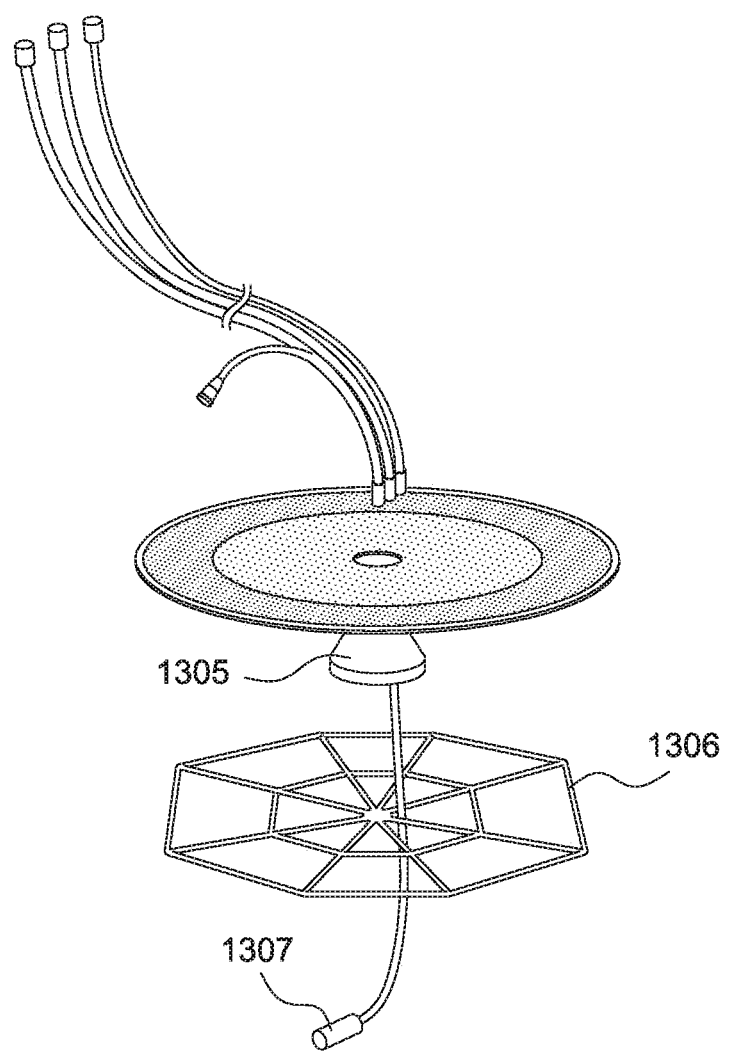
Figure 13C:
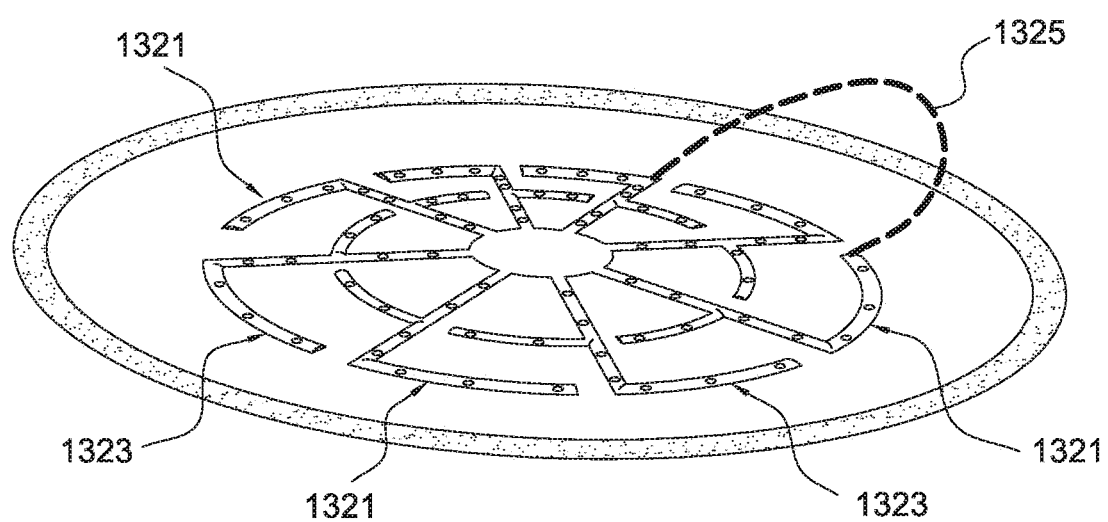

FIG. 13B depicts an embodiment of a single layer dressing in which the in-flow circuit is the only side with a tubing system 1306. In this embodiment vacuum reaches the sealed dressing through the vacuum interface chamber 1305, without a vacuum tubing network.

Returning to FIG. 13A, in various embodiments the irrigant and vacuum tubing systems are individually controlled or controlled in groups, so as to activate the whole dressing or selected portions of the irrigant and vacuum tubing systems. In some embodiments the irrigant tubing system over the whole wound or a portion of the wound may be turned on while the vacuum tubing system over the whole wound or a portion of the wound are also turned on. The remaining irrigant and vacuum tubes may be selectively turned off. In this way, a portion of the vacuum circuit can be turned on while another portion of the irrigant is operating so as to direct the flow of fluids across the wound from the irrigant lines to the vacuum lines. This allows the caregiver to tailor the rate of irrigation and vacuum for those portions of the wound needing such attention.

In accordance with various embodiments of MWT, irrigation tubing system may be configured to lie proximate of the wound surface (e.g., within 1 mm, or within 1 layer of netting). This can be seen in FIG. 1C in which the irrigation tubing is positioned sandwiched between layering material, which is netting, mesh or a thin perforated film. In this configuration, the irrigation tubing system is the ventral functional element of a layered basic MWT dressing. The irrigation tubing system delivers an irrigant which can be sterile or potable water or other cleansing or adjuvant therapeutic fluids or gases. The irrigant can be delivered under pressure either from an irrigation pumping system or through reverse pulse lavage, in which bursts of vacuum are applied to a one-way valve controlled, gravity fed irrigant source. In some embodiments the irrigation tubing has a port configured to receive injections of therapeutic fluid dosages. The layered dressing design aids in maintaining the spatial relationship between the irrigation tubing and the vacuum tubing or vacuum interface chamber/flange, such that the irrigation system is held close to the wound surface with perforations in the tubing of the irrigation system directed towards the wound. By fixedly maintaining the position of the tubing, the spacial relationship between irrigant delivery and removal is maintained. There by providing the greatest assurance that irrigant passes over the surface of the wound, assisting in cleansing of devitalized tissue and bio-burden from the wound bed.

In some embodiments there are no perforations in the irrigation tubing other than at the terminal extent of each limb of the irrigation tubing system when it is arranged in a radial pattern, which acts to deliver the irrigant to the periphery of the wound, allowing the irrigant to travel across the wound surface as it is suctioned from the wound via the centrally located vacuum interface or separate vacuum tubing system. These combined design features mean that irrigation will be directly applied at or near the wound surface where it can cleanse the wound and reduce fibrin slough and biofilm formation. Since, in various embodiments, the irrigation tubing system is completely separate from the vacuum source, these two functions can be paired to optimally irrigate the wound surface while helping to prevent the formation of pooled fluid. Likewise, the reverse pulse lavage mode, can simplify the system, by eliminating a need for a positive pressure irrigant pump. A control valve may be placed in the irrigation tubing circuit, to allow flow in response to negative pressure being applied at the level of the dressing. Distal to this control valve is a crimp, or similar device, configured to keep the irrigation line closed so that irrigation is only provided when intended, e.g., when the crimp is removed to open the line. The control valve and/or crimp can be operated manually or electronically. In embodiments with electronically operated distal control valves and/or crimps, the EVR typically regulates the setting of these control features. Different modes of therapy that call for specific sequencing of vacuum and irrigation, can be programmed into the EVR during manufacturing or custom modes can be programmed by the end-user.

In some embodiments, the irrigation and vacuum connection tubing have access ports proximal to the tubing connection point with the basic dressing, allowing connection to a separate dressing or wound site. Y-shaped tubing with slip-fit connectors, or other types of connectors, can be connected to the branched portion of tubing to make a multitude of splits in the primary vacuum and irrigation tubing, to allow coverage of multiple wounds.

Another embodiment allows the device to intermix a gas into the irrigation line. By alternating fluid and gas, the suction driving the passage of irrigation allows gas to "clear the system" and prevent fluid pooling or back flow when the dressing is not being suctioned, e.g., as described in FIG. 3A. The vacuum burst is applied, for the first half of the burst time period it pulls fluid across the wound, the second half of the burst it pulls a gas across the wound. This embodiment allows the irrigant to be pulled across the wound and removed from the dressing preventing fluid pooling and seal disruption.

The novel dual-tubing vacuum/irrigation system of the various embodiments disclosed herein helps to prevent pooling and effectively replicates the low-pressure lavage techniques which have been proven beneficial in the treatment of wounds. Unlike operative lavage, which typically can only be performed once per day at most and requires a trip to the operating room, the irrigation therapy of various MWT embodiments can be performed as many times per day as the provider prefers, or continuously.

Various embodiments include a biocompatible polymer/plastic netting, mesh or thin perforated film. Some layers may be impregnated with antimicrobial agents, like antibiotics or silver or with bioactive molecules (e.g. cytokines in the transforming growth factor-beta family). Others may use one or more bioabsorbable netting, mesh or thin perforated film layers which can have varying absorption rates per layer. These layers can vary in thickness from 1 mm to 1 cm based on the desired time of absorption. Possible materials are Polyhydroxyalkanoate (PHA), Poly(lactic acid) (PLA), Polycaprolactone (PCL), Polyesteramide (PEA), Aromatic copolyesters (e.g. PBAT), Aliphatic copolyesters (e.g. PBSA), or Polyglycolide or Polyglycolic acid (PGA). The use of bioabsorbable layering or wound filling material is well suited for tissue engineering applications and/or extended duration use. Likewise, at least one embodiment uses all bioabsorbable layering material in the layers of the dressing, such that as the wound dimensions are closed, specifically with the assistances of the wound approximating device module described herein, the netting, mesh or thin perforated film layer can be absorbed, leaving only the vacuum/irrigation system functional elements and in some embodiments additional monitors/adjuvants, which will fold on themselves. Further, while the netting, mesh or thin perforated film based dressing is designed to overcome the flaw of conventional dressings which can leave dressing debris in the wound bed at changes, the bioabsorbable construction of some or all of the netting, mesh or thin perforated film layers can further overcome this flaw. If a piece of the netting, mesh or thin perforated film is left behind, it will harmlessly absorb, similar to absorbable sutures in a wound.

Various embodiments of the netting, mesh or thin perforated film layer can be composed of completely bioabsorbable materials that can be impregnated with antimicrobially active agents (e.g., antibiotic powders or the like) and biologically active agents (e.g., pluripotent cell, TGF-B, BMPs, or the like). A "bioabsorbable material" eventually dissolves and is absorbed by the body. The interface can act as a bioactive scaffold that draws healing cells into the matrix to create layers of new tissue over the exposed depth of the wound. These embodiments may be best suited for open wounds over-lying expose bone, tendon or other vital extremity tissue, which needs direct soft tissue coverage prior to skin grafting or allowing the wound to be treated in a traditional fashion with cotton dressings to secondary intent. In another embodiment, the deepest layer of the dressing can be composed of a biologically well tolerated material that is smooth on its ventral surface. During manufacturing cultured tissue or allogenic tissue can be approximated to this ventral layer so as to stay removably affixed during the process of applying the dressing to the wound. The tissue layer is typically collagen-based, to serve as a substrate for local host tissue in-growth. It may be impregnated with cultured cells or biologically active agents, like cytokines. When impregnated with biologically active agents, the concentration of the agent can be titrated geometrically, so as to establish a concentration gradient that helps to select and direct host tissue response. In some embodiments, the tissue layer can be composite tissue (e.g., full or partial thickness allogenic skin). The smooth ventral most non-absorbable layer of the MWT dressing, serves to allow safe separation of the dressing from the tissue layer, after a prescribed period of MWT care to the wound, typically 5-7 days. By this construction, the new integrated/transplanted tissue layer, will remain affixed to the wound bed, to which it is or will become biologically incorporated.

A biological dressing such as allograft skin or collagen matrix may be attached to the ventral aspect of the dressing creating a composite MWT dressing. A composite dressing with a human tissue or tissue substrate can be affixed to the composite dressing to aid in avoiding the need for autograft. This composite dressing can, in some embodiments, be a second phase dressing made to allow for wound coverage without the need for autogenic grafting. Once a stable clean wound bed has been obtained, a second composite wound coverage dressing can be applied. This composite wound coverage dressing may have a biological substance on the ventral side of the dressing. In some embodiments the biological layer may be removably affixed to the dressing—e.g., a non-biological MWT dressing—via a biodegradable fixative or by simple fluid adhesion. The fixative used to hold the layers together may be configured to degrade over various predefined ranges of time, e.g., from a period of hours to days, or even weeks in some situations. The NPWT tends to compress the biologic substance to the wound surface increasing the likelihood of incorporation. Once the biologic layer has been incorporated the dressing is removed. The fixative has degraded leaving the dressing separate from the biologic layer that is now attached to the wound surface creating a covered wound without autogenic grafting.

The netting, mesh or thin perforated film can be configured to be placed in multiple layers in order to produce the desired thickness. Depending upon the implementation, the layers can be laid upon each other either in parallel, perpendicular to each other, or with small amounts of angular rotation between layers, e.g., as shown in FIG. 1F. While this layering can be performed in-situ, the typical embodiment has a set number of layers fused or otherwise permanently affixed to intervening functional elements or spacers, and through these connections, be indirectly affixed to each other, so that the dressing is a single unit. In some embodiments the fused layers are configured such that one or more of the outside layers can be removed in order to vary the thickness of the layer assembly. The various layers can be separated by functional elements of the dressing and/or spacers of a predetermined width. Spacers and functional elements allow for the dressing to be constructed to an ideal thickness, while maintaining pliability (to follow the irregular surface of the wound) and collapsibility (to allow the elements contained in the layered, single layer or unidirectional wound filler dressing, to collapse on themselves to facilitate, rather than hinder, the device assisted and biologically inherent process of wound approximation. In lieu of spacers, additional monitors (like pressure, pH, O2, NIRS sensors or camera) can be placed in specific locations to monitor the health of the wound. Typically, the dorsal most and ventral most layering material has special characteristics to improve functionality of the dressing. The dorsal most layer typically has an air-tight sealing layer applied at fabrication to its dorsal surface. The ventral most layer typically has an abrasive ventral surface that contributes to micro-abrasion of the wound bed. In some embodiments, the ventral most layer may be smooth or non-stick, to prevent adhesion to the underlying host tissue. The size of the open spaces or pores in the netting, mesh or thin perforated film, can be adjusted through manufacturing to encourage or discourage specific biological host response, such as tissue in-growth.

The netting, mesh or thin perforated film provides a plurality of flow paths for fluid suctioned from the wound and irrigation to the wound. Between the layers, plastic material/strips can by placed as spacers, that maintain the plurality of flow paths, while adding substance, depth and form to the dressing material, such that it can hold its shape and more easily be cut to size, when it is customized to an individual wound.

At least some embodiments of the system are suitable for serving as a bridge dressing, to be used at the first or early surgical debridement procedures for particularly dirty or otherwise challenging wounds, in which serial surgical irrigation and debridement procedures are deemed necessary by the treating physician. The bridge dressing embodiment is a stripped down version of the multi-functional MWT dressing, possessing in its most simplest form only a vacuum source (vacuum interface or tubing system with or without accessory tubing), with or without a wound pressure sensor. This novel dressing is intended to serve as a bridge between presentation and gross surgical decontamination. The layers of netting, mesh or thin perforated film in this bridge dressing may or may not be separated by plastic spacers or functional elements. The dorsal surface may or may not be sealed. When it is not sealed, the bridge dressing is multi-directional, in that it can apply vacuum and/or irrigation in all directions. The wound side surface may or may not be abrasive.

This bridge dressing is often used for shorter durations of time (e.g., 24-72 hours), in situations where the surgeon or care provider feels the wound requires serial sharp debridement and irrigation. Such care may be rendered during in-office care, hospital settings or the operating room, prior to achieving effective gross surgical decontamination. At that point, the multi-functional MWT embodiments are typically implemented until the wound is ready for delayed primary closure or other form of definitive treatment. In some cases, these simplified bridge dressings will be the sole dressing used for 1401 the extent of MWT therapy, often in smaller, less complicated wounds.

Figure 14:
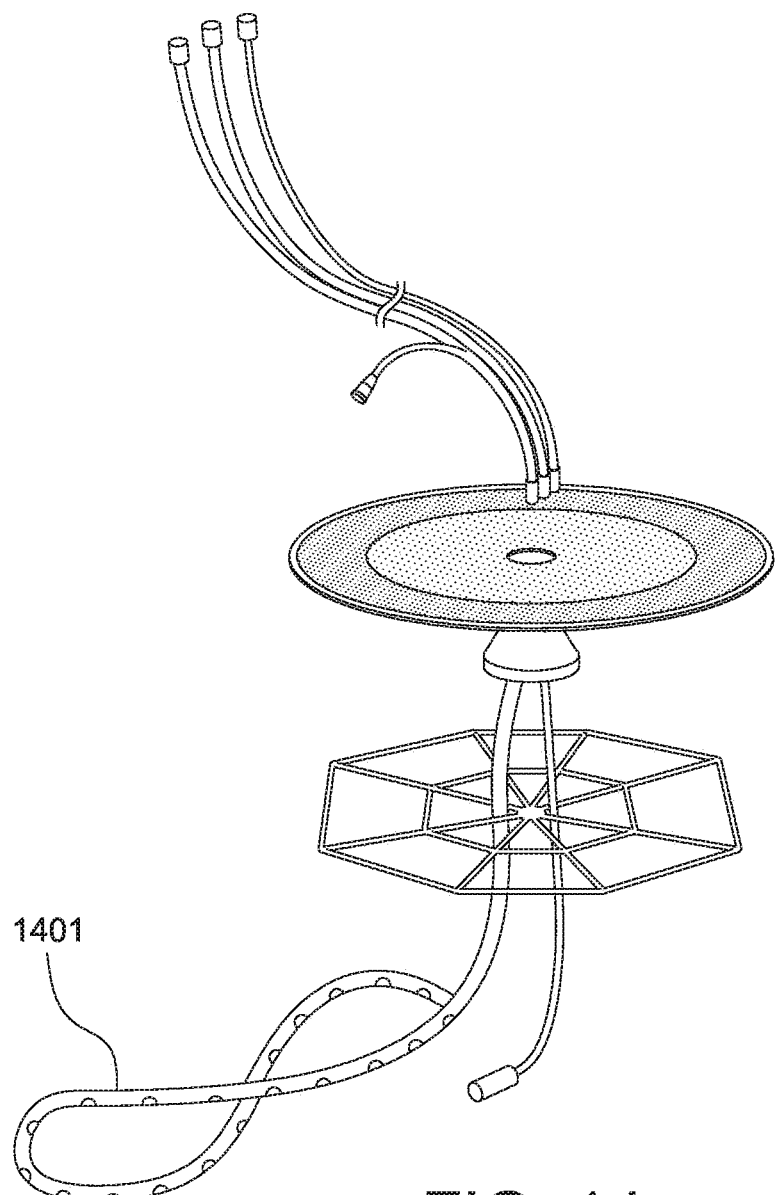
FIG. 14 depicts an embodiment with an accessory tube.

FIG. 14 depicts an embodiment with an accessory tube 1401. Various embodiments are configured with one or more accessory tube(s) 1401 that extend from a central point off of, in addition to, or in lieu of, a vacuum interface chamber/flange or an irrigation tubing system. The accessory tube(s) 1401 may be used to convey only vacuum, only irrigant, or multiple accessory tubes 1401 may be used to convey both vacuum and irrigation. In some implementations the accessory tube(s) 1401 are simply straight tubes, while in other implementations the accessory tube(s) 1401 are configured in a figure-eight fashion, in which one flow-path is dedicated to vacuum and one flow-path is dedicated to irrigation, as shown in FIG. 14, or like type of design. Accessory tubes serve two primary functions, (1) conduits to bridge dressings or (2) independent functional elements (e.g., vacuum/irrigation flow paths) that can be directed into tract-like areas of the wound or partially or completely surgically closed (e.g., sutured) areas of the wound. When acting as an independent functional element, the accessory tube can have an ending portion that is flat, round or another shape conducive to draining or delivering irrigant to a portion of the wound. An additional configuration includes multiple loops of this tubing with a central communication point that produce a more bulbous effect, to fill cavitary lesions, e.g., as shown in FIG. 4.

The accessory tube(s) 1401 of FIG. 14 are typically of sufficient length to be laid into elongated, narrow tracts within the depths of the wound (e.g., gunshot tracts), that are not well treated by current forms of NPWT dressing. Accessory tube(s) 1401 aid in preventing narrowed, more superficial areas of the tract from closing, leaving a dead, potentially dirty, space in the depth of the wound that is not in communication with the vacuum source. In one common use, the accessory tubing 1401 is configured as a single function tube interconnected with the vacuum circuit. The system is configurable so that one or more accessory tubes can branch off the wound interface chamber/flange, delivering directed vacuum to tract-like wounds or to serve as a conduit to accessory dressings.

In another additional embodiment, the accessory tube is the single flow-path between the regulated vacuum source and the patient. In this instance, the accessory tube typically looks like a standard closed surgical drainage tube (e.g., a 10 French Jackson-Pratt drainage tube), and the draining end of the tube is placed into the wound or operated portion of the patient, for instance the knee joint after a knee reconstruction, and the conduit end of the tube connects to the vacuum connection tube, which connects to the collection canister and EVR/vacuum source. This embodiment represents an automated version of the common closed surgical drain, which typically applies suction through deforming the shape of the collection canister, and allowing recoil of a spring (HemoVac) or the collection bulb itself (Jackson-Pratt drain) to produce the negative pressure in the closed system. A clinical benefit of the automated closed surgical drainage technique described herein, is that the flow can be measured automatically using a flow measurement device and downloaded directly from the EVR to the electronic medical record. Alarms or feedback can be programmed in the EVR that alert the provider when certain total volumes or volume rates are exceeded. Further the level of vacuum can be strictly regulated with this technique, versus the recoil techniques mentioned. Additionally, the drain may have a one-way valve to prevent back flow at the junction of the drain and vacuum connection tubing.

The accessory tube(s) 1401 may also serve as conduits for special bi-directional versions of the netting, mesh or thin perforated film dressing that can be placed into deeper planes of the wound. These accessory dressings are constructed as simple bridge dressings as described above. They can have a radial (e.g., centripetal or Christmas tree like) or spider-web tubing system with or without netting interspaced between the limbs of the tubing system, that can direct vacuum flow alone or with a dedicated irrigation tubing system to these deeper, undulating areas, where two-chamber conditions are most likely to form, in which small pockets of the wound can self-seal and the new closed space can be separated from the negative pressure applied to the larger portion of the wound. In the accessory dressing, a radial or spider-web vacuum tubing system and/or plastic spacers will typically be secured ("sandwiched") between the layers of the dressing, with or without additional layers separated by plastic strips, one or more support members, or irrigation tubing. Typically, neither surface would be sealed (e.g., bi-directional), but rather, would be available to suction wound fluid and deliver irrigant, with or without roughening of the surface in all directions.

A potential additional use of the accessory tube and bridge dressing is to treat less severe satellite injuries from a major wound that is being treated with a multi-functional MWT dressing. In this situation accessory tubing connects the vacuum interface of the primary multi-functional MWT dressing via an airtight port on its dorsal surface with the bridge dressing. A similar accessory tube can be removably connected the irrigation connection tubing to an irrigation layer in the bridge dressing, if irrigation were to be provided, as well. The accessory tubes, are dorsal or outside of the sealing layer of the primary NEWT dressing. Ports just dorsal to the seal for both vacuum and irrigation allow for a series of dressings to be regulated by a single EVR, producing serial dressing therapy. Cross contamination of wounds may be prevented through the use of the one way valves that prevent backflow, e.g., as shown in FIG. 5A. One specific embodiment of this primary wound/satellite wound dressing would be a fasciotomy specific dressing, which has a primary MWT dressing that covers the larger open fasciotomy wound, on the lateral leg for instance, while the contralateral fasciotomy wound is closed, typically the medial side of the leg. This special embodiment, has a standard multi-function MWT primary dressing, with an accessory tube that ends in a configuration that is most similar to a long flat drain (e.g., similar to a 10 French Jackson-Pratt flat drain). The flat drain appendage is placed in the contralateral wound, and that wound is closed over the drain. This provides active, regulated and metered drainage of the freshly closed wound, while the primary wound is being prepared for closure or coverage under the multifunctional MWT dressing.

In cases, where it is desired to route irrigation and suction to deeper planes of the wound the accessory tubes 1401 can be configured to include tubes for both the irrigation and vacuum functions. For example, the accessory tube(s) 1401 may be configured in a figure eight design—that is, two separate tubes fused together to provide separate irrigation and vacuum lines. The two lines may extend from a central tubing connection point out about 6 cm or longer. In some situations, perforations in each tube 1401 are configured to point away from each other, to maximize the distance irrigation must travel to reach the vacuum out-flow tube. In one implementation the irrigation side may have fluid passage holes that do not start until 2 cm or more distal to the central connection point. In similar implementations, the vacuum lines may only have perforations more centrally located, so as to prescribe a flow-path from peripheral to central across the wound surface. In some situations the full length of the tube may be used, as is, to fill deep tracts. In other situations the tube can have no perforations e.g. akin to conduit tubing) in its walls and be cut to the length needed for the wound, and connected to accessory dressings possessing separate vacuum tubing and irrigation tubing layers.

The accessory tube(s) 1401 may be configured to slip over, or fit on to, or by some other mechanism fluidically connect to short segments of tubing from the irrigation and vacuum system in the accessory dressings. In this way the accessory tube(s) 1401 connect to accessory dressings maintaining dedicated fluidic flow paths for vacuum and irrigation from wound surface to the collection canister or irrigation source (FIG. 5A). Bi-directional accessory dressings can be placed in deep planes, larger than what is best addressed with only a simple figure-eight shaped tube, thus extending MWT function to all aspects of these complex wounds. This is particularly useful in the treatment of large combat wounds or traumatic amputation stumps, in which multiple potential dead spaces occur between large flaps of muscles. One current method is to place sponge or gauze dressing into these blind, deep spaces, which does not guarantee full coverage of the space, but most importantly can lead to not only micro-debris from the sponge or gauze, but macro-debris, from entire pieces of the conventional dressing material being left in these spaces at serial dressings.

Dressings that do not use conventional wound filler materials in some embodiments may be composed of tubing that may or may not be inter spaced with netting material, in which the wound facing ventral surface has an abrasive surface, that can micro-abrade the wound and assist in mechanical debrided. The non-wound filler dressing may be configured to have a netting material or thin perforated film that connects between limbs of the single layer tubing dressing to present one single planar surface. The netting portion may also have an abrasive surface against the wound to provide a debridement function, e.g., as shown in FIG. 1L. In layered dressing embodiments, the ventral most layering material can also have an abrasive ventral surface to produce a micro-abrasion effect.

Figure 15:
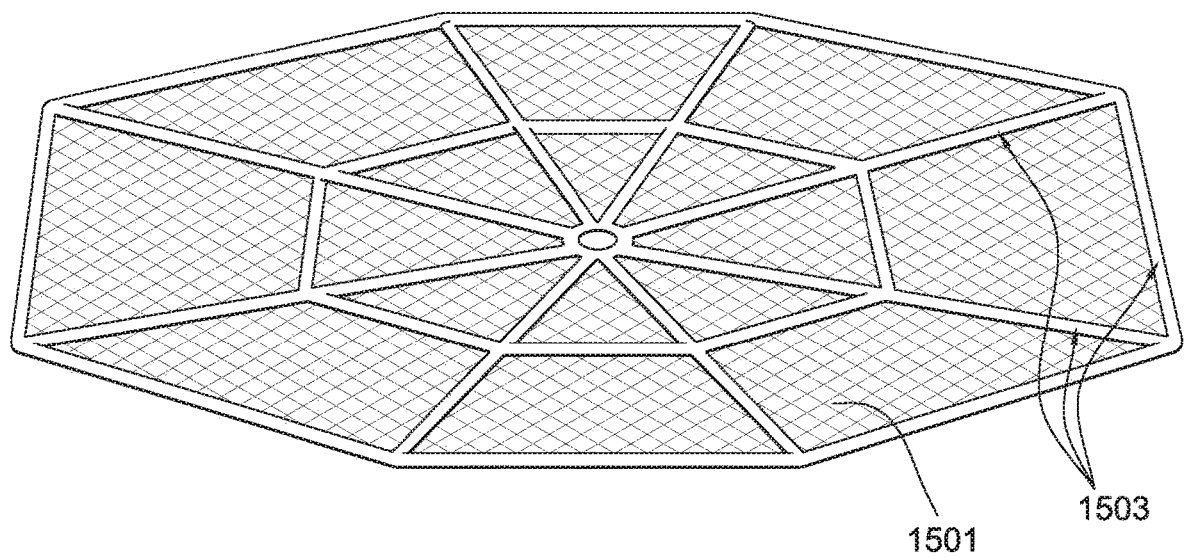
FIG. 15 depicts an embodiment of a vacuum and/or irrigation tubing system configured with netting or thin perforated film disposed between the sections of tubing.

FIG. 15 depicts an embodiment of a vacuum and/or irrigation tubing system configured with netting or thin perforated film 1501 disposed between the sections of tubing 1503 in the vacuum or irrigant tubing system. In some embodiments the netting or thin perforated film 1501 spanning between the tube components 803 is composed of a material that is not susceptible to decomposition, for example, a metal, plastic or other synthetic material that does not break down in the presence of fluids or other wound conditions.

In other embodiments the netting 1501 spanning between the tube components 1503 is composed of biodegradable, hypoallergenic materials. In this way, if any such netting material becomes trapped in the wound granulation tissue, it will not be a permanent foreign object that could lead to chronic inflammation or infection. In some embodiments the netting layer 1500 can also be composed of nonstick, low coefficient of friction materials. The smooth/nonstick surface is ideal for being placed over grafts, bioengineered tissue or other tenuous tissues, to reduce the shear stress during wear and the adhesion stress during removal.

NPWT has been used over top of skin grafts to compress the skin graft down to the recipient bed while also removing potential hematomas that limit graft take. Some embodiments feature a dual-sided layering material with one side comprising an adhesive and the other side comprising a nonstick, low coefficient of friction material. This add-on/modular nonstick layer may be placed on the ventral side of a basic MWT dressing to convert an abrasive surface to a slick, non-stick surface. The nonstick side of the special layering material now becomes the ventral surface, nearest the wound, of the unified basic MWT dressing. The nonstick, low coefficient of friction aspect of the layering material facing the wound tends to reduce shearing stress and adhesion of the dressing to the skin graft or underlying tissue. Some configurations feature two layers interspaced by springs, bearings or lubricant that prevent or attenuate shear forces applied to the dorsal aspect of the dressing from being transmitted to the skin-graft recipient site or wound bed. In some embodiments, a separate nonstick layer of low coefficient of friction material, can be placed on the skin graft, allowing a gliding action between this layer and the dressing. Skin graft dressing may be a separate special dressing. In alternate embodiments, the ventral most layer of the unified layered dressing is not abrasive, but rather, is configured to have a slick or nonstick ventral surface to reduce shear and adhesion forces over skin grafts.

A complete MWT wound care system tends to extend the useful wear time of the dressing. Conventional NPWT dressings must be changed every 24-72 hours. Unfortunately, this is not sufficient time for many wounds to heal to the point of being ready for definitive soft tissue management. This is a weakness of conventional systems which demand the frequent dressing change schedule, an exercise that is costly in both supplies and labor, and quite painful to the patient. Frequent dressing changes also expose the wound to potential nosocomial pathogens which can be more virulent and/or difficult to treat than the microbes which initially inoculate a wound at time of injury.

One advantage of an MWT wound care system, as opposed to conventional NPWT devices, is that various embodiments of the presently disclosed MWT wound care system can be applied after the first or second (or more) surgical irrigation and debridement procedures (depending on contamination level) and left in place with a single application until the wound is ready for definitive soft tissue management. This time frame is typically greater than the 24-72 hour time limit for changing conventional NPWT system dressings. In order for the wound care system to extend the wear time of a dressing, the various embodiments disclosed herein provide an improved ability to evaluate the underlying wound.

In conventional devices the dressing has little or no structural integrity as they consist of piecemeal placed soft sponges or gauze that adheres to the wound and allows for tissue in growth. The dressing therefore has to be removed within 24 to 72 hours to prevent significant in growth. The current MWT design allows for motion between the dressing and the wound surface. This motion can accentuate the micro-abrasion effect of the abrasive ventral layer. This motion is made possible by the structural integrity of the dressing which in some embodiments prevents the dressing from completely conforming to the wound. This dressing can be staple or otherwise be removably, rigidly affixed to the skin margins. The motion created produces a gentle grating of tissue instead of allowing tissue in growth. Motion of the muscles as well as patient movement encourage wound dressing motion. Additionally, the positive pressure bladder module and the wound approximator module will both encourage small amounts of motion along the wound surface which should reduce or prevent tissue in growth. The inherent structural integrity of this dressing allows the dressing to serve as a fixation point in additional to its role as a maintainer of the specified spatial relationships of the functional elements of the system contained in the dressing.

One significant weakness of conventional designs is that the wound filler is black or otherwise opaque material. When these conventional dressings are in place they completely obscure the underlying wound bed. This makes it difficult to diagnose the underlying wound. Further means for evaluating the health of the wound may need to be provided to the physician and/or wound care specialist over the course of the extended wound dressing wear time, to allow for early identification of infectious complication and/or the appropriate time to end MWT and progress to the definitive soft tissue management procedure. In some embodiments of the MWT dressing, a translucent window or windows is incorporated into the dressing, full thickness to afford direct visualization of the wound bed. In general, the netting, mesh or thin perforated film and functional elements of the MWT dressing are made of clear or translucent materials, to afford some visual understanding of the appearance of the wound bed.

In various embodiments the spaces between tubing in the web-like pattern are connected by an impermeable netting or thin perforated film that is translucent or transparent, allowing direct visual assessment of the wound. Some embodiments may have a clear window in the dressing that allows improved visualization of the wound surface. In some implementations the vacuum connection tubing has a port, typically just proximal of the tubing connection point/vacuum interface that allows for aseptic sampling of the wound fluid exudate. Alternatively, sampling can occur at the port used for accessory tubes that connect island bridge dressings, when one EVR is used to programmatically care for several wounds, as depicted in FIG. 5A.

Direct visual assessment of the wound is a potential benefit of this MWT system. It is made possible through several possible means in the system described herein. Transparent construction, allows viewing the wound through clear portions or "windows". Additionally, a camera or tunnels or channels to place a camera or scope through to visualize the wound can be offered in specialized embodiments of the dressing.

Figure 16:
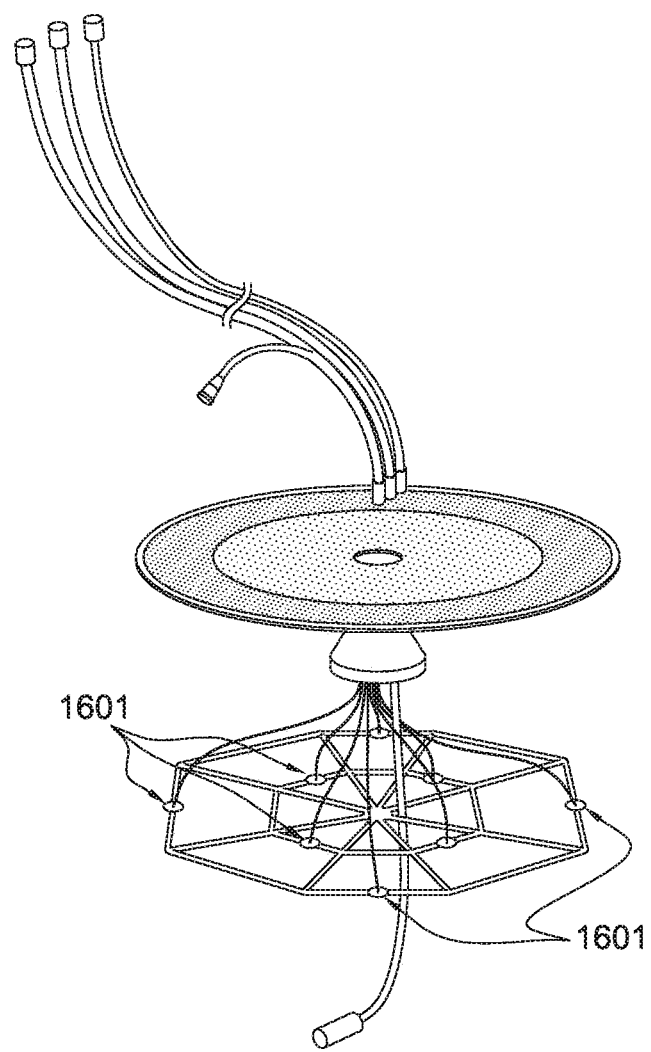
FIG. 16 depicts an embodiment with multiple pressure sensors.

FIG. 16 depicts an embodiment with multiple pressure sensors. Such examples of available monitors are the Tekscan thin film contact pressure sensors and various versions of flat ambient pressure sensors. As the suction is applied, the dressing is compressed to the wound. If a leak occurs, the suction and therefore the contact pressure are reduced in that area. A decrease in pressure in certain areas can be sensed by the flat contact sensors. The location of the sensor can be identified by the EVR due to the spatial relationship maintained by the unified dressing design. The sensors can be numbered, color coded or otherwise marked to allow identification of the area where less pressure is occurring therefore identifying the leak or the location of the leak on the dressing. Similarly, sensors of ambient pressure can be used to directly measure the magnitude of negative pressure at or near the wound surface in multiple locations. Regional differences in ambient negative pressure within the sealed dressing and at the level of the EVR can be detected to identify leaks and their location. The use of multiple wound (at or near the surface) pressure sensors 1601 aids in detecting directionality of an air leak and/or dead spots, which are places where vacuum and/or irrigation is not reaching a segment of the wound surface. Multiple wound pressure sensors 1601 facilitates adjustment of the device for maximum effectiveness, rather than carrying on with one or more undetected leaks. Leakage is the most common system failure in conventional NPWT embodiments, detecting leaks is a key advantage for any system using NPWT. Providing directionality of the leak is a substantial advantage over conventional art, as it directs the provider to the area of the leak, so that additional adhesive sealing sheets can be added to eliminate the leak. A display screen may be configured to show an alarm condition in response to one or more of the sensors 1601 detecting reduced pressure gradient(s). The sensors 1601 can be numbered or color coded for ease of identification within the dressing thereby identifying where the leak has occurred.

Various embodiments include an alarm in communication with the sensors 1601. The alarm may be built into the functionality of programmable electronic vacuum regulator (EVR) 107 of FIG. 1A, or may be a stand-alone unit. In some courses of treatment it is important that the vacuum source be maintained in communication with the wound so as to continually drain fluid off the wound and into a canister. Various embodiments provide an alarm signal that indicates a situation where material is blocking fluidic communication between the wound surface and the collection canister. The term "fluidic communication" in this context means that there is a pathway that liquid and gas can traverse. For example, fluidic communication exists from the wound surface to the collection canister if there is a pathway through which fluids can travel from a wound through a dressing into a tube and to the vacuum collection canister. A blockage eliminates the fluidic communication, at least temporarily, preventing fluids and gas from passing through the device. In some embodiments in which there is a dual (vacuum and irrigation) tubing system, the first response to a blockage alarm is to switch the vacuum source from the vacuum tubing system over to the irrigation tubing system. In some embodiments this may be done by unplugging the tubes (e.g., at their connectors or other joints in the tubes) and switching them around, while other embodiments feature a valve for this purpose. In this way, the irrigation lines serve as a backup to the vacuum lines, in the event of vacuum line blockage or another failure condition. Switching between the lines can be performed either automatically in response to sensing a condition, or manually in response to an alarm or other indication of blockage. The switching between vacuum and irrigant networks can also be performed automatically with a manual override. Clamps or valves in certain embodiments may be used to prevent the possibility of back-flow in the situation where the irrigation line is used as a back-up vacuum line. Additionally, ports within the dressing and/or tubing can be placed that allow for the lines to be flushed similar to intravenous tubing used in the hospital setting, for example, as per accessory port 123 of FIG. 1C. The line can be crimped on one side and flushed with a high pressure aliquot of fluid to force any material blocking the line away from the wound along the vacuum flowpath in the connection tubing to clear the blockage. Additionally, a thin firm rod can be inserted through the port to mechanically clear blockages similar to a stylet in a spinal needle.

Various embodiments include a sensor, often termed a flow meter, configured to record the volume and rate of fluids suctioned from the dressing system to the collection canister as a useful improvement. The flow meter may be built into the functionality of programmable electronic vacuum regulator (EVR) 107 of FIG. 1A, or may be a stand-alone unit. The flow meter provides the ability to automatically record one of the most important metrics related to devices used to drain areas of the body, namely, volume suctioned in a period of time. Likewise, a flow meter allows for the system to be set to alarm in the event the device exceeds a predefined flow threshold. This threshold can be algorithmically (pre-programmed response) adjusted by the EVR to account for fluid that is irrigated, in a MWT dressing that is applying irrigation. The flow alarm process may trigger cessation of vacuum, to immediately stop the facilitated exsanguination that occurs in the setting of an actively running NPWT device during a major bleeding event. When irrigant is to be used, the predetermined amount of irrigant is programmed into the monitoring system so a flow alarm does not sound, as the irrigant is collected at a flow rate, which may be substantially higher than predicted for normal suctioning of exudate from the wound surface. For example, if one liter of irrigant is to be used to irrigate the wound, a 1 liter button (or means to enter the data through a keyboard or similar) can be selected on the EVR. Alternatively, the duration of irrigation can be set (e.g., 30 minutes). Therefore, the specified volume or duration of irrigation is not misinterpreted as a sentinel bleeding event triggering a flow alarm. This ability to monitor and receive both input and produce programmable outputs is one of the elements of the "smart dressing" concept made possible through the MWT system described herein.

Various embodiments are configured with the capability for other types of monitoring. For example, some embodiments are configured to incorporate one or more of a Near-Infrared Spectroscopy (NIRS) sensor, a pH sensor, and/or temperature probe into tubular dressing system. Such embodiments are configured to receive the monitor, camera, sensor or other probe to monitor the health of the wound surface. The data or images from these probes can be recorded/displayed on the EVR or the primary monitor or communicated via a wired connection or wirelessly to the EVR or primary monitor.

In certain embodiments, a camera is incorporated in the dressing or a port is placed in the dressing to allow a camera to image the wound surface directly. This camera can transfer information to the EVR for storage by wire or wirelessly. This provides further means for monitoring the wound. These monitors communicate data to the EVR by wired connections or wireless links (e.g., Bluetooth or Radio Frequency IDentification (RFID)).

Various embodiments are configured to include an advanced electronic vacuum regulator (EVR), for example, the EVR 107 of FIG. 1A. This device measures flow, output and pressure at the canister and receives, interprets and responds to these monitors as well as monitors positioned in or on the MWT dressing. The enhanced monitoring ensures reliable and consistent therapy that can be safely applied for longer periods of time. Since the tubing is a closed system, measuring pressure at the collection canister represents vacuum entered into the system, while pressure sensing proximate to the wound surface measures vacuum reaching the wound. Under ideal circumstances these two measurements should be equal in a closed system. However, in practice blockages of the tubing system or dressing/wound filler, or failures in the system seal (leaks) can lead to differences between the pressure measurement at the canister and the pressure measurement proximate the wound.

Various embodiments may use different configurations of wound pressure sensors positioned in a number of locations. For example, some implementations use one pressure sensor positioned proximate the wound (e.g., wound pressure sensor 119 of FIG. 1C), that is, between the wound dressing and the surface of the wound or separated from the wound surface by a single layer of netting, mesh or thin perforated film. Other embodiments use two or more wound pressure sensors (e.g., pressure sensors 1601 of FIG. 16), also located at or near the wound surface. The one or more pressure sensors are configured to communicate directly by wire, mated with the vacuum/irrigation tubing to the EVR, or can transmit wirelessly to the EVR, using wireless technology, e.g., Bluetooth, RFID, or the like. In one enhanced embodiment four or more sensors are positioned in a grid or at the four compass points of the dressing, to provide insight as to the location and/or direction that a leak probably may be occurring.

The electronic vacuum regulator (EVR) can be configured to either use wall suction or a portable vacuum source. Various configurations are modular to allow for quick connection to either source of vacuum. Various embodiments feature an internal back-up vacuum motor and rechargeable power supply, in order to bridge any temporary outages or to support short trips, away from the primary wall suction vacuum source (e.g., bathroom, operating room, recovery room). Various implementations are small enough to fit into a Pyxis or Omni-Cell logistical maintenance machine. Unlike conventional NPWT systems, various embodiments disclosed herein are configured so one can readily separate the vacuum regulator from the vacuum source, thus providing flexibility to respond to specific, special situations that are not possible when the regulator and vacuum source are married in a single device. Separating vacuum regulation from the vacuum source answers an unmet military (and civilian) need, which is the ability to manage two or more wounds with a negative pressure wound dressing on the same patient at two or more different levels of vacuum (e.g., full dose for an open wound and partial strength for a skin graft site). This can be accomplished by the novel design described herein, which separates the vacuum regulation location from the vacuum generation location. For certain specific indications (for instance military medical transport flights), multi-channel versions of the portable vacuum source can exist, that have multiple or a single vacuum pump, but multiple ports that access the vacuum and that can be individually regulated to treat different wounds on the same or different patients. The effluent can be collected in a single or individualized collection canister(s) inherent to the device. The collection canister can be rigid (e.g., a standard vacuum canister) or collapsible, with or without an odor reducing and/or gelling agent added to the canister.

Turning again to FIG. 5B, this figure depicts a flow diagram that illustrates two general means for regulating vacuum and managing multiple MWT dressings over multiple wounds on a single patient. First, an accessory fixture can be applied to the wall or portable vacuum source. This will serve as a splitter, which takes the single vacuum source, and provides two or more ports for individual standard EVR units, that allow each wound to be regulated at a specific pressure. Conversely, a special EVR, that connects to a single standard wall or portable vacuum port can possess two or more ports with independent digital regulation of each port. The single EVR with multiple vacuum ports embodiment, allows for a port to remain available for routine hospital suction needs, like suctioning an airway. In this way, the multi-port embodiment of the EVR would have at least one port that could serve simply as the vacuum regulator for therapeutic suction. These two options are not mutually exclusive.

The EVR contains a processor that allows for programmable control over the multiple functional elements contained in the MWT system. The EVR contains an internal memory device and has dataports that allow for exporting data from the EVR to a portable storage device or by wire or wirelessly to a computer or electronic medical record system. This dataport can be bi-directional in certain embodiments, allowing elements of the electronic medical record (e.g., vital signs) to be incorporated into internal algorithms that prescribe MWT or set off alarms. For example, acute changes in heart rate and blood pressure along with higher than normal flow rates of effluent from the wound, can trigger a flow alarm and response, which includes immediate cessation of vacuum. Further, specialized programmed algorithms can prescribe specific sequence of events in the MWT which dictate precisely the timing and duration of irrigation, suction, bladder inflation, ultra-sonic agitation or any combination of the MWT modules described herein that are utilized in treating a specific wound. The EVR will have the ability to control when different aspects of the dressing are activated, making this a programmable mechanical wound therapy dressing. The EVR will be manufactured with set algorithms loaded to the system, and it will have the ability for end-users to enter custom programs or customize existing programs of therapy, monitoring and alarming. For example, setting cyclic patterns of irrigation and vacuum to increase wound cleansing in infected wounds. This additional element of the "smart dressing" concept allows for specific wounds to be treated in different methods, tailoring care.

An additional embodiment allows for a fluid gas separation system that is independent of gravity or position of the collection element. This system might include a malleable bag that can contain highly absorbent balls to separate fluid from air but still allow passage of air through the bag, for example, as depicted in FIG. 6A. The size of the bag can vary based on the estimated amount of exudates to be collected from the wound. The bag could be similar in size and shape to a standard IV bag made out of plastic, rubber, latex, or other polymer. It may be of different sizes or amounts of expected fluid collection to aid in intake and out take measurements by clinical care providers. Conventional systems usually require the collection canister to be upright and typically hard. One benefit of such a system described herein is that it tends to eliminate the need for a rigid collection canister that uses gravity and a stationary post to hold the canister upright. This system would allow for more mobility and transfer well to the out-patient setting. The bag or system can be worn on a belt with a portable vacuum source. Filters can be incorporated into the system to prevent biological matter from proceeding past the collection bag and into the EVR or vacuum source. These collection bags are generally disposable. A moisture sensor or humidity monitor can be incorporated to indicate when the bag should be changed. An alternate monitoring system monitors the resistance to flow through the specialized collection bag. As the hydrophilic material becomes saturated it might expand and reduce the flow or increase the resistance to flow which can be monitored and used to determine saturation of the hydrophilic material. Once a threshold of moisture was surpassed, an indicator in this embodiment sounds to signify that the bag needed to be changed. Additionally, a weight sensor may be used to determine when the collection bag was saturated with fluid. The cut off weight would be determined by the amount of fluid expected to saturate the collection bag. As fluids—that is, exudates which would mostly be water—are collected the weight of the bag increases. The saturation weight may vary based on the expected volume of water collected for the size of the collection bag. Something as simple as a moisture sensor patch may be incorporated on the side of the collection system that turns colors as the moisture meets some predefined threshold. One example of such moisture cards are AGM (Tucson, AZ) moisture cards that change from blue (dry) to pink (wet). Other like types of moisture cards may be used as well. The bag is typically configure with an inflow port and an outflow port on the opposite side. A quick-connect, featured in some embodiments, allows the bag to be easily changed when full.

One embodiment allows the fluid air mixture to flow between balls of a fixed similar to air traveling between marbles. In some implementations of this embodiment variable sized balls are used. The balls can stand alone or with cage like coverings that maintain a constant shape. The hydrophilic balls expose the fluid/air mix to a highly absorbent material across a significant surface area. The cages would give structure to the absorbent material to prevent complete collapse and blockage of the flow of air. As the mixture of air and fluid passes across more balls, the gas tends to become more dry. A series of bags can be used if needed to ensure complete capture of fluid.

An alternate design features a specific column or tubular structure with a series of circular channels to allow air/fluid mixture to pass, filtering out the fluid phase as it passes down the separation column, for example, as depicted in FIG. 6B. In at least some embodiments the walls of the channels create a cage-like structure for holding super absorbent material that tends to dry the air as it passes down the tunnel or channel. A one-way anti-microbial/anti-viral filter can be placed at the egress end of these collapsible versions of the collection device to cleanse/decontaminate the outgoing air. One example of this type of filter the HEPA (High Efficiency Particle Arrestor/air filter) manufactured for biological use. The filter of this embodiment may be positioned in various locations in the MWT system, but is typically located at or near the air output exit duct of the EVR, that is, the point where the air from suction gets expelled to the outside environment.

Air and water are fluids, and as such, they tend to follow the path of least resistance. The present inventors recognized a flaw of conventional system involving the fluid path of the irrigant. When a path for irrigation instilled onto the dorsal surface (the side of the wound filler that is opposite the wound bed) of a conventional NPWT dressing is allowed unrestricted communication to an outflow system that is kept under negative pressure, the fluid will pass from high to low pressure and circulate on the side of the dressing opposite the wound, rather than following a path of greater resistance through wound filling material to the actual wound surface. This flaw of conventional systems is overcome by several elements of the various embodiments disclosed herein. For example, some embodiments feature a spatial orientation of the dressing in which the irrigation component is placed in closest proximity to the wound, separated from the vacuum source, such that the flow path of irrigant tends to be directly across the wound surface rather than through or over the top of the wound filler. The manner of operation of these embodiments is superior to the conventional systems that attempt to circumvent the design flaw by ceasing vacuum suction during the application time of the in-flow irrigating fluid. In systems that have a wound filler, this simply means saturating the filler until the fluid leaks to the wound surface. In systems both with or without a filler this can lead to pooling of fluid under the dressing seal. The present inventors recognized the advantage of implementing irrigation as an active process featuring both the application and simultaneous removal of the irrigant. In this way, the irrigation system of the various embodiments tends to be maximally effective. This innovation allows for the irrigation component in this MWT device to act in a lavage mode, which serves to better wash/cleanse the open wound, which is an important element of open wound care that currently is not offered by conventional systems. Due to this weakness in the current art, repetitive surgical operations or procedures are instead required to attain a similar effect.

Additionally, an alternate embodiment would allow for controlled delivery of alternating irrigants, for example, as depicted in FIG. 3B. This embodiment can alternate between a fluid irrigant and a gaseous irrigant or between different types of fluid irrigants, like an antiseptic agent, immediately followed by normal saline or water, to negate/reduce the cytotoxic effects of some potent antiseptics. By alternating the irrigants, the lavage would allow for increased agitation and mechanical debridement as well. A fine filter can be used to prevent contamination of the wound when using nonsterilized gas (e.g., air). A back flow valve may also be utilized to prevent retrograde flow of the irrigant from the sealed dressing, back into the irrigation conduit tubing.

Pooled fluids tend to weaken the seal of the wound dressing, often leading to increased dressing failures. Pooled fluid will leak toward the occlusive dressing and its seal with the intact skin margin. This adhesive interface has and will continue to be a weak point in NPWT dressing function. Most adhesives tend to lose their adhesive quality as they become wet. In conventional systems the seal between the occlusive portion of the dressing and the skin is the most common site of correctable failure for NPWT dressing (e.g., "leak"). A conventional irrigation system, which requires the vacuum to be stopped during the in-flow period, because the system's construction requires sharing tubing or passageway/flow-paths between in-flow (e.g., irrigation) and out-flow (e.g., vacuum), puts additional stress on the adhesive seal. Thus, conventional NPWT systems, while they may solely function in the application of a vacuum to a wound surface, with certain and clinically real limitations, cannot function as the outflow side of an integrated MWT device. Various embodiments disclose a means for providing regulated negative pressure to a wound, which can be regulated to apply simultaneous continuous or intermittent vacuum during periods of irrigation. The EVR can regulate irrigation and vacuum elements. The EVR can control the pattern of intervals of simultaneous or sequential functioning of these two elements. Algorithms for irrigation and vacuum application can be programmed on the EVR at fabrication, with the ability of the end-user to customize algorithms and store the custom algorithm as well on the EVR. Additionally, a means of accounting for specific volumes of irrigation passed through the MWT system can be incorporated. For example, the EVR is programmable to increase the threshold for flow alarms during periods of irrigation to prevent false alarms for elevated flow rates. As previously described, this ability will prevent false alarms by preventing alarms from sounding for increased volume collection being interpreted as increased blood loss. For example a 1 liter button can be pushed to allow the EVR to expect a liter of irrigation to be collected over the next predetermined time frame preventing an alarm from sounding when the system detects increase flow by suction. Further, this will allow the EVR determination of output/wound drainage to be automatically corrected for the irrigation fluid volume. In other embodiments, the system can record the flow rate and volume of irrigant infused in real-time, which is then reported to the EVR, to again allow the EVR to exclude externally applied volumes of fluid in its computation of flow rate, as it pertains to the flow alarm and response to vacuum-assisted exsanguination response algorithm.

One aspect of the various MWT embodiments is the ability to implement integrated, simultaneous vacuum and irrigation. This allows periodic lavage of the wound surface, which in turn, helps to mitigate bacterial load/biofilm and reduce exudate/fibrin build-up. Layered, unidirectional wound filler filled and/or single layered versions of the MWT dressing may include tubes which convey fluids away from the wound under regulated vacuum control, and a second set of separate closed tubing system that conveys fluid irrigant to the wound. The irrigant can be varied to adapt to the situation and the course of treatment. For example, the fluid irrigant may be potable water, saline, antibiotic, antiseptic or filtered gas (e.g., oxygen) or alternated between different irrigant options.

In some embodiments, the fluid in-flow and out-flow tubing meet at the wound surface. In other embodiments, the in-flow tubing is maximally distanced from the out-flow egress. For most embodiments, the path from in-flow to out-flow occurs across the wound surface, which is the location where this fluidic communication should occur, for situations in which the goal is to provide wound irrigation. The design of the various embodiments ensure irrigation and effluent flow paths communicate to all parts of the wound. This allows for continuous and intermittent irrigation modes, which can be pre-programmed or left for customization by the end-user. In various embodiments the two separate tubing systems do not come to a central common point, but rather, maintain separate ingress and egress for each system, such that the only common location between the two is the wound surface. In various embodiments, the tubing systems typically communicate through a chamber or flange to a dual-lumen tubing system (one suction, one irrigation). In such embodiments the tubing communicates on one side retrograde to the collection canister and then the vacuum source and on the other side antegrade from an irrigant source. In this way the fluid can be controlled to flow passively or actively into the wound where it is evacuated by simultaneously or sequentially applied vacuum through the egress tubing system.

An exemplary embodiment of this dressing has a central vacuum wound interface chamber, for example, as depicted in FIG. 1R, or flange(s), for example, as depicted in FIG. 1S adjacent to a central tubing connection point with or without accessory vacuum tubing distal to this point. A completely separate tubing system bypasses this vacuum interface to extend to the deepest layer (e.g., layer closest to the wound surface) where it fluidically connects to the radial or spider-web oriented irrigation tubing system, that centripetally extend from a central point to the periphery, allowing for maximal customizability, which would not be possible in a dressing that has independent peripheral members. Tubes of set inner diameters, that typically are chosen to equal the diameter of fluid passage holes in the tubes that face in three directions (both horizontal planes (e.g., left and right) and then deep (e.g., towards the wound surface) to deliver irrigant to the wound surface. In this exemplary embodiment, the two tubing systems remain separated by being situated between different layers of the layered dressing and have completely dedicated tubing/conduit systems from source to wound bed, allowing for activation of either system simultaneously or at set intervals to each other, to most effectively irrigate and remove the irrigant from the wound surface. The deepest (wound facing) layer can be abrasive to provide a micro-abrasion/debridement effect when the dressing is agitated by the positive pressure bladder described herein or simply through contraction of the underlying muscle.

Additionally, the dressing affords some structural integrity to allow the dressing to be secured to the skin edge prior to obtaining a dorsal seal with either staples or sutures. By securing the position of the dressing, this process allows for small motion for micro-debridement effect, but not too much to allow seal disruption. This process can only be performed if the dressing has some structural integrity to allow it to be fixed to the wound edge. Further this quality of the MWT dressing platform can resist the normal tendency for skin margins of large open wounds to initially spread, especially in the setting of traumatic swelling. The structural integrity is provided by the netting, mesh or thin perforated film layered construction.

At least some embodiments feature a pulse lavage function where the irrigation tubing line is charged (e.g., loaded from source to wound with irrigant) and then active pulse pressure is applied, with simultaneous negative pressure from the vacuum side. This allows pulsed pressure lavage irrigation, which is not described nor enabled by the current art. Forcing fluid directly across the wound surface under pressure (typically low pressure), more effectively cleanses the wound, as it works to cleanse the wound through a mechanical effect and through the solubilizing effect of having a fluid in contact with the wound surface. Current art at most allows for the solubilizing effect though irrigant instillation, but does not allow for the mechanical effect, which is as effective or more effective at cleansing the wound surface. This same mechanical cleansing effect can be produced by the reverse pulse lavage mode of irrigation described herein. In other embodiments, passive irrigation is created by simple gravity in-flow. Typically, the vacuum source is separated from the dressing/irrigation tube system by a valve or other control feature that regulates the degree to which the irrigation system is affected by the vacuum system. In at least some embodiments, this control mechanism is a one-way valve that allows irrigation to flow to the wound surface in the setting of applied negative pressure within the dressing. Distal to this valve is a crimp or similar that closes the irrigation tube, so that the one-way valve in the irrigation tubing only sees vacuum when irrigation therapy is desired. In some embodiments the vacuum side of tubing has a tubing port connection that allows for fluid to be injected to aid in clearing a clog or blockage in the system, followed by immediate resumption of the vacuum. Further, this vacuum side tubing port can be used to sample the effluent. The irrigation side tubing may be configured with additional ports as well for injection of adjuvant agents.

An additional embodiment allows for an alternating valve to allow gas/air and fluid to be alternated, for example, as depicted in FIG. 3B. This valve can alternate between allowing fluid such as IV fluids and gas such as air to be pulled by the suction on the reverse pulse-lavage setting in a set fashion. The air may travel through a filter to prevent microbial contamination. This alternating system would allow the irrigant to be cleared before pulling more fluid across the wound. This system would prevent pooling while still performing its irrigation function.

Edema fluid tends to collect at sites of soft tissue inflammation. This complicates wound healing by multiple mechanisms, like increasing the volume of the wound, retracting skin margins and reducing capillary perfusion. Various embodiments disclosed herein help to mitigate this problem by using an inflatable bladder that applies pressure to the wound. Pressure is applied on the wound using the inflatable bladder that preferentially expands towards the wound surface. This preferential expansion and therefore pressure application is caused to occur by various means, like placing a sleeve over the affected extremity, placing the bladder between the wound approximating device and the sealed MWT dressing, affixing the bladder to the skin margins or through construction, with more pliable ventral material compared to dorsal. The pressure would vary based on clinical desires and use. The range could be controllable based on desired effects (e.g., venous congestion, DVT prevention, edema control, skin closure, wound debridement). Specific pressure values can be set for different uses. A range from 0 to 30 mmHg may be used in a typical situation, although pressures exceeding 30 mmHg may have clinical utility in specific conditions. The bladder can be inflated with gas or liquid, which can be pre-heated or pre-cooled, under control of a temperature control unit, to provide an additional mode of therapy. The temperature control unit may be embodied as a variable switch connected to heating/cooling units in contact with the liquid or gas used to fill the pressure bladder. Cooling could be down to or below 32 degrees Fahrenheit such as using ice water or a solute in water solution that can be cooled external to the bladder. Applying ice to an injured extremity tends to reduce and/or inhibits edema in the acute setting. Heat could be used up to or above 180 degrees Fahrenheit to promote increased blood flow and provide an analgesic effect. Applying intermittent positive pressure to the wound can help "squeeze" the edema fluid which collects at sites of soft tissue inflammation. The net effect of this squeezing used in tandem with the wound approximating system described herein is that wound volume can be reduced and the likelihood of successful delayed primary closure increases. Delayed primary closure is a preferred mode of definitive treatment to wounds treated by NPWT or MWT. It is generally a cheaper, more cosmetically pleasing mode (as opposed to skin grafting), which restores full thickness skin coverage to the wounded site. Pushing on the wound with a bladder, then releasing the bladder and applying a wound approximating force to the wound margins in a sequential fashion over a sufficient period of time will allow closure of the wound in many instances. Pushing on the wound dressing, also serves to reinforce the adhesive layer's seal and the micro-debridement of the wound surface caused by the abrasive ventral layer. Additionally, the positive pressure can pump irrigation fluid in deeper areas of the wound.

The inflation can stretch tissues to prime the tissues for the wound approximation effect of the integrated MWT system. This component represents a dynamic way of getting edema out and preloading the wound approximating module. As the bladder inflates, tension in the approximating system is increased stretching the skin margins to no greater than a preset force limit, then as the bladder deflates, the wound approximating module, pulls in the stretched skin margins, helping to sequentially approximate the wound. This preload, reel-in effect is akin to the actions of catching a large fish on a fishing pole. When fishing, a forced is applied by pulling back against the fish with the rod, the force is released by leaning back towards the fish and reeling in the slack. In a similar fashion, the skin edges are placed in traction by the bladder, once the bladder is deflated, the approximator reduces the slack thereby assisting in the approximation of the wound.

The bladder also acts like a sequential compression device (SCD) to help with venous return and reduce venous congestion/stasis. To this end, the bladder can have multiple chambers that are inflated/deflated sequentially. The pressure and rate of inflation is controlled by the EVR under preset algorithms or those custom entered by the end user. However, there are specific clinical situations where the bladder may not be recommended or applied. The EVR can be pre-programmed or end-user programmed, to maximally shift from one therapeutic to the next, to include the inflation/deflation cycles of the bladder relative to episodes of therapeutic irrigation, again supporting the "smart dressing" concept.

Debridement is one of the features in wound care addressed in various embodiments of the MWT system. The inflatable bladder is one of the components of the MWT system that accomplishes this task. The inflate/deflate cycling of the bladder will provide some motion of the abrasive wound-facing surface of the dressing, which can stimulate micro-abrasion or "micro-debridement," which loosens/clears fibrin slough, exudate build-up and biofilm. The motion provided by the bladder for the dressing on the wound will include up down (compression) as well as side to side motion. This motion will also limit tissue in growth which allows the dressing to be maintained for longer periods of time.

The bladder can also be inflated and held inflated in a continuous fashion for certain situations, specifically over skin grafts, where conventionally bolsters or NPWT have been used to ensure the graft remains well approximated to the recipient bed. In this application and some others, the bladder will be held in place by a sleeve (e.g., circumferential or with an opening and fastener) that can be placed around the affected site akin to a SCD stocking, for example, as depicted in FIG. 7A. In other embodiments, the bladder can have a skirt that can accept staples or other means for removably affixing the bladder directly to the skin margins. Alternatively, in wounds treated with the wound approximating device module, the bladder can be held in place by the support ribbons/tapes of the overlying wound approximating device. This device can act as a wound approximating device as well as a backboard to direct the force of the bladder towards the wound. If there is no sleeve, backboard or other means of directing the force applied by the inflated bladder (e.g. fixing the bladder to the skin margins), the bladder will inflate and expand away from the wound and not direct force towards the wound. The torque limiter of the wound approximating device prevents unsafe pressures from being applied to the skin at the margins of the wound while directing a safe amount of downward force towards the wound. The positive pressure bladder can have a secondary effect of expediting the approximation of the skin edges to allow for more rapid and/or complete primary closure. Additionally, cold fluid such as ice water can be used to inflate the bladder which would create additional means of reducing edema. This can be alternated to warm fluid in a sub-acute setting to promote blood flow and healing. In this way, the positive pressure bladder is yet another functional element of this system that supports the novel concept of mechanical wound therapy.

In most embodiments, the bladder will be unidirectional through construction, having a more pliable surface facing the wound and a more rigid surface facing away, for example, as depicted in FIG. 7B. The more pliable surface will direct positive pressure towards the wound, directing the pressure into the undulating, uneven surfaces and/or shallow crevices of the wound.

For an additional therapeutic effect, the bladder, in some embodiments, can be inflated with warmed or cooled fluid to provide warmth or cooling to the wound bed and underlying injured tissue. This temperature therapy can further reduce edema, swelling and/or pain. This can be alternated to warm fluid or between warm and cool fluid in a sub-acute setting to promote blood flow and healing. Inflation of the bladder with the temperature controlled fluids can be held for periods of time or frequently cycled as specified by the end-user through a control function integrated in the electronic vacuum regulator.

Additionally, a more pliable undersurface would allow the uneven wound to be fully treated. As the bladder expands, it will fill the deeper undulations and allow an even force to be applied to the whole wound. A less pliable bladder would create pressure points where some areas receive the force while others do not.

An additional embodiment for the positive pressure bladder may incorporate a ultrasound device or electromagnetic device within either the bladder or dressing itself. The use of these type devices would be two fold. If the injury included a bone injury, these two modalities have been shown to have beneficial effects on bone healing. Additionally, ultrasound placed within a fluid filled bladder can produce vibrational agitation that can improve wound cleansing.

Skin and fascia both have an elastic property that passively retracts wound edges left open over time. This process can be increased by swelling of the muscle and subcutaneous tissue. Left to its own, the only competing force to the centripetally outward egress of skin margins in open wounds is the cellular fibroblastic response in granulation tissue, which over a long period of time produces some uncontrolled contraction of the wound. Generally, this does not result in primary apposition of skin surfaces, but rather dense central fibrosis that eventually epithelializes. Various embodiments of the MWT wound care system account for this process. The various embodiments are capable of securely coupling the skin margins to the dressing. Some conventional systems rely on non-integrated tensioning devices that are separate and act independent of the NPWT dressing. Likewise, some conventional tensioning devices exist which are not integral to the NPWT device. In both situations, the lack of integration, compromises the individual functions, for instance, some conventional tensioning devices need to be applied beneath the sealing adhesive layer of the NPWT, which increases the risk of leak.

Various embodiments disclosed herein feature an integrated wound approximating device designed to provide dermatotraction (approximation of the skin margins) without compromising the function of the underlying NPWT dressing. This aids in halting and reversing expansion of the wound dimensions. Further, the integrated wound approximating device of the various embodiments allows a controlled and directed amount of approximating force to be applied to the skin margins to sequentially close down the wound.

Another embodiment of the integrated wound approximating device features an integrated modular component that is placed over the sealed basic MWT dressing. In various embodiments it is considered modular since, in those embodiments, it may be implemented as an independent device. It is secured to the skin margins with staples, sutures or other means of temporary fixation over a previously applied and sealed MWT dressing. In the most typical form, the modular component has a central crankshaft around which are wound ribbons or tapes that are affixed centrally to the crankshaft and distally to two pull-tabs. Centrally there can be a ring that slides over the central tubing connection point of the basic MWT dressing. This acts to anchor, but not necessarily through rigid connection, the wound approximating device module to the basic MWT dressing of this integrated system and to keep the crankshaft oriented in the long axis of the wound. The pull-tabs are then pulled away from each other, from the rolled position, out to a length sufficient for them to overlie normal skin. This action is akin to unrolling a shade on a window to a desired length. The pull-tabs have an adhesive back that provide temporary fixation to the skin or adhesive film of the basic MWT dressing. Then staples, sutures or other means of fixation can be placed through the pull-tab or ribbons/tape to firmly affix the approximating device to the skin. In a common embodiment, a rubberized central core will exist in the pull tab, that has enough integrity to not allow the staple to pull through, but soft enough to be stapled through to affix the pull tab to the skin. This rubberized material will provided a self-sealing effect about the staples, as well. A sufficient number of ribbons/tapes per unit length are used to reduce number of staples needed, but also spread the stress on the skin over a sufficient number of fixation points (e.g., 1 rib/tape every 2 cm). If desired, a skin glue, stoma paste, or similar product can be placed over the staples to ensure that their perforation through the pull tab and the underlying adhesive sheet of the basic MWT dressing, does not disrupt the seal, for example, as depicted in FIG. 6A.

Turning again to FIG. 9B, a removable crank 980 may be attached to the end of the central crankshaft so that it can be turned manually. The crank 980 may be embodied as a ratchet type mechanism. The central crankshaft—for example, the crankshaft 970 of FIGS. 9A-9B—may be configured with a torque limiting feature that prevents generating a pulling force above a threshold that is potentially harmful to the patient. The crankshaft is the central origin for the ribbons in the wound approximating device, around which the ribbons are wound as the crankshaft rotates. The manual crank 980 can be attached directly to the terminal pole of the crankshaft 970 or through an appendage, that extends some distance (e.g. 2 to 10 cm) between the cranking element and the central crankshaft to allow access to the crank without having to remove the dressing or splints that may be present on the injured site. Different amounts of approximating force would be useful in different situations. Therefore, multiple torque limiters can be used in series that will allow for different maximal tensions to be created at different times during therapy. In some embodiments, a series of torque limiting springs or devices are incorporated, each with its own maximal approximating force threshold. Alternatively, a single torque limiter that is adjustable over a range may be used. The provider or end-user can select the maximal force setting (e.g. high or low) that is most appropriate for the wound. Typically, this will require moving a switch that engages the selected spring or torque limiting device. This specific embodiment of the torque limiting feature of the wound approximating device may be particularly well suited for some wounds for which maximal approximating force should be kept low initially (e.g. fasciotomy wounds), however with time and tissue relaxation, the safe threshold for approximating force can increase. In addition, there is a stop catch, that can be released, that holds each increment of force added through rotation of the crank, but can be released, to release the force if desired. Alternatively, the crank can be spring operated to apply a specific amount of continuous force to the skin margins. A pin or other like type of mechanism can be activated that temporarily or permanently halts and/or reverses the continuous force application, as desired. Lastly, in the setting of an open abdominal wound, a specific embodiment of the wound approximating device is connected to the fascia (rather than the skin), to approximate the fascia, thus allowing for primary closure of the fascia or to minimize the area of fascial graft/defect that is left, when the overlying cutaneous layer is finally closed/covered.

In some embodiments, a central spring with torque limitation that is activated when a set magnitude of force or duration of force is exceeded, can provide time-sensitive, graded force control. For example, the torque limiter, which releases or reduces force, can be activated when an unsafe injurious magnitude of force is obtained at any instance, or when a sub-injurious, but non-beneficial force is maintained for an unacceptable period of time. We therefore describe force limiters that respond to a threshold absolute magnitude of force or a specific duration of a sub-maximal threshold force that is maintained for a set period of time, both of which result in automatic relaxation of force. An exemplary embodiment would include, the maximum force the device can apply is set as a high force value. Any load over the higher limit would automatically be released back down to the preset value. In addition, the torque limiter can be set to respond in the event a force less than the higher limit is applied for a predefined period of time, resulting in a release of force to a lower force that is a safer value that can be tolerated for sustained periods of time. This feature would allow for the bladder to apply a higher but transient force up to a higher limit for short periods of time (seconds to minutes). If force exceeds the limit for more than a predetermined time frame the force limiter activates to release unsafe sustained higher force that could cause ischemic or injury to the tissue. The ability to tolerate transient higher, but still non-injurious, force applications would allow for more force to be placed on the skin edges at certain times to close the wound or stretch the skin for primary closure. As the skin has the elastic potential to expand a wound, so too does it have the ability to stretch to enable it to cover the wound. Pregnancy demonstrates the amazing potential of the skin and subcutaneous tissue to stretch in response to sustained pressure.

Some embodiments of the integrated wound approximating device module of the MWT system employ nonabsorbable sutures with needles on the peripheral end of the dressing or with loops at the peripheral ends that can be stapled to the skin edges to firmly grasp the skin margins of the wound. These supports would converge on a central portion of the wound. In this fashion the wound approximating device can be incorporated into the basic dressing proper, but typically is a separate module, that is applied as needed over the basic dressing.

Other embodiments employ tabs at the end of ribbons of material that roll around a central shaft. These tabs can have adhesive on one surface to assist in fixation of the tabs to the wound margins. In addition, staples can be applied through the tabs or rib material to further affix the wound approximator to the wound margins. The tabs can have a central gel or softened plastic material that seals the staples to the tabs as they penetrate this material, the sealing adhesive sheet and the underlying skin margin, to prevent or greatly limit the risk of leak at this fixation site. The adhesive underlying the tabs, further aids against the creation of leaks in the system, when the wound approximating module is added to the MWT dressing. The attachment of the ribbons/ribs and the pull tab can be permanent such as glue or other means or it can allow for detachment and reattachment such as Velcro®, snaps, ties . . . . The removable fixation methods at the ribbon tab interface, specifically Velcro® or snaps, or hook and loop or other means can afford another layer of safety against exceeding safe thresholds of approximation force, as the Velcro® or snaps are selected for their release properties at specific forces, such that they release at undesired levels of pulling force in a breakaway fashion. By enabling for selective or total detachment or breakaway, the central spine can be removed to allow inspection under the wound approximating device without removing the staples attaching the tab to the skin, as depicted in FIG. 9A. This breakaway feature is both protective as well as practical which is unique to the current design that is not present in the current art. The ability to remove and replace the approximating device without removing any of the invasive aspects (staples) will allow inspection of the wound as well as the seal without needing to reapply the fixation which is typically painful (staples). Also as the corners are pulled together in an elliptical wound, the outer ribs can be released to allow for continued force in the central or wider aspects of the wound, for example, as depicted in FIG. 9B. This design is also unique to the current design. This allows for selective approximation in certain areas of the wound. Conventional art requires all aspects to be tensioned similarly and does not allow for modifications as wounds close. One area of the wound cannot be selectively tensioned without removing and reapplying the entire device. For these reasons, the ability to release the ribs from the pull-tabs, represents a novel, useful improvement over current art that speaks to the approximation of wounds. This feature is integral to adding versatility to the approximating device.

An approximating dial or shaft featured in certain embodiments is configured to contain a standard approximating force. At a prescribed rate and/or magnitude force can be applied to these supports which would centripetally in circular wounds and transversely in elliptical wounds (like a fasciotomy wound), act to pull the skin margins in towards the center point or long axis of the wound. In some embodiments as the margins are brought centrally, the tubular portions of the basic MWT dressing in a specific pattern will fold on themselves in a predetermined fashion (similar to a folding bed or collapsible chair). The limited volume on the wound surface occupied by the collapsing dressing acts akin to a tissue expander as the supports are sequentially closed over, creating a small dead space in the wound and laxity in the approximated wound margins, to support a tensionless or limited tension delayed primary closure. At the same time, the mesh, netting or thin perforated film construction of each layer, provides ample dead space in the dressing to allow the dressing to collapse to a large degree upon itself, so as to not impeded the wound approximation effect of the intergraded MWT system. Thereby, creating the greatest chance a tensionless delayed primary closure may be undertaken for definitive soft tissue management at the cessation of MWT. In wounds with tenuous edges (e.g., post-radiation areas) or with large segmental skin defects, the controlled and metered force can at a minimum reduce in size the area required for skin grafting or to be left to heal by secondary intent when the MWT is discontinued. In certain embodiments, the magnitude and/or rate of force can be set or adjusted by the end-user, for instance reduced in the setting of tenuous skin margins or pediatric or elderly patients. Ranges of tension could be adjusted using an adjustable torque limiter that would allow for different amounts of approximating force to be applied based on the clinical situation.

Additional embodiments may utilize a flexible center shaft to allow for better fit along the wound surface. Additional embodiments may allow for multiple smaller wound closure devices versus a single device. Also, the size of the wound closure device may be varied or expanded or shortened. Also multiple sizes can be produced to allow the end-user to choose an appropriate size. An additional embodiment would allow for the device to be made only from ribbons or cords to allow appropriate management of more non-standard wound shapes.

As described above, this device is also an integral part of the whole system, which will provide a backboard for the positive pressure bladder when used in conjunction with the MWT system, as depicted in FIG. 8A. This device allows for safe and directed force from the bladder towards the wound. By using the two combined in a unique and novel system, the ability of each to perform its function is maximized. The bladder provides increased cyclical dermatotraction on the skin edges to promote further approximation of the wound through tissue expansion while also decreasing swelling, one of the primary reason the wound will not close. The positive pressure bladder in conjunction with the dynamic backboard effect of the wound approximating module, allows for a directed force to be applied to the wound, that can provide compression and temperature regulation as well as micro-motion of the abrasive dressing to promote wound debridement. Additionally, the force can reinforce the seal along the wound edge by compressing the dorsal layer.

The various embodiments of MWT features for controlling and/or reducing the microbial load on the wound through the application of adjuvant therapy modules. For example, certain embodiments are configured to provide microbicidal doses of ultraviolet light, typically UVC radiation, to the wound surface in metered doses to eradicate or reduce in number microbes on the wound. UVC rays have therapeutic effects that are currently used to treat superficial infection (e.g. ophthalmic) and have a proven safety record in medical applications. An example is the Biomation Thera-Wand C100 for wound care. The range for light wave for UV light is 100-400 nm. UVC light which has shown the best antimicrobial effects are from 100-280 nm. The UVC light would be produced by a separate generator. At least some embodiments employ fiberoptic elements or other means for transmitting UVC light from the dorsal surface of the dressing to the surface of the wound. Some embodiments are configured to deliver gases, for example; oxygen or ethylene oxide, through the irrigation system across the wound surface again to eradicate and/or reduce in number microbes on the wound. Supplemental oxygen specifically, has demonstrated clinical efficacy in reducing wound complications and infections. Conventional clinical applications require systemic delivery through inhalation of air with high partial pressures of oxygen or expensive hyperbaric oxygen chambers. Direct delivery of high concentrations of oxygen to the wound surface via the irrigation tubing system described herein, ensures that the highest partial pressures of oxygen dissolved into body fluids are achieved at the wound surface where they provide the most benefit, avoiding the issues related with systemically administered supplemental oxygenation.

In addition, ultrasonic vibration can be applied to the wound, or through, the dressing to assist in debridement and loosening the biological films that form at the wound surface. This micro-debridement technique can mechanically cleanse the uneven wound surface in a gentle, non-thermal fashion with limited or no zone of injury. This adjuvant module, augments the micro-abrasion/micro-debridement effect of the abrasive ventral surface of the basic dressing and the mechanical push/pull effect of the modular positive pressure bladder system. Ultrasonic transducers can be incorporated into certain embodiments of the basic MWT dressing, including the layered, single layer and unidirectional embodiments that can be contacted/connected to ultrasonic source to apply the vibration to the dressing and/or wound surface. In some embodiments, the entire ultrasonic vibration generator and transducer can be a single unit with its own power supply integrated into the dressing. This can have an on/off switch or can be wired or wirelessly connected to the EVR to be programmably controlled. The ultrasonic transducers can be incorporated, so that they sit in fluidic communication with the wound surface. Alternatively the ultrasonic agitation can be delivered from a distance external (non-contact). Additionally, an ultrasonic adjuvant module may be incorporated into the positive pressure bladder module where a fluid used to inflate the bladder transmits the ultrasonic vibration through to the wound surface. The effectiveness of the ultrasonic agitation can be augmented with simultaneous irrigation of the wound with specific solutions (e.g., ionic solutions) to improve transmission of the ultrasonic waves.

Adjuvant medical device applications are integrated in a modular design. In addition to wound healing adjuvants, bone-healing adjuvants like ultra-sound and/or pulsed electromagnetic fields can be added as a modular layer, external to the sealed basic MWT dressing. One such example of this technology would be the Exogen (Smith and Nephew®) bone healing system. These can be placed directly over the fracture and facilitate healing in the setting of infection or massive soft tissue loss or other challenging wound healing environments, where definitive closure/coverage may not be possible for a prolonged time.

Figure 17:
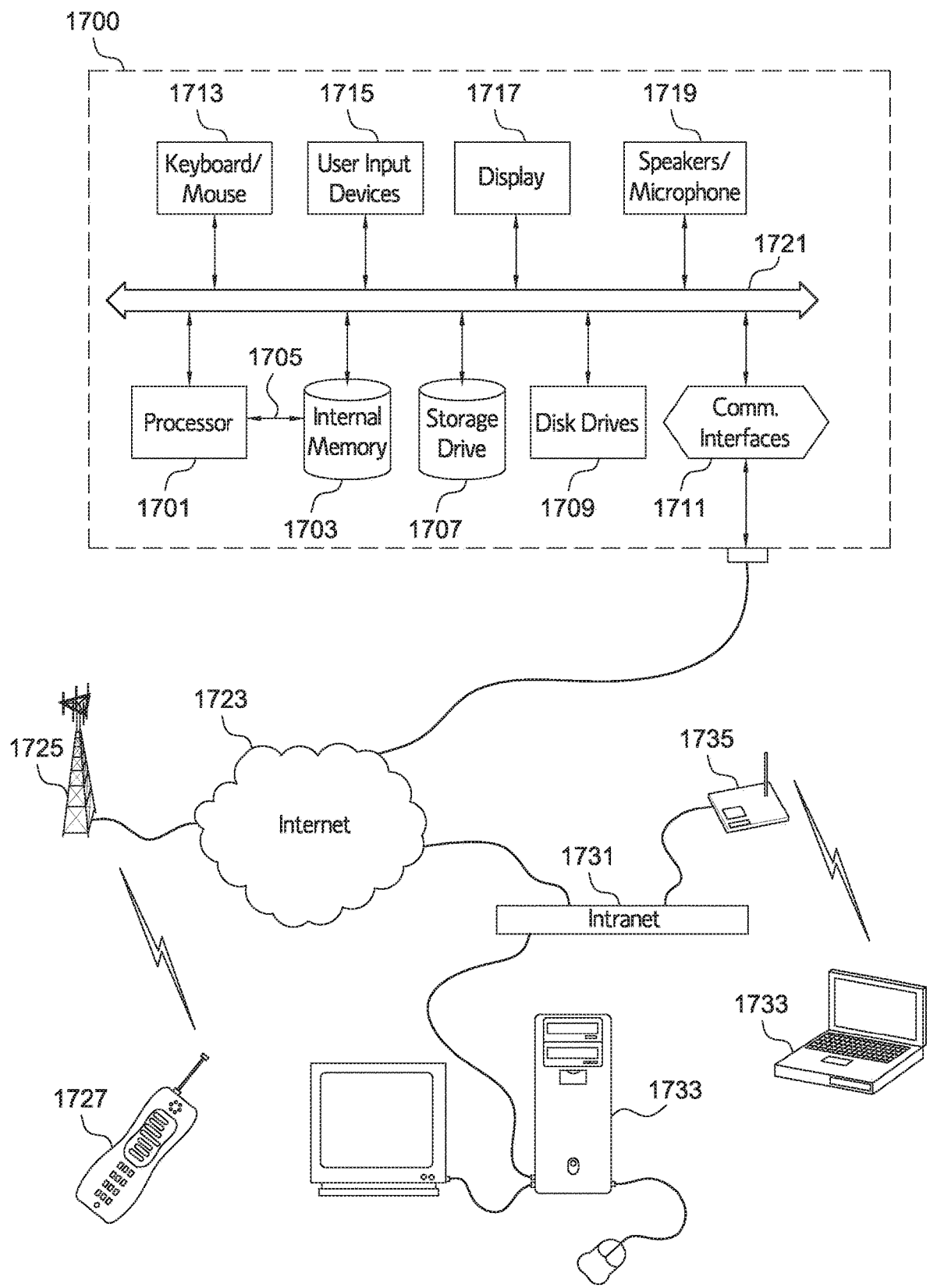
FIG. 17 depicts a computer system suitable for implementing the various embodiments.

FIG. 17 depicts a computer system 1700 and components suitable for implementing the various embodiments disclosed herein. The computer system 1700 may be configured in the form of programmed microprocessor, a laptop computer, a desktop computer, a mainframe computer, or any other hardware or logic arrangement capable of being programmed or configured to carry out instructions. Depending upon the particularities of the embodiment, the computer system 1700 may not include all of the components depicted in FIG. 17 (e.g., computer 1700 may not include a keyboard or mouse 1713, disk drives 1707, and/or other components depicted in the figure). In some embodiments the computer system 1700 may act as a server, accepting inputs from a remote user—e.g., accepting inputs from laptop 1733 or desktop computer 1729—over a wireless node 1735, the Internet 1723, or other communication channel. The computer system 1700 may be located and interconnected in one location, or may be distributed in various locations and interconnected via communication links such as a wireless node 1735, a wide area network (WAN), via the Internet 1723, an intranet 1731, via the public switched telephone network (PSTN), a switching network, a cellular telephone network, a wireless link, or other such communication links. Other devices 1727 may also be suitable for implementing or practicing the embodiments, or a portion of the embodiments. Such devices 1727 may be embodied as a personal digital assistant (PDA), a wireless handset (e.g., a cellular telephone or pager), or other such electronic device preferably capable of accepting inputs for instructions or commands. Those of ordinary skill in the art may recognize that many different architectures may be suitable for the computer system 1700, although only one typical architecture is depicted in FIG. 17.

Computer system 1700 may include a processor 1701 which may be embodied as a microprocessor, two or more parallel processors, a central processing unit (CPU) or other such control logic or circuitry. The processor 1701 may be configured to access a local internal memory 1703, e.g., local cache memory. Some embodiments may integrate the processor 1701, and the internal memory 1703 onto a single integrated circuit and other embodiments may utilize a single level cache memory or no cache memory at all. Other embodiments may integrate multiple processors 1701 onto a single die and/or into a single package.

The internal memory 1703 may include one or more of random access memory (RAM) devices such as synchronous dynamic random access memories (SDRAM), double data rate (DDR) memories, or other volatile random access memories. The internal memory 1703 may also include non-volatile memories such as electrically erasable/programmable read-only memory (EEPROM), NAND flash memory, NOR flash memory, programmable read-only memory (PROM), read-only memory (ROM), battery backed-up RAM, or other non-volatile memories. In some embodiments, the computer system 1700 may also include 3rd level cache memory or a combination of these or other like types of circuitry configured to store information in a retrievable format. In some implementations the internal memory 1703 may be configured as part of the processor 1701, or alternatively, may be configured separate from it but within the same package. The processor 1701 may be able to access internal memory 1703 via a different bus or control lines than is used to access the other components of computer system 1700.

The computer system 1700 may also include, or have access to, one or more storage drives 1707 (e.g., hard drives, optical disk drives, or other types of storage memory). The internal memory 1703 and storage drive 1707 are examples of machine readable (also called computer readable) mediums suitable for storing the final or interim results of the various embodiments. The disk drive 1709 may be embodied as an optical disk drive configured to operate with one or more of various formats that can read and/or write to removable storage media (e.g., CD-R, CD-RW, DVD, DVD-R, DVD-W, DVD-RW, HD-DVD, Blu-Ray, and the like). Other forms or computer readable media that may be included in some embodiments of computer system 1700 include, but are not limited to, floppy disk drives, 9-track tape drives, tape cartridge drives, solid-state drives, cassette tape recorders, paper tape readers, bubble memory devices, magnetic strip readers, punch card readers or any other type or computer useable or machine readable storage medium.

The computer system 1700 may either include the storage drive 1707 and optical disk drives 1709 as an integral part of the computer system 1700 (e.g., within the same cabinet or enclosure and/or using the same power supply), as connected peripherals, or may access the storage drives 1707 and disk drives 1709 over a network, communication channel, or a combination of these. The storage drive 1707 may include a rotating magnetic medium configured for the storage and retrieval of data, computer programs or other information. In some embodiments, the storage drive 1707 may be a solid state drive using semiconductor memories. In other embodiments, some other type of computer useable medium may be used. The storage drive 1707 need not necessarily be contained within the computer system 1700. For example, in some embodiments the storage drive 1707 may be server storage space within a network that is accessible to the computer system 1700 for the storage and retrieval of data, computer programs or other information. In some instances the computer system 1700 may use storage space at a server storage farm, or like type of storage facility, that is accessible by the Internet 1723 or other communications lines. The storage drive 1707 is often used to store the software, instructions and programs executed by the computer system 1700, including for example, all or parts of the computer application program for carrying out activities of the various embodiments.

The communication link 1705 may be used to access the contents of the storage drive 1707 and disk drive 1709. The communication links 1705 may be point-to-point links such as Serial Advanced Technology Attachment (SATA) or a bus type connection such as Parallel Advanced Technology Attachment (PATA) or Small Computer System Interface (SCSI), a daisy chained topology such as IEEE-1394, a link supporting various topologies such as Fibre Channel, or any other computer communication protocol, standard or proprietary, that may be used for communication to computer readable medium. The memory/bus controller may also provide other I/O communication links 1705. In some embodiments, the links 1705 may be a shared bus architecture such as peripheral component interface (PCI), microchannel, industry standard architecture (ISA) bus, extended industry standard architecture (EISA) bus, VERSAmoduleEurocard (VME) bus, or any other shared computer bus. In other embodiments, the links 1705 may be a point-to-point link such as PCI-Express, HyperTransport, or any other point-to-point I/O link. Various I/O devices may be configured as a part of the computer system 1700.

In many embodiments, a communication interface 1711 may be included to allow the computer system 1700 to connect to the Internet 1723 or other network such as that of wireless node 1735. Such networks may operate in accordance with standards for an IEEE 802.3 Ethernet network, an IEEE 802.11 Wi-Fi wireless network, or any other type of computer network including, but not limited to, LANs, WAN, personal area networks (PAN), wired networks, radio frequency networks, powerline networks, and optical networks. A network gateway or router may serve as, or be a component of, an intranet 1731, which may be a separate component from the computer system 1700 or may be included as an integral part of the computer system 1700, may be connected to the wireless node 1735 and/or Internet 1723 to allow the computer system 1700 to communicate with the Internet 1723 over an internet connection such as an asymmetric digital subscriber line (ADSL), data over cable service interface specification (DOCSIS) link, T1 or other internet connection mechanism. In other embodiments, the computer system 1700 may have a direct connection to the Internet 1723. The computer system 1700 may be connected to one or more other computers such as desktop computer 1729 or laptop computer 1733 via the Internet 1723, an intranet 1731, and/or a wireless node 1735. In some embodiments, an expansion slot may be included to allow a user to add additional functionality to the computer system 1700.

The computer system 1700 may include an I/O controller providing access to external communication interfaces such as universal serial bus (USB) connections, serial ports such as RS-232, parallel ports, audio in and audio out connections, the high performance serial bus IEEE-1394 and/or other communication links. These connections may also have separate circuitry in some embodiments, or may be connected through a bridge to another computer communication link provided by the I/O controller. A graphics controller may also be provided to allow applications running on the processor 1701 to display information to a user on a display device 1717. The graphics controller may output video through a video port that may utilize a standard or proprietary format such as an analog video graphic array (VGA) connection, a digital video interface (DVI), a digital high definition multimedia interface (HDMI) connection, or any other video connection. The video connection may connect to display device 1717 to present the video information to the user.

The display 1717 may be any of several types of displays or computer monitors, including a liquid crystal display (LCD), a cathode ray tube (CRT) monitor, on organic light emitting diode (OLED) array, or other type of display suitable for displaying information for the user. The display 1717 may include one or more light emitting diode (LED) indicator lights, or other such display devices. Typically, the computer system 1700 includes one or more user input/output (I/O) devices such as a keyboard or mouse 1713, dedicated or programmable buttons and/or other user input devices 1715 for controlling the computer system 1700. The user input devices 1715 may include, but not be limited to, a touchscreen, touchpad, joystick, trackball, tablet, or other such device. The user I/O devices 1715 may connect to the computer system 1700 using USB interfaces or other connections such as RS-232, PS/2 connector or other interfaces. Various embodiments include input devices configured to accept an input from a user and/or provide an output to a user. For example, some embodiments may include a webcam (e.g., connect via USB), a speakers and/or microphone 1719 (e.g., connected to audio output/input connections). The computer system 1700 typically has a keyboard/mouse 1713 or other user input devices 1715, a monitor 1717, and may be configured to include speakers/microphone 1719, and a webcam. These input/output devices may be used in various combinations, or separately, as means for presenting information to the user and/or receiving information and other inputs from a user to be used in carrying out various programs and calculations. Speech recognition software may be used in conjunction with the microphone to receive and interpret user speech commands.

The computer system 1700 may be suitable for use in identifying critical web services and dynamically relocating them to a new server. For example, the processor 1701 may be embodied as a microprocessor, microcontroller, DSP, RISC processor, two or more parallel processors, or any other type of processing unit that one of ordinary skill would recognize as being capable of performing or controlling the functions, steps, activities and methods described herein. A processing unit in accordance with at least one of the various embodiments can operate computer software programs stored (embodied) on computer-readable medium such those compatible with the storage drives 1707, the disk drive 1709, or any other type of hard disk drive, floppy disk, flash memory, rain, or other computer readable medium as recognized by those of ordinary skill in the art.

As will be appreciated by those of ordinary skill in the art, aspects of the various embodiments may be embodied as systems, methods or computer program products. Accordingly, aspects of the present invention may take the form of one or more entirely hardware embodiments, one or more entirely method embodiments, one or more entirely software embodiments (including firmware, resident software, microcode, or the like) or one or more embodiments combining software, method steps, and/or hardware aspects that may all generally be referred to herein as a "circuit," "module," "logic" or "system". Furthermore, aspects of the various embodiments may take the form of a computer program product embodied in one or more computer readable medium(s) having computer readable program code stored thereon.

Any combination of one or more non-transitory computer readable medium(s) may be utilized. The computer readable medium is typically a computer readable storage medium. A computer readable storage medium may be embodied as, for example, an electronic, magnetic, optical, electromagnetic, infrared, or semiconductor system, apparatus, or device, or other like storage devices known to those of ordinary skill in the art, or any suitable combination of the foregoing. A computer, in this context, may be a general purpose computer (e.g., a laptop or desktop computer, PDA, or like device), a special purpose computer (e.g., a server computer or like device), or other programmable data processing apparatus (e.g., a microprocessor, machine controller, or like device). Examples of computer readable storage medium include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Computer program code for carrying out operations and aspects of the various embodiments may be written in any combination of one or more programming languages, including an object oriented programming language such as Java, Smalltalk, C++, or the like, and conventional procedural programming languages, such as the "C" programming language or similar programming languages. In accordance with various implementations, the program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Various embodiments of this disclosure include the apparatus and systems depicted in the figures and described above as well as method of using and making the apparatus and systems. Aspects of the various embodiments can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, a programmable data processing apparatus, or other such devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and/or block diagrams in the figures help to illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur in an order other than that depicted in the figures. For example, two blocks shown in succession may, in fact, be executed substantially concurrently, or the blocks and activities of the figures may sometimes be executed in reverse order or in a different order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises," "comprising," "includes," and/or "including" used in this specification specify the presence of stated features, integers, steps, operations, elements, and/or components, but do not preclude the presence or addition of one or more other features, integers, steps, operations, elements, components, and/or groups thereof. The term "obtaining", as used herein and in the claims, may mean either retrieving from a computer readable storage medium, receiving from another computer program, receiving from a user, calculating based on other input, or any other means of obtaining a datum or set of data. The term "plurality", as used herein and in the claims, means two or more of a named element. It should not, however, be interpreted to necessarily refer to every instance of the named element in the entire device. Particularly, if there is a reference to "each" element of a "plurality" of elements. There may be additional elements in the entire device that are not be included in the "plurality" and are not, therefore, referred to by "each."

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and gist of the invention. The various embodiments included herein were chosen and described in order to best explain the principles of the invention and the practical application, and to enable others of ordinary skill in the art to understand the invention for various embodiments with various modifications as are suited to the particular use contemplated.

The invention claimed is:

1. A system comprising:
a wound dressing comprising an inlet and an outlet;
vacuum tubing connected to the outlet and configured to apply negative pressure to a wound surface;
irrigant tubing connected to the inlet and configured to provide irrigant to the wound surface; and
an electronic vacuum regulator (EVR) fluidly connected to the outlet via the vacuum tubing, wherein the EVR comprises:
a controller having one or more processors, and
a computer-readable storage medium coupled to the one or more processors having instructions stored thereon which, when executed by the one or more processors, cause the one or more processors to perform operations comprising:
monitoring an irrigant flow within the irrigant tubing,
determining an vacuum configuration for the EVR based on monitoring the irrigant flow within the irrigant tubing, wherein the vacuum configuration specifies a pre-programmed pattern of intervals to apply negative pressure with a force sufficient to (i) cause agitation of a volume of irrigant provided to the wound surface, and (ii) draw a portion of the volume of irrigant to be suctioned into the vacuum tubing, and
driving the EVR according to the vacuum configuration.

2. The system of claim 1, wherein the irrigant is drawn into the wound dressing without use of any positive pressure pump to push the irrigant into the wound dressing.

3. The system of claim 1, and further comprising:
an irrigant source connected to the irrigant tubing; and
a vacuum source connected to the EVR.

4. The system of claim 1, wherein driving the EVR to intermittently apply negative pressure comprises providing programmable bursts of negative pressure.

5. The system of claim 1, and further comprising:
an irrigant source; and
a one way valve positioned along a flow path between the irrigant source and the wound dressing, wherein the one way valve is positioned and configured to allow irrigant to flow out of the irrigant source in response to negative pressure applied by the EVR at the wound dressing and to restrict irrigant flow out of the irrigant source when negative pressure is not applied by the EVR.

6. The system of claim 1, and further comprising:
a bladder having a bladder inlet, wherein the bladder is positioned with respect to the wound dressing to push the dressing into a wound of a patient when the bladder is inflated;
a pump fluidically connected to the bladder inlet of the bladder by bladder tubing.

7. The system of claim 1, wherein the wound dressing comprises a series of irrigant tubes configured to deliver irrigant from the inlet to the wound surface.

8. The system of claim 1, and further comprising:
a vacuum source connected to the EVR; and
a one way valve positioned along a flow path between the EVR and the wound dressing, wherein the one way valve is positioned and configured to allow flow from the wound dressing to the EVR and to restrict flow from the EVR to the wound dressing.

9. The system of claim 1, and further comprising:
a source of liquid irrigant and gaseous irrigant; and
a valve positioned along the irrigant tubing and configured to switch between the liquid irrigant and the gaseous irrigant.

10. The system of claim 1, wherein the EVR is configured to operate in a continuous irrigation mode in addition to an intermittent irrigation mode.

11. The system of claim 1, and further comprising:
a collection bag fluidly connected to the vacuum tubing.

12. The system of claim 11, and further comprising:
hyper-absorbent spheres positioned in the collection bag.

13. The system of claim 12, wherein a cage structure is positioned in the collection bag.

14. The system of claim 11, wherein the collection bag comprises a bag inlet connected to the outlet of the wound dressing via the vacuum tubing and a bag outlet connected to the EVR via the vacuum tubing.

15. The system of claim 1, wherein:
the one or more processors are further configured to perform operations comprising determining that the irrigant flow satisfies one or more negative wound therapy criteria; and
the vacuum configuration is determined based on determining that the irrigant flow satisfies one or more negative wound therapy criteria.

16. The system of claim 15, wherein determining that the irrigant flow satisfies one or more negative wound therapy criteria comprises determining that a volume of the irrigant flow within the irrigant tubing exceeds a predetermined threshold.

17. A method of operating the system of claim 1, the method comprising:
positioning the wound dressing on a wound of a patient;
driving the EVR to intermittently apply negative pressure along the vacuum tubing; and
drawing the irrigant through the inlet, then over the wound, and then through the outlet toward the EVR.

18. The method of claim 17, the method further comprising:
alternating between liquid irrigant and gaseous irrigant; and
aerating the liquid irrigant with the gaseous irrigant.

19. The method of claim 17, the method further comprising:
agitating the irrigant as it crosses a surface of the wound to facilitate mixing of the irrigant with wound surface biological collections; and
cleansing, reducing bacterial burden, and maintain moisture at a surface of the wound via the irrigant.

20. A system comprising:
a wound dressing comprising an outlet and an inlet;
vacuum tubing connected to the outlet and configured to apply negative pressure to a wound surface;
a collection bag having a bag inlet and a bag outlet, wherein the bag inlet is fluidly connected to the dressing outlet via the vacuum tubing;
an irrigant source configured to provide an irrigant;
irrigant tubing connected to the irrigant source, further connected to the inlet, and configured to provide the irrigant to the wound surface; and
an electronic vacuum regulator (EVR) fluidly connected to the bag outlet via the vacuum tubing, wherein the EVR comprises:
a controller having one or more processors, and
a computer-readable storage medium coupled to the one or more processors having instructions stored thereon which, when executed by the one or more processors, cause the one or more processors to perform operations comprising:
monitoring an irrigant flow within the irrigant tubing,
determining an vacuum configuration for the EVR based on monitoring the irrigant flow within the irrigant tubing, wherein the vacuum configuration specifies a pre-programmed pattern of intervals to apply negative pressure with a force sufficient to (i) cause agitation of a volume of irrigant provided to the wound surface, and (ii) draw a portion of the volume of irrigant to be suctioned from the wound dressing into the collection bag, and
driving the EVR according to the vacuum configuration.

* * * * *